United States Patent
Gallo et al.

(10) Patent No.: US 12,427,151 B2
(45) Date of Patent: Sep. 30, 2025

(54) COMPOSITIONS AND METHOD OF TREATING CANCER

(71) Applicant: The Regents of the University of California, Oakland, CA (US)

(72) Inventors: Richard L. Gallo, San Diego, CA (US); Teruaki Nakatsuji, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 369 days.

(21) Appl. No.: 17/578,130

(22) Filed: Jan. 18, 2022

(65) Prior Publication Data

US 2022/0241288 A1    Aug. 4, 2022

Related U.S. Application Data

(62) Division of application No. 16/497,430, filed as application No. PCT/US2018/024511 on Mar. 27, 2018, now Pat. No. 11,260,058.

(60) Provisional application No. 62/638,058, filed on Mar. 2, 2018, provisional application No. 62/477,370, filed on Mar. 27, 2017.

(51) Int. Cl.
| | | |
|---|---|---|
| A61K 31/52 | (2006.01) | |
| A61K 9/00 | (2006.01) | |
| A61K 9/06 | (2006.01) | |
| A61K 35/741 | (2015.01) | |
| A61K 45/06 | (2006.01) | |
| A61P 31/00 | (2006.01) | |
| A61P 35/00 | (2006.01) | |
| A61F 13/00 | (2024.01) | |
| A61K 35/00 | (2006.01) | |
| A61L 15/40 | (2006.01) | |
| A61L 15/44 | (2006.01) | |
| A61P 17/16 | (2006.01) | |

(52) U.S. Cl.
CPC ............ *A61K 31/52* (2013.01); *A61K 9/0014* (2013.01); *A61K 9/06* (2013.01); *A61K 35/741* (2013.01); *A61P 31/00* (2018.01); *A61P 35/00* (2018.01); *A61K 45/06* (2013.01)

(58) Field of Classification Search
CPC ...................................................... A61K 31/52
See application file for complete search history.

(56) References Cited

U.S. PATENT DOCUMENTS

| | | | | |
|---|---|---|---|---|
| 11,260,058 B2 * | 3/2022 | Gallo | ............... | A61P 17/16 |
| 2005/0043328 A1 | 2/2005 | Dolezal et al. | | |
| 2013/0331384 A1 | 12/2013 | Gallo et al. | | |
| 2013/0338173 A1 | 12/2013 | Olhava et al. | | |

FOREIGN PATENT DOCUMENTS

| | | |
|---|---|---|
| CN | 1465582 A | 1/2004 |
| EP | 1724258 A1 | 11/2006 |
| WO | 98/39334 A1 | 9/1998 |
| WO | 2007/135380 A2 | 11/2007 |

OTHER PUBLICATIONS

Abdul-Masih et al., "Biochemical Studies on the Mutagen, 6-N-Hydroxylaminopurine", The Journal of Biological Chemistry, Feb. 15, 1986, vol. 261, No. 5, pp. 2020-2026.
Umeda, Takashi, Notification of Completion of Re-Examination, Japan Patent Office, Application No. 2019-552970, Appeal or Trial No. 2023-008456, Jul. 4, 2023.
Bakkestuen et al., "Synthesis and antimycobacterial activity of agelasine E and analogs", Org. Biomol. Chem., Jan. 1, 2005, vol. 3, No. 6, pp. 1025-1033.
Davenport, K.W., et al., "Complete Genome Assembly of *Staphylococcus epidermidis* AmMS 205", GenBank Accession No. CP009046, Nov. 13, 2014 [retrieved Aug. 1, 2018], https://www.ncbi.nlm.nih.gov/nuccore/CP009046.1/] p. 2-3.
Giner-Sorolla et al., "Synthesis and Properties of Some 6-Substituted Purines", Proc. Soc. Expl. Biol. and Med., 1958, vol. 80, No. 15, pp. 3932-3937.
Krajewski et al., "Antibacterial and antivirulence effect of 6-N-hydroxylaminopurine in Listeria monocytogenes", Nucleic Acids Research, Jan. 6, 2017, vol. 45, No. 4, pp. 1914-1924.
Lai et al., "Commensal skin bacteria as the probiotic of the cutaneous immune response", Expert Review of Dermatology, vol. 5, No. 3, Jun. 1, 2010, pp. 251-253.
Nakatsuji et al., "A commensal strain of *Staphylococcus epidermidis* protects against skin neoplasia", Sci. Adv., Feb. 28, 2018, vol. 4, No. 2, eaao4502, pp. 1-9.

(Continued)

*Primary Examiner* — Jeffrey H Murray
*Assistant Examiner* — Kevin S Martin
(74) *Attorney, Agent, or Firm* — Gavrilovich, Dodd & Lindsey LLP

(57) ABSTRACT

The disclosure describes methods and compositions for treating or preventing skin damage due to UV radiation. For example, the method includes contacting the skin with an effective amount of a composition containing the compound

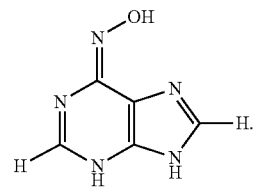

15 Claims, 28 Drawing Sheets
Specification includes a Sequence Listing.

(56) References Cited

OTHER PUBLICATIONS

Renard, Dephine, Extended European Search Report, Patent Application No. 18774237.4, European Patent Office, Dec. 2, 2020.
Sartorelli et al., "Some inhibitory properties of 6-N-Hydroxylaminopurine: An analog of adenine and hypoxanthine", Biochemical Pharmacology, Mar. 1, 1964, vol. 13, No. 3, pp. 507-515.
Shealy et al., Journal of Pharmaceutical Scences, 62(8):1252-7, 1973.
Wang, Xin, International Preliminary Report on Patentability and Written Opinion, PCT/US2018/024511, The International Bureau of WIPO, Oct. 10, 2019.
Young, Lee W., International Search Report and Written Opinion, PCT/US2018/024511, United States Patent and Trademark Office, Aug. 24, 2018.
Nakatsuji, T., "Firmocidin, a small molecule produced by S. epidermidis, provides antineoplastic and anti-biotic function from the commensal skin microbiome", Journal of Investigative Dermatology, May 2014, vol. 134, pp. S30.
Renard, Delphine, Office Action, Application No. 18774237.4, European Patent Office, Dec. 7, 2023.
Giner-Sorolla et al., "The Synthesis and Biological Properties of Hydroxylaminopurines and Related Derivatives", Journal of Medicinal Chemistry, May 1, 1968, 11(3), pp. 521-523.
Jean, Laura, Office Action, Canadian Intellectual Property Office, Application No. 3,057,978, May 17, 2024.

* cited by examiner d *S. epidermidis* M034 e *S. epidermidis* 1457 f  *S. epidermidis* MO34 g  *S. epidermidis* 1457

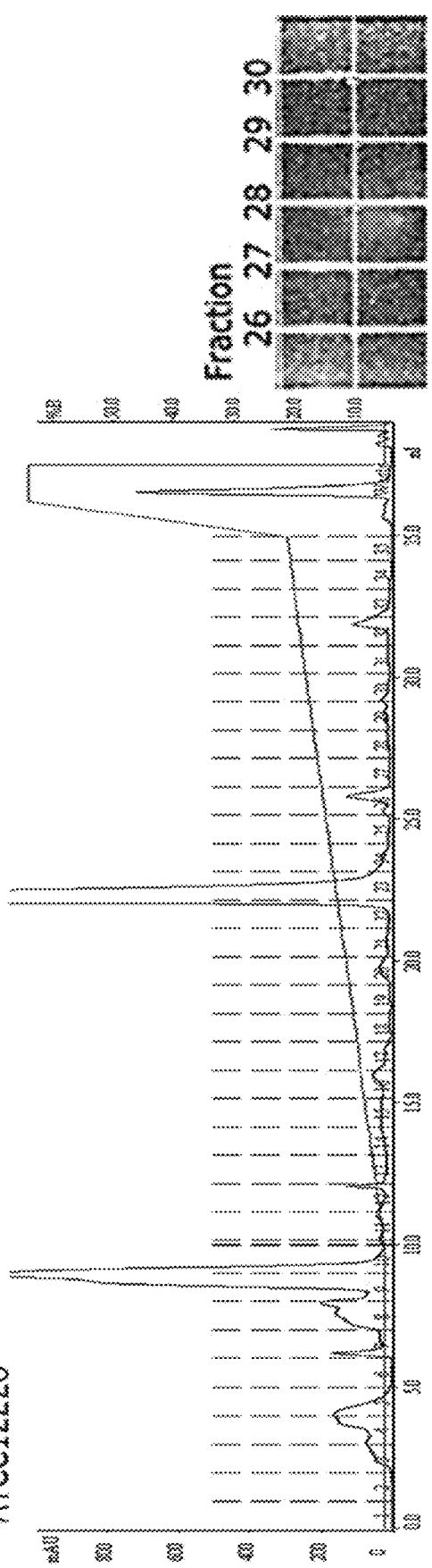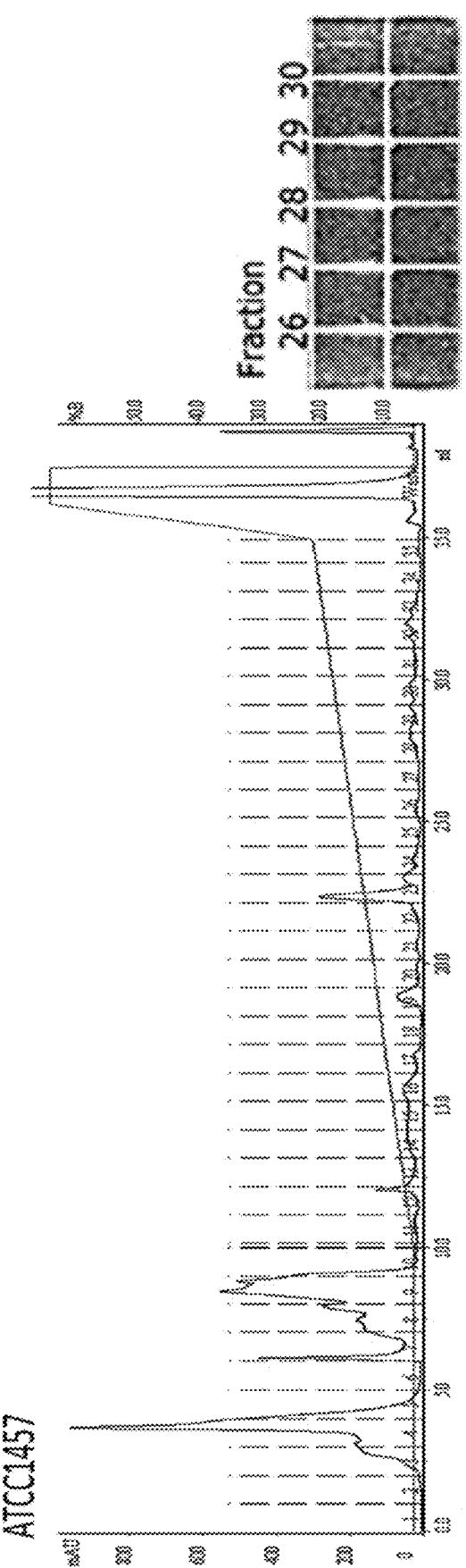
FIG. 8C
FIG. 8D

SEQUENCE LISTING

<160> NUMBER OF SEQ ID NOS: 58

<210> SEQ ID NO 1
<211> LENGTH: 132
<212> TYPE: DNA
<213> ORGANISM: Artificial Sequence
<220> FEATURE:
<223> OTHER INFORMATION: hypothetical coding sequence
<220> FEATURE:
<221> NAME/KEY: CDS
<222> LOCATION: (1)..(132)

<400> SEQUENCE: 1

```
atg agt gct gtt tta tta tca gca att agt cca acg gca agt gta aat      48
Met Ser Ala Val Leu Leu Ser Ala Ile Ser Pro Thr Ala Ser Val Asn
1               5                   10                  15 gaa tca ata gaa ttg tac aag tca gtt agc aag tcg aat ata gaa att      96
Glu Ser Ile Glu Leu Tyr Lys Ser Val Ser Lys Ser Asn Ile Glu Ile
                20                  25                  30 gaa aaa gat aat aag act tta gat gat tcg ttt taa                     132
Glu Lys Asp Asn Lys Thr Leu Asp Asp Ser Phe
                35                  40
```

<210> SEQ ID NO 2
<211> LENGTH: 43
<212> TYPE: PRT
<213> ORGANISM: Artificial Sequence
<220> FEATURE:
<223> OTHER INFORMATION: Synthetic Construct

<400> SEQUENCE: 2

```
Met Ser Ala Val Leu Leu Ser Ala Ile Ser Pro Thr Ala Ser Val Asn
1               5                   10                  15

Glu Ser Ile Glu Leu Tyr Lys Ser Val Ser Lys Ser Asn Ile Glu Ile
                20                  25                  30

Glu Lys Asp Asn Lys Thr Leu Asp Asp Ser Phe
                35                  40
```

<210> SEQ ID NO 3
<211> LENGTH: 120
<212> TYPE: DNA
<213> ORGANISM: Staphylococcus epidermidis
<220> FEATURE:
<221> NAME/KEY: CDS
<222> LOCATION: (1)..(120)

<400> SEQUENCE: 3

```
atg att cgt ttt aaa atc cta aat atg gta act gaa cag act att aat      48
Met Ile Arg Phe Lys Ile Leu Asn Met Val Thr Glu Gln Thr Ile Asn
1               5                   10                  15 agt tta cca tat aat ctt aaa gaa ggg act tca gaa aga att ggt ggt      96
Ser Leu Pro Tyr Asn Leu Lys Glu Gly Thr Ser Glu Arg Ile Gly Gly
                20                  25                  30 tcc ttt act gta aaa aag gat taa                                     120
Ser Phe Thr Val Lys Lys Asp
                35
```

<210> SEQ ID NO 4
<211> LENGTH: 39

<212> TYPE: PRT
<213> ORGANISM: Staphylococcus epidermidis

<400> SEQUENCE: 4

Met Ile Arg Phe Lys Ile Leu Asn Met Val Thr Glu Gln Thr Ile Asn
1               5                   10                  15

Ser Leu Pro Tyr Asn Leu Lys Glu Gly Thr Ser Glu Arg Ile Gly Gly
            20                  25                  30

Ser Phe Thr Val Lys Lys Asp
        35

<210> SEQ ID NO 5
<211> LENGTH: 249
<212> TYPE: DNA
<213> ORGANISM: Artificial Sequence
<220> FEATURE:
<223> OTHER INFORMATION: YefM protein
<220> FEATURE:
<221> NAME/KEY: CDS
<222> LOCATION: (1)..(249)

<400> SEQUENCE: 5 atg act gtt aaa tcc tat tca tat gta cgt gaa cat ttc aaa gac atg    48
Met Thr Val Lys Ser Tyr Ser Tyr Val Arg Glu His Phe Lys Asp Met
1               5                   10                  15 att aat aaa gtt aat gat gat agc gat acg ata aca att aca aca aaa    96
Ile Asn Lys Val Asn Asp Asp Ser Asp Thr Ile Thr Ile Thr Thr Lys
            20                  25                  30 gac cgt aat gca gtt atg atg tca gaa gat aat tat aat gaa ata atg    144
Asp Arg Asn Ala Val Met Met Ser Glu Asp Asn Tyr Asn Glu Ile Met
        35                  40                  45 gag aca cta tac ttg caa caa aat cct gcc aat gca aaa tat tta tca    192
Glu Thr Leu Tyr Leu Gln Gln Asn Pro Ala Asn Ala Lys Tyr Leu Ser
    50                  55                  60 gaa tcc att gaa aac cta gaa cgt ggt aat ata aaa act aag gat att    240
Glu Ser Ile Glu Asn Leu Glu Arg Gly Asn Ile Lys Thr Lys Asp Ile
65                  70                  75                  80 ttg ata taa                                                        249
Leu Ile

<210> SEQ ID NO 6
<211> LENGTH: 82
<212> TYPE: PRT
<213> ORGANISM: Artificial Sequence
<220> FEATURE:
<223> OTHER INFORMATION: Synthetic Construct

<400> SEQUENCE: 6

Met Thr Val Lys Ser Tyr Ser Tyr Val Arg Glu His Phe Lys Asp Met
1               5                   10                  15

Ile Asn Lys Val Asn Asp Asp Ser Asp Thr Ile Thr Ile Thr Thr Lys
            20                  25                  30

Asp Arg Asn Ala Val Met Met Ser Glu Asp Asn Tyr Asn Glu Ile Met
        35                  40                  45

Glu Thr Leu Tyr Leu Gln Gln Asn Pro Ala Asn Ala Lys Tyr Leu Ser
    50                  55                  60

Glu Ser Ile Glu Asn Leu Glu Arg Gly Asn Ile Lys Thr Lys Asp Ile
65                  70                  75                  80

Leu Ile

<210> SEQ ID NO 7

```
<211> LENGTH: 285
<212> TYPE: DNA
<213> ORGANISM: Staphylococcus epidermidis
<220> FEATURE:
<221> NAME/KEY: CDS
<222> LOCATION: (1)..(285)

<400> SEQUENCE: 7 atg tta gat aaa gaa aag caa aaa gaa gct atg cct att att caa gga        48
Met Leu Asp Lys Glu Lys Gln Lys Glu Ala Met Pro Ile Ile Gln Gly
1               5                   10                  15 gag tac aaa tca gat gaa cca att aat tac att aaa gca aac aca atc        96
Glu Tyr Lys Ser Asp Glu Pro Ile Asn Tyr Ile Lys Ala Asn Thr Ile
                20                  25                  30 cca aac aaa gct aca tca acg act ttt gga tat gaa aag atg att agt       144
Pro Asn Lys Ala Thr Ser Thr Thr Phe Gly Tyr Glu Lys Met Ile Ser
            35                  40                  45 aaa gag gct atg acg cca gaa atg tta gag gtt cgt caa ata att ctt       192
Lys Glu Ala Met Thr Pro Glu Met Leu Glu Val Arg Gln Ile Ile Leu
        50                  55                  60 aat gat gtg gta aag ctc aca gaa tca atg aat caa ttt aaa ctt gat       240
Asn Asp Val Val Lys Leu Thr Glu Ser Met Asn Gln Phe Lys Leu Asp
65                  70                  75                  80 att aaa gtt agt aaa gta att tat gac aaa tat ggg gtg aga taa           285
Ile Lys Val Ser Lys Val Ile Tyr Asp Lys Tyr Gly Val Arg
                85                  90

<210> SEQ ID NO 8
<211> LENGTH: 94
<212> TYPE: PRT
<213> ORGANISM: Staphylococcus epidermidis

<400> SEQUENCE: 8

Met Leu Asp Lys Glu Lys Gln Lys Glu Ala Met Pro Ile Ile Gln Gly
1               5                   10                  15

Glu Tyr Lys Ser Asp Glu Pro Ile Asn Tyr Ile Lys Ala Asn Thr Ile
                20                  25                  30

Pro Asn Lys Ala Thr Ser Thr Thr Phe Gly Tyr Glu Lys Met Ile Ser
            35                  40                  45

Lys Glu Ala Met Thr Pro Glu Met Leu Glu Val Arg Gln Ile Ile Leu
        50                  55                  60

Asn Asp Val Val Lys Leu Thr Glu Ser Met Asn Gln Phe Lys Leu Asp
65                  70                  75                  80

Ile Lys Val Ser Lys Val Ile Tyr Asp Lys Tyr Gly Val Arg
                85                  90

<210> SEQ ID NO 9
<211> LENGTH: 258
<212> TYPE: DNA
<213> ORGANISM: Staphylococcus epidermidis
<220> FEATURE:
<221> NAME/KEY: CDS
<222> LOCATION: (1)..(258)

<400> SEQUENCE: 9 atg att aaa caa att ttc aat gat aaa gaa att cgg ttt atc gaa aaa        48
Met Ile Lys Gln Ile Phe Asn Asp Lys Glu Ile Arg Phe Ile Glu Lys
1               5                   10                  15 gaa gat gaa tat tgg gca gta gct gga gat gtg gca aag gta ttg ggg        96
Glu Asp Glu Tyr Trp Ala Val Ala Gly Asp Val Ala Lys Val Leu Gly
                20                  25                  30 tac tca cat aca cca cac atg act aga tta tta gat gaa tca gaa aag       144
```

```
                Tyr Ser His Thr Pro His Met Thr Arg Leu Leu Asp Glu Ser Glu Lys
                         35                  40                  45 gct gtc cat aat gtg gtc acc gtt aaa ggt aaa caa aat gct gtg atc       192
Ala Val His Asn Val Val Thr Val Lys Gly Lys Gln Asn Ala Val Ile
 50                  55                  60 ata tta gaa ata ggt att tat gaa gct att tgg aat agt aga aga gat       240
Ile Leu Glu Ile Gly Ile Tyr Glu Ala Ile Trp Asn Ser Arg Arg Asp
 65                  70                  75                  80 gaa gct caa gaa ttt tag                                               258
Glu Ala Gln Glu Phe
                 85

<210> SEQ ID NO 10
<211> LENGTH: 85
<212> TYPE: PRT
<213> ORGANISM: Staphylococcus epidermidis

<400> SEQUENCE: 10

Met Ile Lys Gln Ile Phe Asn Asp Lys Glu Ile Arg Phe Ile Glu Lys
  1               5                  10                  15

Glu Asp Glu Tyr Trp Ala Val Ala Gly Asp Val Ala Lys Val Leu Gly
                 20                  25                  30

Tyr Ser His Thr Pro His Met Thr Arg Leu Leu Asp Glu Ser Glu Lys
             35                  40                  45

Ala Val His Asn Val Val Thr Val Lys Gly Lys Gln Asn Ala Val Ile
 50                  55                  60

Ile Leu Glu Ile Gly Ile Tyr Glu Ala Ile Trp Asn Ser Arg Arg Asp
 65                  70                  75                  80

Glu Ala Gln Glu Phe
                 85

<210> SEQ ID NO 11
<211> LENGTH: 219
<212> TYPE: DNA
<213> ORGANISM: Staphylococcus epidermidis
<220> FEATURE:
<221> NAME/KEY: CDS
<222> LOCATION: (1)..(219)

<400> SEQUENCE: 11 gtg gtt aac aac gtt aaa aga ata cga aaa aat aaa aaa att acc att        48
Val Val Asn Asn Val Lys Arg Ile Arg Lys Asn Lys Lys Ile Thr Ile
  1               5                  10                  15 act gaa tta agt aga aaa agt ggg ata agc aga aca act ata tac aaa        96
Thr Glu Leu Ser Arg Lys Ser Gly Ile Ser Arg Thr Thr Ile Tyr Lys
                 20                  25                  30 tta gaa tct caa aaa tca aat ccc agc ttg gaa acc att caa aaa ata       144
Leu Glu Ser Gln Lys Ser Asn Pro Ser Leu Glu Thr Ile Gln Lys Ile
             35                  40                  45 tct tct ggt tta gat gaa aaa cca gaa aaa att ttt aac ctc att gtt       192
Ser Ser Gly Leu Asp Glu Lys Pro Glu Lys Ile Phe Asn Leu Ile Val
 50                  55                  60 att caa gaa tta caa aag gag cct taa                                   219
Ile Gln Glu Leu Gln Lys Glu Pro
 65                  70

<210> SEQ ID NO 12
<211> LENGTH: 72
<212> TYPE: PRT
<213> ORGANISM: Staphylococcus epidermidis

<400> SEQUENCE: 12
```

```
Val Val Asn Asn Val Lys Arg Ile Arg Lys Asn Lys Lys Ile Thr Ile
1               5                   10                  15

Thr Glu Leu Ser Arg Lys Ser Gly Ile Ser Arg Thr Thr Ile Tyr Lys
            20                  25                  30

Leu Glu Ser Gln Lys Ser Asn Pro Ser Leu Glu Thr Ile Gln Lys Ile
        35                  40                  45

Ser Ser Gly Leu Asp Glu Lys Pro Glu Lys Ile Phe Asn Leu Ile Val
50                  55                  60

Ile Gln Glu Leu Gln Lys Glu Pro
65                  70

<210> SEQ ID NO 13
<211> LENGTH: 585
<212> TYPE: DNA
<213> ORGANISM: Staphylococcus epidermidis
<220> FEATURE:
<221> NAME/KEY: CDS
<222> LOCATION: (1)..(585)

<400> SEQUENCE: 13
```

| | | | | | | | | | | | | | | | | |
|---|---|---|---|---|---|---|---|---|---|---|---|---|---|---|---|---|
| gtg aat gac ttt gga aag aaa tta aaa gaa tta aga ggc gac caa tca | | | | | | | | | | | | | | | | 48 |
| Val Asn Asp Phe Gly Lys Lys Leu Lys Glu Leu Arg Gly Asp Gln Ser | | | | | | | | | | | | | | | | |
| 1 5 10 15 | | | | | | | | | | | | | | | | |
| att aga gaa gcc tct agg aat att ggt ata agt cac act tat tta gat | | | | | | | | | | | | | | | | 96 |
| Ile Arg Glu Ala Ser Arg Asn Ile Gly Ile Ser His Thr Tyr Leu Asp | | | | | | | | | | | | | | | | |
| 20 25 30 | | | | | | | | | | | | | | | | |
| agt tta gaa aaa ggt att gat cca aga act ggc aaa gaa aga aaa cct | | | | | | | | | | | | | | | | 144 |
| Ser Leu Glu Lys Gly Ile Asp Pro Arg Thr Gly Lys Glu Arg Lys Pro | | | | | | | | | | | | | | | | |
| 35 40 45 | | | | | | | | | | | | | | | | |
| aca att gaa gta att cat aaa cta tca aaa tat tat aat gtt gat ttt | | | | | | | | | | | | | | | | 192 |
| Thr Ile Glu Val Ile His Lys Leu Ser Lys Tyr Tyr Asn Val Asp Phe | | | | | | | | | | | | | | | | |
| 50 55 60 | | | | | | | | | | | | | | | | |
| ttt gat tta agc aga tta gca ggt gtg ttt gta tca att aaa gat acg | | | | | | | | | | | | | | | | 240 |
| Phe Asp Leu Ser Arg Leu Ala Gly Val Phe Val Ser Ile Lys Asp Thr | | | | | | | | | | | | | | | | |
| 65 70 75 80 | | | | | | | | | | | | | | | | |
| cct aaa gaa gat aag cga gaa gaa att aac aaa atg aag aaa aga ttt | | | | | | | | | | | | | | | | 288 |
| Pro Lys Glu Asp Lys Arg Glu Glu Ile Asn Lys Met Lys Lys Arg Phe | | | | | | | | | | | | | | | | |
| 85 90 95 | | | | | | | | | | | | | | | | |
| aaa gaa tat ttt aac gat aca gaa ctt att gtt aaa gaa aat tat ctt | | | | | | | | | | | | | | | | 336 |
| Lys Glu Tyr Phe Asn Asp Thr Glu Leu Ile Val Lys Glu Asn Tyr Leu | | | | | | | | | | | | | | | | |
| 100 105 110 | | | | | | | | | | | | | | | | |
| gat att atg aca aaa aag tta agt tat cat gaa att att ttt tgg caa | | | | | | | | | | | | | | | | 384 |
| Asp Ile Met Thr Lys Lys Leu Ser Tyr His Glu Ile Ile Phe Trp Gln | | | | | | | | | | | | | | | | |
| 115 120 125 | | | | | | | | | | | | | | | | |
| aat tta tat aat ttt tat att caa gaa aaa gat tct gat tat cta aaa | | | | | | | | | | | | | | | | 432 |
| Asn Leu Tyr Asn Phe Tyr Ile Gln Glu Lys Asp Ser Asp Tyr Leu Lys | | | | | | | | | | | | | | | | |
| 130 135 140 | | | | | | | | | | | | | | | | |
| ata aaa gat gaa gaa gat aca gat att tta aca ttt ata gct tcc ttg | | | | | | | | | | | | | | | | 480 |
| Ile Lys Asp Glu Glu Asp Thr Asp Ile Leu Thr Phe Ile Ala Ser Leu | | | | | | | | | | | | | | | | |
| 145 150 155 160 | | | | | | | | | | | | | | | | |
| ttt aaa ata tta act gaa aat aaa aat tct aat gat gac gaa ata ttt | | | | | | | | | | | | | | | | 528 |
| Phe Lys Ile Leu Thr Glu Asn Lys Asn Ser Asn Asp Asp Glu Ile Phe | | | | | | | | | | | | | | | | |
| 165 170 175 | | | | | | | | | | | | | | | | |
| aaa ggc att tcg aat gat ttt aat aaa ttc tta aaa tca tac tta aat | | | | | | | | | | | | | | | | 576 |
| Lys Gly Ile Ser Asn Asp Phe Asn Lys Phe Leu Lys Ser Tyr Leu Asn | | | | | | | | | | | | | | | | |
| 180 185 190 | | | | | | | | | | | | | | | | |
| att aag tag | | | | | | | | | | | | | | | | 585 |
| Ile Lys | | | | | | | | | | | | | | | | |

```
<210> SEQ ID NO 14
<211> LENGTH: 194
<212> TYPE: PRT
<213> ORGANISM: Staphylococcus epidermidis

<400> SEQUENCE: 14

Val Asn Asp Phe Gly Lys Lys Leu Lys Glu Leu Arg Gly Asp Gln Ser
1               5                   10                  15

Ile Arg Glu Ala Ser Arg Asn Ile Gly Ile Ser His Thr Tyr Leu Asp
                20                  25                  30

Ser Leu Glu Lys Gly Ile Asp Pro Arg Thr Gly Lys Glu Arg Lys Pro
            35                  40                  45

Thr Ile Glu Val Ile His Lys Leu Ser Lys Tyr Tyr Asn Val Asp Phe
        50                  55                  60

Phe Asp Leu Ser Arg Leu Ala Gly Val Phe Val Ser Ile Lys Asp Thr
65                  70                  75                  80

Pro Lys Glu Asp Lys Arg Glu Glu Ile Asn Lys Met Lys Lys Arg Phe
                85                  90                  95

Lys Glu Tyr Phe Asn Asp Thr Glu Leu Ile Val Lys Glu Asn Tyr Leu
                100                 105                 110

Asp Ile Met Thr Lys Lys Leu Ser Tyr His Glu Ile Ile Phe Trp Gln
            115                 120                 125

Asn Leu Tyr Asn Phe Tyr Ile Gln Glu Lys Asp Ser Asp Tyr Leu Lys
        130                 135                 140

Ile Lys Asp Glu Glu Asp Thr Asp Ile Leu Thr Phe Ile Ala Ser Leu
145                 150                 155                 160

Phe Lys Ile Leu Thr Glu Asn Lys Asn Ser Asn Asp Asp Glu Ile Phe
                165                 170                 175

Lys Gly Ile Ser Asn Asp Phe Asn Lys Phe Leu Lys Ser Tyr Leu Asn
                180                 185                 190

Ile Lys

<210> SEQ ID NO 15
<211> LENGTH: 234
<212> TYPE: DNA
<213> ORGANISM: Staphylococcus epidermidis
<220> FEATURE:
<221> NAME/KEY: CDS
<222> LOCATION: (1)..(234)

<400> SEQUENCE: 15 atg att aac act gcc gtc act ggt gct gaa cct gga ggt aac tgg aat     48
Met Ile Asn Thr Ala Val Thr Gly Ala Glu Pro Gly Gly Asn Trp Asn
1               5                   10                  15 cca aat atc atg ata agc tgc gct act ata gca aag atg cca cat ccc     96
Pro Asn Ile Met Ile Ser Cys Ala Thr Ile Ala Lys Met Pro His Pro
                20                  25                  30 agt gca cca gca gtt ctt aac cct aat aat atc gct aga atc atg att    144
Ser Ala Pro Ala Val Leu Asn Pro Asn Asn Ile Ala Arg Ile Met Ile
            35                  40                  45 atg att tct atg ata aac aat aac atg gaa gaa tct cct aac tta tgc    192
Met Ile Ser Met Ile Asn Asn Asn Met Glu Glu Ser Pro Asn Leu Cys
        50                  55                  60 cga aca att ttc act tca ata ttt tat cac ttt aat atg taa            234
Arg Thr Ile Phe Thr Ser Ile Phe Tyr His Phe Asn Met
65                  70                  75

<210> SEQ ID NO 16
<211> LENGTH: 77
```

```
<212> TYPE: PRT
<213> ORGANISM: Staphylococcus epidermidis

<400> SEQUENCE: 16

Met Ile Asn Thr Ala Val Thr Gly Ala Glu Pro Gly Gly Asn Trp Asn
1               5                   10                  15

Pro Asn Ile Met Ile Ser Cys Ala Thr Ile Ala Lys Met Pro His Pro
            20                  25                  30

Ser Ala Pro Ala Val Leu Asn Pro Asn Asn Ile Ala Arg Ile Met Ile
        35                  40                  45

Met Ile Ser Met Ile Asn Asn Asn Met Glu Glu Ser Pro Asn Leu Cys
    50                  55                  60

Arg Thr Ile Phe Thr Ser Ile Phe Tyr His Phe Asn Met
65                  70                  75

<210> SEQ ID NO 17
<211> LENGTH: 135
<212> TYPE: DNA
<213> ORGANISM: Staphylococcus epidermidis
<220> FEATURE:
<221> NAME/KEY: CDS
<222> LOCATION: (1)..(135)

<400> SEQUENCE: 17 atg ccg gaa gtt tcc gga gaa atc gct ttt aat ttt tca gca att tta      48
Met Pro Glu Val Ser Gly Glu Ile Ala Phe Asn Phe Ser Ala Ile Leu
1               5                   10                  15 gcc gca gct ata aca agt gat aaa gtt gat gta agt aag aaa gca gat      96
Ala Ala Ala Ile Thr Ser Asp Lys Val Asp Val Ser Lys Lys Ala Asp
            20                  25                  30 gca att gta gtt ttg gtg tca aac cag cgt cta atg taa                 135
Ala Ile Val Val Leu Val Ser Asn Gln Arg Leu Met
        35                  40

<210> SEQ ID NO 18
<211> LENGTH: 44
<212> TYPE: PRT
<213> ORGANISM: Staphylococcus epidermidis

<400> SEQUENCE: 18

Met Pro Glu Val Ser Gly Glu Ile Ala Phe Asn Phe Ser Ala Ile Leu
1               5                   10                  15

Ala Ala Ala Ile Thr Ser Asp Lys Val Asp Val Ser Lys Lys Ala Asp
            20                  25                  30

Ala Ile Val Val Leu Val Ser Asn Gln Arg Leu Met
        35                  40

<210> SEQ ID NO 19
<211> LENGTH: 117
<212> TYPE: DNA
<213> ORGANISM: Staphylococcus epidermidis
<220> FEATURE:
<221> NAME/KEY: CDS
<222> LOCATION: (1)..(117)

<400> SEQUENCE: 19 atg ccg gca cca atc gct tgg ata atc cga gat atc att aaa ata gaa      48
Met Pro Ala Pro Ile Ala Trp Ile Ile Arg Asp Ile Ile Lys Ile Glu
1               5                   10                  15 aaa gta ggt gaa act gct gct aca aca gat cct ata aga aaa att gcc      96
Lys Val Gly Glu Thr Ala Ala Thr Thr Asp Pro Ile Arg Lys Ile Ala
            20                  25                  30
```

```
att gag aaa ata tat aaa tga                                              117
Ile Glu Lys Ile Tyr Lys
        35
```

<210> SEQ ID NO 20
<211> LENGTH: 38
<212> TYPE: PRT
<213> ORGANISM: Staphylococcus epidermidis

<400> SEQUENCE: 20

```
Met Pro Ala Pro Ile Ala Trp Ile Ile Arg Asp Ile Lys Ile Glu
1               5                   10                  15

Lys Val Gly Glu Thr Ala Ala Thr Thr Asp Pro Ile Arg Lys Ile Ala
            20                  25                  30

Ile Glu Lys Ile Tyr Lys
        35
```

<210> SEQ ID NO 21
<211> LENGTH: 753
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(753)

<400> SEQUENCE: 21

```
ttg cct aag aca cct gaa gat ggg aaa cca agt gta gat aag aaa agc        48
Leu Pro Lys Thr Pro Glu Asp Gly Lys Pro Ser Val Asp Lys Lys Ser
1               5                   10                  15 ttt gta agt gaa act att tta ttt tta ttt atg tcg att cta gga gaa        96
Phe Val Ser Glu Thr Ile Leu Phe Leu Phe Met Ser Ile Leu Gly Glu
            20                  25                  30 gtt ttt ggc tat gaa gat gaa aaa gat gga caa ctt gta cat gat att       144
Val Phe Gly Tyr Glu Asp Glu Lys Asp Gly Gln Leu Val His Asp Ile
        35                  40                  45 tct cca ata aaa gga caa gaa aaa aat ata gaa aat tct ggt tca gat       192
Ser Pro Ile Lys Gly Gln Glu Lys Asn Ile Glu Asn Ser Gly Ser Asp
    50                  55                  60 gtg ttt ttc tct tat cat gta gaa gac gca ata cat cca tat aaa cca       240
Val Phe Phe Ser Tyr His Val Glu Asp Ala Ile His Pro Tyr Lys Pro
65                  70                  75                  80 gat tat ctt gct tta tat tgt ttg aaa tcg gat cat gag aaa ata gct       288
Asp Tyr Leu Ala Leu Tyr Cys Leu Lys Ser Asp His Glu Lys Ile Ala
                85                  90                  95 ata aca gag aca tct tct att agt gaa gca atg aaa aga tta agt acg       336
Ile Thr Glu Thr Ser Ser Ile Ser Glu Ala Met Lys Arg Leu Ser Thr
            100                 105                 110 tca acg ctt aat att ctt aga aaa ccc atg tat gaa tta cat cca cct       384
Ser Thr Leu Asn Ile Leu Arg Lys Pro Met Tyr Glu Leu His Pro Pro
        115                 120                 125 gct tct ttt aat tca agt cat tta tct aga aaa gta tca gta ata gga       432
Ala Ser Phe Asn Ser Ser His Leu Ser Arg Lys Val Ser Val Ile Gly
    130                 135                 140 gga agt caa aag aat cct gaa tta tta att cat gaa aca tta atg caa       480
Gly Ser Gln Lys Asn Pro Glu Leu Leu Ile His Glu Thr Leu Met Gln
145                 150                 155                 160 gga ata gaa gat gaa gca gaa aaa gca tta agt gaa ttg aaa gaa acg       528
Gly Ile Glu Asp Glu Ala Glu Lys Ala Leu Ser Glu Leu Lys Glu Thr
                165                 170                 175 tta ccg gaa gtt tca aat gga gtt caa tta aac cca gga gaa ctt att       576
Leu Pro Glu Val Ser Asn Gly Val Gln Leu Asn Pro Gly Glu Leu Ile
```

```
Leu Pro Glu Val Ser Asn Gly Val Gln Leu Asn Pro Gly Glu Leu Ile
            180                 185                 190 att tta gat aat aat aaa gca gca cat gct aga tca gct ttt aaa ccc    624
Ile Leu Asp Asn Asn Lys Ala Ala His Ala Arg Ser Ala Phe Lys Pro
            195                 200                 205 aga tat gac ggt gaa gat aga tgg cta caa aga atg ttt tct att aat    672
Arg Tyr Asp Gly Glu Asp Arg Trp Leu Gln Arg Met Phe Ser Ile Asn
210                 215                 220 gac tta aaa gga tta gag gat tac atg aaa gaa gac gaa aat ata ttt    720
Asp Leu Lys Gly Leu Glu Asp Tyr Met Lys Glu Asp Glu Asn Ile Phe
225                 230                 235                 240 gta ccc ttg gtg gat ata tta aaa gac aaa taa                        753
Val Pro Leu Val Asp Ile Leu Lys Asp Lys
                245                 250

<210> SEQ ID NO 22
<211> LENGTH: 250
<212> TYPE: PRT
<213> ORGANISM: Artificial Sequence
<220> FEATURE:
<223> OTHER INFORMATION: Synthetic Construct

<400> SEQUENCE: 22

Leu Pro Lys Thr Pro Glu Asp Gly Lys Pro Ser Val Asp Lys Lys Ser
1               5                   10                  15

Phe Val Ser Glu Thr Ile Leu Phe Leu Phe Met Ser Ile Leu Gly Glu
            20                  25                  30

Val Phe Gly Tyr Glu Asp Glu Lys Asp Gly Gln Leu Val His Asp Ile
        35                  40                  45

Ser Pro Ile Lys Gly Gln Glu Lys Asn Ile Glu Asn Ser Gly Ser Asp
    50                  55                  60

Val Phe Phe Ser Tyr His Val Glu Asp Ala Ile His Pro Tyr Lys Pro
65                  70                  75                  80

Asp Tyr Leu Ala Leu Tyr Cys Leu Lys Ser Asp His Glu Lys Ile Ala
                85                  90                  95

Ile Thr Glu Thr Ser Ser Ile Ser Glu Ala Met Lys Arg Leu Ser Thr
            100                 105                 110

Ser Thr Leu Asn Ile Leu Arg Lys Pro Met Tyr Glu Leu His Pro Pro
        115                 120                 125

Ala Ser Phe Asn Ser Ser His Leu Ser Arg Lys Val Ser Val Ile Gly
    130                 135                 140

Gly Ser Gln Lys Asn Pro Glu Leu Leu Ile His Glu Thr Leu Met Gln
145                 150                 155                 160

Gly Ile Glu Asp Glu Ala Glu Lys Ala Leu Ser Glu Leu Lys Glu Thr
                165                 170                 175

Leu Pro Glu Val Ser Asn Gly Val Gln Leu Asn Pro Gly Glu Leu Ile
            180                 185                 190

Ile Leu Asp Asn Asn Lys Ala Ala His Ala Arg Ser Ala Phe Lys Pro
        195                 200                 205

Arg Tyr Asp Gly Glu Asp Arg Trp Leu Gln Arg Met Phe Ser Ile Asn
    210                 215                 220

Asp Leu Lys Gly Leu Glu Asp Tyr Met Lys Glu Asp Glu Asn Ile Phe
225                 230                 235                 240

Val Pro Leu Val Asp Ile Leu Lys Asp Lys
                245                 250

<210> SEQ ID NO 23
```

<211> LENGTH: 846
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(846)

<400> SEQUENCE: 23

```
atg aac ttt aaa acg aat ttt aaa ggt ttg ttt agt ata gaa aag aaa      48
Met Asn Phe Lys Thr Asn Phe Lys Gly Leu Phe Ser Ile Glu Lys Lys
1               5                   10                  15 ttt aat gta aat tta ttg cca tct caa ctc aaa tta gaa gat aaa ata      96
Phe Asn Val Asn Leu Leu Pro Ser Gln Leu Lys Leu Glu Asp Lys Ile
            20                  25                  30 aac att ttt tgg gca acg tta atg agg gtt gta ggc tgg ctt tta tat    144
Asn Ile Phe Trp Ala Thr Leu Met Arg Val Val Gly Trp Leu Leu Tyr
        35                  40                  45 aca tta tta att gca agt atg act gaa gtt aaa aat aat aat att att    192
Thr Leu Leu Ile Ala Ser Met Thr Glu Val Lys Asn Asn Asn Ile Ile
    50                  55                  60 ata tac ata tca tgt att ttg ata gta gtc tta tta ata ttt gat ata    240
Ile Tyr Ile Ser Cys Ile Leu Ile Val Val Leu Leu Ile Phe Asp Ile
65                  70                  75                  80 agt tca atc ttt ctt att tct gat gat atg aga aag aaa aat tat aga    288
Ser Ser Ile Phe Leu Ile Ser Asp Asp Met Arg Lys Lys Asn Tyr Arg
                85                  90                  95 tat ttg ttt atc aaa aga gac gaa gaa tat tat cgt tta gat aaa tat    336
Tyr Leu Phe Ile Lys Arg Asp Glu Glu Tyr Tyr Arg Leu Asp Lys Tyr
            100                 105                 110 ttt tac gat att tct gat aaa caa gtt tta caa tat act gta aat gaa    384
Phe Tyr Asp Ile Ser Asp Lys Gln Val Leu Gln Tyr Thr Val Asn Glu
        115                 120                 125 aaa gat atg aaa att gaa aaa aat aat ggc gat cca aaa att gat gag    432
Lys Asp Met Lys Ile Glu Lys Asn Asn Gly Asp Pro Lys Ile Asp Glu
    130                 135                 140 aaa gaa aaa ata gtt gga aaa aag att gtt act gaa aag ata aat agt    480
Lys Glu Lys Ile Val Gly Lys Lys Ile Val Thr Glu Lys Ile Asn Ser
145                 150                 155                 160 gat aaa gtc aat aca ttt atc caa act gat agc gag gct aca tat agt    528
Asp Lys Val Asn Thr Phe Ile Gln Thr Asp Ser Glu Ala Thr Tyr Ser
                165                 170                 175 agc aaa tat att act tta gta cct att gtt caa aac att ata ttg ata    576
Ser Lys Tyr Ile Thr Leu Val Pro Ile Val Gln Asn Ile Ile Leu Ile
            180                 185                 190 ata agt ata ata tta aca gct tgt ttt cat aaa ctt tgg att gtt ata    624
Ile Ser Ile Ile Leu Thr Ala Cys Phe His Lys Leu Trp Ile Val Ile
        195                 200                 205 tta tgt ctt atc ata tat ttt ttg tta aat gga ata ttt aca cta cga    672
Leu Cys Leu Ile Ile Tyr Phe Leu Leu Asn Gly Ile Phe Thr Leu Arg
    210                 215                 220 tta tca tct aat gta aat gaa act tta gaa aat aac aat ata aag caa    720
Leu Ser Ser Asn Val Asn Glu Thr Leu Glu Asn Asn Asn Ile Lys Gln
225                 230                 235                 240 gtt aaa aat aaa gtg aaa aat cat ttt aat gaa gac gaa aat gat aat    768
Val Lys Asn Lys Val Lys Asn His Phe Asn Glu Asp Glu Asn Asp Asn
                245                 250                 255 gtt gga gat aaa aag gat agc tat gaa cac cgt gat aag aat atc aat    816
Val Gly Asp Lys Lys Asp Ser Tyr Glu His Arg Asp Lys Asn Ile Asn
            260                 265                 270
```

```
att atc gtt gtt aat gaa cta aaa aag taa                                                846
Ile Ile Val Val Asn Glu Leu Lys Lys
        275             280
```

<210> SEQ ID NO 24
<211> LENGTH: 281
<212> TYPE: PRT
<213> ORGANISM: Artificial Sequence
<220> FEATURE:
<223> OTHER INFORMATION: Synthetic Construct

<400> SEQUENCE: 24

```
Met Asn Phe Lys Thr Asn Phe Lys Gly Leu Phe Ser Ile Glu Lys Lys
1               5                   10                  15

Phe Asn Val Asn Leu Leu Pro Ser Gln Leu Lys Leu Glu Asp Lys Ile
            20                  25                  30

Asn Ile Phe Trp Ala Thr Leu Met Arg Val Val Gly Trp Leu Leu Tyr
        35                  40                  45

Thr Leu Leu Ile Ala Ser Met Thr Glu Val Lys Asn Asn Ile Ile
    50                  55                  60

Ile Tyr Ile Ser Cys Ile Leu Ile Val Val Leu Leu Ile Phe Asp Ile
65                  70                  75                  80

Ser Ser Ile Phe Leu Ile Ser Asp Asp Met Arg Lys Lys Asn Tyr Arg
                85                  90                  95

Tyr Leu Phe Ile Lys Arg Asp Glu Glu Tyr Tyr Arg Leu Asp Lys Tyr
            100                 105                 110

Phe Tyr Asp Ile Ser Asp Lys Gln Val Leu Gln Tyr Thr Val Asn Glu
        115                 120                 125

Lys Asp Met Lys Ile Glu Lys Asn Asn Gly Asp Pro Lys Ile Asp Glu
    130                 135                 140

Lys Glu Lys Ile Val Gly Lys Lys Ile Val Thr Glu Lys Ile Asn Ser
145                 150                 155                 160

Asp Lys Val Asn Thr Phe Ile Gln Thr Asp Ser Glu Ala Thr Tyr Ser
                165                 170                 175

Ser Lys Tyr Ile Thr Leu Val Pro Ile Val Gln Asn Ile Ile Leu Ile
            180                 185                 190

Ile Ser Ile Ile Leu Thr Ala Cys Phe His Lys Leu Trp Ile Val Ile
        195                 200                 205

Leu Cys Leu Ile Ile Tyr Phe Leu Leu Asn Gly Ile Phe Thr Leu Arg
    210                 215                 220

Leu Ser Ser Asn Val Asn Glu Thr Leu Glu Asn Asn Ile Lys Gln
225                 230                 235                 240

Val Lys Asn Lys Val Lys Asn His Phe Asn Glu Asp Glu Asn Asp Asn
                245                 250                 255

Val Gly Asp Lys Lys Asp Ser Tyr Glu His Arg Asp Lys Asn Ile Asn
            260                 265                 270

Ile Ile Val Val Asn Glu Leu Lys Lys
        275             280
```

<210> SEQ ID NO 25
<211> LENGTH: 120
<212> TYPE: DNA
<213> ORGANISM: Staphylococcus epidermidis
<220> FEATURE:
<221> NAME/KEY: CDS
<222> LOCATION: (1)..(120)

<400> SEQUENCE: 25

```
gtg gct aca cca gtg ttt att gat agt gtt ggg gaa gaa gat gaa aag        48
Val Ala Thr Pro Val Phe Ile Asp Ser Val Gly Glu Glu Asp Glu Lys
1               5                   10                  15 aat gag aga gat tta gaa aag tta agt aaa cta tat cct aat gca gag        96
Asn Glu Arg Asp Leu Glu Lys Leu Ser Lys Leu Tyr Pro Asn Ala Glu
                20                  25                  30 ttt cac att gat gat att agg tag                                       120
Phe His Ile Asp Asp Ile Arg
            35

<210> SEQ ID NO 26
<211> LENGTH: 39
<212> TYPE: PRT
<213> ORGANISM: Staphylococcus epidermidis

<400> SEQUENCE: 26

Val Ala Thr Pro Val Phe Ile Asp Ser Val Gly Glu Glu Asp Glu Lys
1               5                   10                  15

Asn Glu Arg Asp Leu Glu Lys Leu Ser Lys Leu Tyr Pro Asn Ala Glu
                20                  25                  30

Phe His Ile Asp Asp Ile Arg
            35

<210> SEQ ID NO 27
<211> LENGTH: 657
<212> TYPE: DNA
<213> ORGANISM: Staphylococcus epidermidis
<220> FEATURE:
<221> NAME/KEY: CDS
<222> LOCATION: (1)..(657)

<400> SEQUENCE: 27 atg gct gtt gga tta ccg cct gca act gct tta ggt aca aat aaa tta        48
Met Ala Val Gly Leu Pro Pro Ala Thr Ala Leu Gly Thr Asn Lys Leu
1               5                   10                  15 gcg agt tct ttc gga tct ctt aca gct act atc tcc ttt att aga gca        96
Ala Ser Ser Phe Gly Ser Leu Thr Ala Thr Ile Ser Phe Ile Arg Ala
                20                  25                  30 aaa aaa gta aat att aaa ttg atg cct aaa ata ttc cct ttt gtt ttt       144
Lys Lys Val Asn Ile Lys Leu Met Pro Lys Ile Phe Pro Phe Val Phe
            35                  40                  45 ctt gct tct att att gga gct tat gtt gca act gta att cca gcg cga       192
Leu Ala Ser Ile Ile Gly Ala Tyr Val Ala Thr Val Ile Pro Ala Arg
        50                  55                  60 tat ttt aaa cct ttg gcg att ata atg ctt ttt ata gta ttg att tat       240
Tyr Phe Lys Pro Leu Ala Ile Ile Met Leu Phe Ile Val Leu Ile Tyr
65                  70                  75                  80 aca ctc ttt aaa aag gat tgg aac ggt aat aca cta ata aac gaa act       288
Thr Leu Phe Lys Lys Asp Trp Asn Gly Asn Thr Leu Ile Asn Glu Thr
                85                  90                  95 tct aaa tta aaa tta ttt att gtt ttt tcc cta cta ata tta att ggc       336
Ser Lys Leu Lys Leu Phe Ile Val Phe Ser Leu Leu Ile Leu Ile Gly
            100                 105                 110 ttc tat gat ggg ttt tta ggt gga gga aca ggt agt ttc ttt ata ttt       384
Phe Tyr Asp Gly Phe Leu Gly Gly Gly Thr Gly Ser Phe Phe Ile Phe
        115                 120                 125 gtt tta tta att tta gga tta gac ttt tta aaa tct gca gga aat gct       432
Val Leu Leu Ile Leu Gly Leu Asp Phe Leu Lys Ser Ala Gly Asn Ala
    130                 135                 140 aaa gtt tta aat ttt gga agt aat ata ggt gcc ctg ctt tta ttt ata       480
Lys Val Leu Asn Phe Gly Ser Asn Ile Gly Ala Leu Leu Leu Phe Ile
145                 150                 155                 160
```

```
tta tta aat aaa gta gat tat tta tta ggt ttc agt atg gct ttg tct    528
Leu Leu Asn Lys Val Asp Tyr Leu Leu Gly Phe Ser Met Ala Leu Ser
            165                 170                 175 atg att gtt gga agc tat att ggt agt tca ttc gca gta aaa aaa ggt    576
Met Ile Val Gly Ser Tyr Ile Gly Ser Ser Phe Ala Val Lys Lys Gly
            180                 185                 190 gtt tca tat gta aaa tta tta ttt ata att gtt act tta ctt ttg tta    624
Val Ser Tyr Val Lys Leu Leu Phe Ile Ile Val Thr Leu Leu Leu Leu
        195                 200                 205 ata aaa aac tta tat gat tat ata ttt cag taa                        657
Ile Lys Asn Leu Tyr Asp Tyr Ile Phe Gln
    210                 215
```

<210> SEQ ID NO 28
<211> LENGTH: 218
<212> TYPE: PRT
<213> ORGANISM: Staphylococcus epidermidis

<400> SEQUENCE: 28

```
Met Ala Val Gly Leu Pro Pro Ala Thr Ala Leu Gly Thr Asn Lys Leu
1               5                   10                  15

Ala Ser Ser Phe Gly Ser Leu Thr Ala Thr Ile Ser Phe Ile Arg Ala
            20                  25                  30

Lys Lys Val Asn Ile Lys Leu Met Pro Lys Ile Phe Pro Phe Val Phe
        35                  40                  45

Leu Ala Ser Ile Ile Gly Ala Tyr Val Ala Thr Val Ile Pro Ala Arg
    50                  55                  60

Tyr Phe Lys Pro Leu Ala Ile Ile Met Leu Phe Ile Val Leu Ile Tyr
65                  70                  75                  80

Thr Leu Phe Lys Lys Asp Trp Asn Gly Asn Thr Leu Ile Asn Glu Thr
                85                  90                  95

Ser Lys Leu Lys Leu Phe Ile Val Phe Ser Leu Leu Ile Leu Ile Gly
            100                 105                 110

Phe Tyr Asp Gly Phe Leu Gly Gly Gly Thr Gly Ser Phe Phe Ile Phe
        115                 120                 125

Val Leu Leu Ile Leu Gly Leu Asp Phe Leu Lys Ser Ala Gly Asn Ala
    130                 135                 140

Lys Val Leu Asn Phe Gly Ser Asn Ile Gly Ala Leu Leu Phe Ile
145                 150                 155                 160

Leu Leu Asn Lys Val Asp Tyr Leu Leu Gly Phe Ser Met Ala Leu Ser
                165                 170                 175

Met Ile Val Gly Ser Tyr Ile Gly Ser Ser Phe Ala Val Lys Lys Gly
            180                 185                 190

Val Ser Tyr Val Lys Leu Leu Phe Ile Ile Val Thr Leu Leu Leu Leu
        195                 200                 205

Ile Lys Asn Leu Tyr Asp Tyr Ile Phe Gln
    210                 215
```

<210> SEQ ID NO 29
<211> LENGTH: 144
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(144)

<400> SEQUENCE: 29

```
atg aaa tta cta gat gac aat aat ttt gac tta aaa cta cct att aac     48
Met Lys Leu Leu Asp Asp Asn Asn Phe Asp Leu Lys Leu Pro Ile Asn
1               5                   10                  15 tat aaa atc aat act gat aat tat aga tca ctt act caa gat aaa tta     96
Tyr Lys Ile Asn Thr Asp Asn Tyr Arg Ser Leu Thr Gln Asp Lys Leu
            20                  25                  30 gat gca tta agt tca tct gat gct aat ttt gat ggt att tgg gat tag    144
Asp Ala Leu Ser Ser Ser Asp Ala Asn Phe Asp Gly Ile Trp Asp
        35                  40                  45
```

<210> SEQ ID NO 30
<211> LENGTH: 47
<212> TYPE: PRT
<213> ORGANISM: Artificial Sequence
<220> FEATURE:
<223> OTHER INFORMATION: Synthetic Construct

<400> SEQUENCE: 30

```
Met Lys Leu Leu Asp Asp Asn Asn Phe Asp Leu Lys Leu Pro Ile Asn
1               5                   10                  15

Tyr Lys Ile Asn Thr Asp Asn Tyr Arg Ser Leu Thr Gln Asp Lys Leu
            20                  25                  30

Asp Ala Leu Ser Ser Ser Asp Ala Asn Phe Asp Gly Ile Trp Asp
        35                  40                  45
```

<210> SEQ ID NO 31
<211> LENGTH: 114
<212> TYPE: DNA
<213> ORGANISM: Staphylococcus epidermidis
<220> FEATURE:
<221> NAME/KEY: CDS
<222> LOCATION: (1)..(114)

<400> SEQUENCE: 31

```
atg aat ctt tta atc aga gaa ttg gaa aat cat tca aga gaa gtt gga     48
Met Asn Leu Leu Ile Arg Glu Leu Glu Asn His Ser Arg Glu Val Gly
1               5                   10                  15 ctc ata gca tat aat aaa gaa ata ttg caa aaa gta tgg agt att tta     96
Leu Ile Ala Tyr Asn Lys Glu Ile Leu Gln Lys Val Trp Ser Ile Leu
            20                  25                  30 agt gaa tac ata gtg taa                                            114
Ser Glu Tyr Ile Val
        35
```

<210> SEQ ID NO 32
<211> LENGTH: 37
<212> TYPE: PRT
<213> ORGANISM: Staphylococcus epidermidis

<400> SEQUENCE: 32

```
Met Asn Leu Leu Ile Arg Glu Leu Glu Asn His Ser Arg Glu Val Gly
1               5                   10                  15

Leu Ile Ala Tyr Asn Lys Glu Ile Leu Gln Lys Val Trp Ser Ile Leu
            20                  25                  30

Ser Glu Tyr Ile Val
        35
```

<210> SEQ ID NO 33
<211> LENGTH: 204
<212> TYPE: DNA
<213> ORGANISM: Staphylococcus epidermidis
<220> FEATURE:
<221> NAME/KEY: CDS

<222> LOCATION: (1)..(204)

<400> SEQUENCE: 33

```
ttg aga gat cca agc caa aca tta ttg att aaa aag tta aaa ggt ata        48
Leu Arg Asp Pro Ser Gln Thr Leu Leu Ile Lys Lys Leu Lys Gly Ile
1               5                   10                  15 tat ttc aag gct ttt cta act tca tca cca tat tct gga att aat gga        96
Tyr Phe Lys Ala Phe Leu Thr Ser Ser Pro Tyr Ser Gly Ile Asn Gly
                20                  25                  30 act aaa tta gtt gct ata ggt acg att aat ata aga aaa acc cca att       144
Thr Lys Leu Val Ala Ile Gly Thr Ile Asn Ile Arg Lys Thr Pro Ile
            35                  40                  45 gaa aat act aaa gaa gaa ctt ttt act aat aaa gta att aga aat aga       192
Glu Asn Thr Lys Glu Glu Leu Phe Thr Asn Lys Val Ile Arg Asn Arg
        50                  55                  60 aat aga cca taa                                                       204
Asn Arg Pro
65
```

<210> SEQ ID NO 34
<211> LENGTH: 67
<212> TYPE: PRT
<213> ORGANISM: Staphylococcus epidermidis

<400> SEQUENCE: 34

```
Leu Arg Asp Pro Ser Gln Thr Leu Leu Ile Lys Lys Leu Lys Gly Ile
1               5                   10                  15

Tyr Phe Lys Ala Phe Leu Thr Ser Ser Pro Tyr Ser Gly Ile Asn Gly
                20                  25                  30

Thr Lys Leu Val Ala Ile Gly Thr Ile Asn Ile Arg Lys Thr Pro Ile
            35                  40                  45

Glu Asn Thr Lys Glu Glu Leu Phe Thr Asn Lys Val Ile Arg Asn Arg
        50                  55                  60

Asn Arg Pro
65
```

<210> SEQ ID NO 35
<211> LENGTH: 1008
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(1008)

<400> SEQUENCE: 35

```
atg aaa aag atg tgg tta cca att ata act aca atc ata gta gct ata        48
Met Lys Lys Met Trp Leu Pro Ile Ile Thr Thr Ile Ile Val Ala Ile
1               5                   10                  15 att ata gta tta atc att tta aaa aag aca aat cat tta tat ttt aac        96
Ile Ile Val Leu Ile Ile Leu Lys Lys Thr Asn His Leu Tyr Phe Asn
                20                  25                  30 aac ttg gat aca tat aaa gtt tat aaa gtg gaa gat aga aaa gac att       144
Asn Leu Asp Thr Tyr Lys Val Tyr Lys Val Glu Asp Arg Lys Asp Ile
            35                  40                  45 tct ggt aag ggt atc gtt ttt cct gaa cat gtt aaa gtg tat aaa att       192
Ser Gly Lys Gly Ile Val Phe Pro Glu His Val Lys Val Tyr Lys Ile
        50                  55                  60 aat aaa aat ata gga gaa tat att aga cca caa att aaa gat ttt aga       240
Asn Lys Asn Ile Gly Glu Tyr Ile Arg Pro Gln Ile Lys Asp Phe Arg
65                  70                  75                  80
```

```
aaa gtg aaa aaa ggt act ccc ctt att tat tat gat act aat agt agc      288
Lys Val Lys Lys Gly Thr Pro Leu Ile Tyr Tyr Asp Thr Asn Ser Ser
                85                  90                  95 aac agg cct aat cta gtg gat aat att aat aac gtt aaa gaa gat tta      336
Asn Arg Pro Asn Leu Val Asp Asn Ile Asn Asn Val Lys Glu Asp Leu
            100                 105                 110 aat cgt gat tat caa aac gta gct aaa cac aat agc agt agt tat caa      384
Asn Arg Asp Tyr Gln Asn Val Ala Lys His Asn Ser Ser Ser Tyr Gln
        115                 120                 125 aag caa ata tct aat gat tac caa agg tta ttt aaa gct caa caa aaa      432
Lys Gln Ile Ser Asn Asp Tyr Gln Arg Leu Phe Lys Ala Gln Gln Lys
    130                 135                 140 tta aat cag cat gat aat ctg tct agt aaa gat ata tat gca gct ttt      480
Leu Asn Gln His Asp Asn Leu Ser Ser Lys Asp Ile Tyr Ala Ala Phe
145                 150                 155                 160 aat ggt gaa gtg aaa att agt aat tca att agc ggt aaa aat ggt gac      528
Asn Gly Glu Val Lys Ile Ser Asn Ser Ile Ser Gly Lys Asn Gly Asp
                165                 170                 175 gaa att tta aaa tta gtt tct aca aag tca gtt att aag atg aga gct      576
Glu Ile Leu Lys Leu Val Ser Thr Lys Ser Val Ile Lys Met Arg Ala
            180                 185                 190 tca caa tat ata gtt aat aag ata aaa aaa gga agt aac gtt aac ttt      624
Ser Gln Tyr Ile Val Asn Lys Ile Lys Lys Gly Ser Asn Val Asn Phe
        195                 200                 205 aaa tta gat agt gac agt gaa aat gta aaa ggt aag gtc cag tct att      672
Lys Leu Asp Ser Asp Ser Glu Asn Val Lys Gly Lys Val Gln Ser Ile
    210                 215                 220 gat aac tta cct ata aat atg aaa aaa gaa cgt tac tat aaa aac tat      720
Asp Asn Leu Pro Ile Asn Met Lys Lys Glu Arg Tyr Tyr Lys Asn Tyr
225                 230                 235                 240 gaa cct aaa tat atg att aca att tct gat tta aat cat ggt gtg aga      768
Glu Pro Lys Tyr Met Ile Thr Ile Ser Asp Leu Asn His Gly Val Arg
                245                 250                 255 gca gga ttt act ggg aaa gta acg att cct tat aat atg att gaa att      816
Ala Gly Phe Thr Gly Lys Val Thr Ile Pro Tyr Asn Met Ile Glu Ile
            260                 265                 270 cct caa aat agt atc att aat aaa aat tat gtt ttt ata gtt aat aag      864
Pro Gln Asn Ser Ile Ile Asn Lys Asn Tyr Val Phe Ile Val Asn Lys
        275                 280                 285 gat aat tat gta caa aaa cgt aga gtt aaa ata gta aag att aaa aat      912
Asp Asn Tyr Val Gln Lys Arg Arg Val Lys Ile Val Lys Ile Lys Asn
    290                 295                 300 aaa ctc att gct aag aaa gga tta aaa tta ggt gat cga gtc att gaa      960
Lys Leu Ile Ala Lys Lys Gly Leu Lys Leu Gly Asp Arg Val Ile Glu
305                 310                 315                 320 aaa cct aaa aga tct tta caa gaa gga caa caa att aat att aaa taa     1008
Lys Pro Lys Arg Ser Leu Gln Glu Gly Gln Gln Ile Asn Ile Lys
                325                 330                 335
```

<210> SEQ ID NO 36
<211> LENGTH: 335
<212> TYPE: PRT
<213> ORGANISM: Artificial Sequence
<220> FEATURE:
<223> OTHER INFORMATION: Synthetic Construct

<400> SEQUENCE: 36

```
Met Lys Lys Met Trp Leu Pro Ile Ile Thr Thr Ile Ile Val Ala Ile
1               5                   10                  15

Ile Ile Val Leu Ile Ile Leu Lys Lys Thr Asn His Leu Tyr Phe Asn
```

-continued

```
                    20                  25                  30
Asn Leu Asp Thr Tyr Lys Val Tyr Lys Val Glu Asp Arg Lys Asp Ile
             35                  40                  45

Ser Gly Lys Gly Ile Val Phe Pro Glu His Val Lys Val Tyr Lys Ile
 50                  55                  60

Asn Lys Asn Ile Gly Glu Tyr Ile Arg Pro Gln Ile Lys Asp Phe Arg
 65                  70                  75                  80

Lys Val Lys Lys Gly Thr Pro Leu Ile Tyr Tyr Asp Thr Asn Ser Ser
                 85                  90                  95

Asn Arg Pro Asn Leu Val Asp Asn Ile Asn Asn Val Lys Glu Asp Leu
            100                 105                 110

Asn Arg Asp Tyr Gln Asn Val Ala Lys His Asn Ser Ser Tyr Gln
            115                 120                 125

Lys Gln Ile Ser Asn Asp Tyr Gln Arg Leu Phe Lys Ala Gln Gln Lys
        130                 135                 140

Leu Asn Gln His Asp Asn Leu Ser Ser Lys Asp Ile Tyr Ala Ala Phe
145                 150                 155                 160

Asn Gly Glu Val Lys Ile Ser Asn Ser Ile Ser Gly Lys Asn Gly Asp
                165                 170                 175

Glu Ile Leu Lys Leu Val Ser Thr Lys Ser Val Ile Lys Met Arg Ala
            180                 185                 190

Ser Gln Tyr Ile Val Asn Lys Ile Lys Lys Gly Ser Asn Val Asn Phe
        195                 200                 205

Lys Leu Asp Ser Asp Ser Glu Asn Val Lys Gly Lys Val Gln Ser Ile
    210                 215                 220

Asp Asn Leu Pro Ile Asn Met Lys Lys Glu Arg Tyr Tyr Lys Asn Tyr
225                 230                 235                 240

Glu Pro Lys Tyr Met Ile Thr Ile Ser Asp Leu Asn His Gly Val Arg
                245                 250                 255

Ala Gly Phe Thr Gly Lys Val Thr Ile Pro Tyr Asn Met Ile Glu Ile
            260                 265                 270

Pro Gln Asn Ser Ile Ile Asn Lys Asn Tyr Val Phe Ile Val Asn Lys
        275                 280                 285

Asp Asn Tyr Val Gln Lys Arg Arg Val Lys Ile Val Lys Ile Lys Asn
    290                 295                 300

Lys Leu Ile Ala Lys Lys Gly Leu Lys Leu Gly Asp Arg Val Ile Glu
305                 310                 315                 320

Lys Pro Lys Arg Ser Leu Gln Glu Gly Gln Gln Ile Asn Ile Lys
                325                 330                 335

<210> SEQ ID NO 37
<211> LENGTH: 282
<212> TYPE: DNA
<213> ORGANISM: Staphylococcus epidermidis
<220> FEATURE:
<221> NAME/KEY: CDS
<222> LOCATION: (1)..(282)

<400> SEQUENCE: 37 gtg caa gaa act cat tac gaa ttt aat ata gat gat gaa tta aga aaa      48
Val Gln Glu Thr His Tyr Glu Phe Asn Ile Asp Asp Glu Leu Arg Lys
 1               5                  10                  15 cta ggt tta tta gtt gga ata tcc gaa gaa atg tac tac tgc tca att      96
Leu Gly Leu Leu Val Gly Ile Ser Glu Glu Met Tyr Tyr Cys Ser Ile
             20                  25                  30 agt cga ata tca aca ttg tat ctt gaa aac ttt gga act aaa tgg gta     144
```

```
                    Ser Arg Ile Ser Thr Leu Tyr Leu Glu Asn Phe Gly Thr Lys Trp Val
                                35                  40                  45 gca tgg cgt gaa act tat gat ttt aag aat gat aaa aga gta tcg cac          192
Ala Trp Arg Glu Thr Tyr Asp Phe Lys Asn Asp Lys Arg Val Ser His
 50                  55                  60 aga ata ata gca aat ggc agt ttt gaa tta gta gct gca aga act aaa          240
Arg Ile Ile Ala Asn Gly Ser Phe Glu Leu Val Ala Ala Arg Thr Lys
 65                  70                  75                  80 aac tat tta aac tac att aaa aga aag cag gga ata aaa tga                  282
Asn Tyr Leu Asn Tyr Ile Lys Arg Lys Gln Gly Ile Lys
                 85                  90

<210> SEQ ID NO 38
<211> LENGTH: 93
<212> TYPE: PRT
<213> ORGANISM: Staphylococcus epidermidis

<400> SEQUENCE: 38

Val Gln Glu Thr His Tyr Glu Phe Asn Ile Asp Asp Glu Leu Arg Lys
 1               5                  10                  15

Leu Gly Leu Leu Val Gly Ile Ser Glu Glu Met Tyr Tyr Cys Ser Ile
             20                  25                  30

Ser Arg Ile Ser Thr Leu Tyr Leu Glu Asn Phe Gly Thr Lys Trp Val
         35                  40                  45

Ala Trp Arg Glu Thr Tyr Asp Phe Lys Asn Asp Lys Arg Val Ser His
 50                  55                  60

Arg Ile Ile Ala Asn Gly Ser Phe Glu Leu Val Ala Ala Arg Thr Lys
 65                  70                  75                  80

Asn Tyr Leu Asn Tyr Ile Lys Arg Lys Gln Gly Ile Lys
                 85                  90

<210> SEQ ID NO 39
<211> LENGTH: 822
<212> TYPE: DNA
<213> ORGANISM: Staphylococcus saccharolyticus
<220> FEATURE:
<221> NAME/KEY: CDS
<222> LOCATION: (1)..(822)

<400> SEQUENCE: 39 atg aaa atg tac aat gca gca aag aat ctc ctt agt aaa gat gtg caa          48
Met Lys Met Tyr Asn Ala Ala Lys Asn Leu Leu Ser Lys Asp Val Gln
 1               5                  10                  15 gtt gta ccc tta aac gat aat aaa aag cca aca gta tca ttt aag aat          96
Val Val Pro Leu Asn Asp Asn Lys Lys Pro Thr Val Ser Phe Lys Asn
             20                  25                  30 ata act att gat gat gat ttt ata gat aac aat ttt tta gca tat gca          144
Ile Thr Ile Asp Asp Asp Phe Ile Asp Asn Asn Phe Leu Ala Tyr Ala
         35                  40                  45 aag aca aat gta tta ggt gtc cta act cgt ggt tta tgg tgt atc gac          192
Lys Thr Asn Val Leu Gly Val Leu Thr Arg Gly Leu Trp Cys Ile Asp
 50                  55                  60 att gat att aat cat gta aat ggt gaa agt ggc ttt gat agt ttg aaa          240
Ile Asp Ile Asn His Val Asn Gly Glu Ser Gly Phe Asp Ser Leu Lys
 65                  70                  75                  80 gac att cct tac tat gct gag ttt gtt tct aat gca caa aat acg cta          288
Asp Ile Pro Tyr Tyr Ala Glu Phe Val Ser Asn Ala Gln Asn Thr Leu
                 85                  90                  95 gtg cag aca aca gca agt ggg gga aag cat gta ata ttt aaa aaa cgt          336
Val Gln Thr Thr Ala Ser Gly Gly Lys His Val Ile Phe Lys Lys Arg
            100                 105                 110
```

```
gat ggt gtt gaa tac gct cag aaa ata gga tat tta cca tca gta gat      384
Asp Gly Val Glu Tyr Ala Gln Lys Ile Gly Tyr Leu Pro Ser Val Asp
            115                 120                 125 att aaa gca cat gat aat aac tat ttt gta tta gct gga agt aaa aca      432
Ile Lys Ala His Asp Asn Asn Tyr Phe Val Leu Ala Gly Ser Lys Thr
        130                 135                 140 gct aaa ggg cta tac act agt aat aag aaa cca gta atc act tat gat      480
Ala Lys Gly Leu Tyr Thr Ser Asn Lys Lys Pro Val Ile Thr Tyr Asp
145                 150                 155                 160 ggt gaa ttt gaa gat cgc att ttt tca aaa cgt gga aat tat cta caa      528
Gly Glu Phe Glu Asp Arg Ile Phe Ser Lys Arg Gly Asn Tyr Leu Gln
                165                 170                 175 cag act atg gaa aag ttc tca gta aaa agc gtg ttg cct aat cac aat      576
Gln Thr Met Glu Lys Phe Ser Val Lys Ser Val Leu Pro Asn His Asn
            180                 185                 190 ttt aat cat tta caa cat act ggc aaa ggt gga cta ggt aaa gag gca      624
Phe Asn His Leu Gln His Thr Gly Lys Gly Gly Leu Gly Lys Glu Ala
        195                 200                 205 tac aat cgt gta att aat ggt gaa agc ata gaa cgt aat aat gat gta      672
Tyr Asn Arg Val Ile Asn Gly Glu Ser Ile Glu Arg Asn Asn Asp Val
210                 215                 220 tat aaa gct att agt tac gct tta caa tgt aac gtg gat ata gag cct      720
Tyr Lys Ala Ile Ser Tyr Ala Leu Gln Cys Asn Val Asp Ile Glu Pro
225                 230                 235                 240 cta aaa gta att att ggt gat gtt aaa gca aat ggt gat gaa ttt act      768
Leu Lys Val Ile Ile Gly Asp Val Lys Ala Asn Gly Asp Glu Phe Thr
                245                 250                 255 tta gaa gag tgg gag gct tca tat aat agt gca aga aac tca tta cga      816
Leu Glu Glu Trp Glu Ala Ser Tyr Asn Ser Ala Arg Asn Ser Leu Arg
            260                 265                 270 att taa                                                              822
Ile

<210> SEQ ID NO 40
<211> LENGTH: 273
<212> TYPE: PRT
<213> ORGANISM: Staphylococcus saccharolyticus

<400> SEQUENCE: 40

Met Lys Met Tyr Asn Ala Ala Lys Asn Leu Leu Ser Lys Asp Val Gln
1               5                   10                  15

Val Val Pro Leu Asn Asp Asn Lys Lys Pro Thr Val Ser Phe Lys Asn
                20                  25                  30

Ile Thr Ile Asp Asp Asp Phe Ile Asp Asn Asn Phe Leu Ala Tyr Ala
            35                  40                  45

Lys Thr Asn Val Leu Gly Val Leu Thr Arg Gly Leu Trp Cys Ile Asp
        50                  55                  60

Ile Asp Ile Asn His Val Asn Gly Glu Ser Gly Phe Asp Ser Leu Lys
65                  70                  75                  80

Asp Ile Pro Tyr Tyr Ala Glu Phe Val Ser Asn Ala Gln Asn Thr Leu
                85                  90                  95

Val Gln Thr Thr Ala Ser Gly Gly Lys His Val Ile Phe Lys Lys Arg
            100                 105                 110

Asp Gly Val Glu Tyr Ala Gln Lys Ile Gly Tyr Leu Pro Ser Val Asp
        115                 120                 125

Ile Lys Ala His Asp Asn Asn Tyr Phe Val Leu Ala Gly Ser Lys Thr
    130                 135                 140
```

-continued

```
Ala Lys Gly Leu Tyr Thr Ser Asn Lys Lys Pro Val Ile Thr Tyr Asp
145                 150                 155                 160

Gly Glu Phe Glu Asp Arg Ile Phe Ser Lys Arg Gly Asn Tyr Leu Gln
                165                 170                 175

Gln Thr Met Glu Lys Phe Ser Val Lys Ser Val Leu Pro Asn His Asn
            180                 185                 190

Phe Asn His Leu Gln His Thr Gly Lys Gly Leu Gly Lys Glu Ala
        195                 200                 205

Tyr Asn Arg Val Ile Asn Gly Glu Ser Ile Glu Arg Asn Asn Asp Val
        210                 215                 220

Tyr Lys Ala Ile Ser Tyr Ala Leu Gln Cys Asn Val Asp Ile Glu Pro
225                 230                 235                 240

Leu Lys Val Ile Ile Gly Asp Val Lys Ala Asn Gly Asp Glu Phe Thr
                245                 250                 255

Leu Glu Glu Trp Glu Ala Ser Tyr Asn Ser Ala Arg Asn Ser Leu Arg
                260                 265                 270

Ile
```

<210> SEQ ID NO 41
<211> LENGTH: 1614
<212> TYPE: DNA
<213> ORGANISM: Staphylococcus saccharolyticus
<220> FEATURE:
<221> NAME/KEY: CDS
<222> LOCATION: (1)..(1614)

<400> SEQUENCE: 41

```
atg gac gaa gtt tct tta tat aaa aaa cat tat caa ttc cat tct aaa     48
Met Asp Glu Val Ser Leu Tyr Lys Lys His Tyr Gln Phe His Ser Lys
1               5                   10                  15 tta gat aat gtt gat aca cct aat tta tct cgt ata aaa gaa att agt     96
Leu Asp Asn Val Asp Thr Pro Asn Leu Ser Arg Ile Lys Glu Ile Ser
            20                  25                  30 aaa aga att tac ttt gct gca att aca aca gaa aaa caa att ttt aat    144
Lys Arg Ile Tyr Phe Ala Ala Ile Thr Thr Glu Lys Gln Ile Phe Asn
        35                  40                  45 aat aaa gga agt gtt tat cac caa aca aaa gat gaa ttt gca ggt gat    192
Asn Lys Gly Ser Val Tyr His Gln Thr Lys Asp Glu Phe Ala Gly Asp
    50                  55                  60 tac att aat aac ctt act tta gat tat acc ata aaa cct aga gaa ata    240
Tyr Ile Asn Asn Leu Thr Leu Asp Tyr Thr Ile Lys Pro Arg Glu Ile
65                  70                  75                  80 ggt gca gtc tat gga act atc tct gtt aaa aca aca gta gag aac ggt    288
Gly Ala Val Tyr Gly Thr Ile Ser Val Lys Thr Thr Val Glu Asn Gly
                85                  90                  95 gag gag aat aaa gag gca cat ttt aag cct agt aaa aca aat agc tat    336
Glu Glu Asn Lys Glu Ala His Phe Lys Pro Ser Lys Thr Asn Ser Tyr
            100                 105                 110 gca aag ttc att att gat cta att act gaa aaa gtc atc tac tca aaa    384
Ala Lys Phe Ile Ile Asp Leu Ile Thr Glu Lys Val Ile Tyr Ser Lys
        115                 120                 125 gag ttg gat agc ttt atc aaa tta aat agc aat caa tat gaa att ata    432
Glu Leu Asp Ser Phe Ile Lys Leu Asn Ser Asn Gln Tyr Glu Ile Ile
    130                 135                 140 gat aat act aat ttt tca tta gag tat ccg gta gac aat aag tat cat    480
Asp Asn Thr Asn Phe Ser Leu Glu Tyr Pro Val Asp Asn Lys Tyr His
145                 150                 155                 160 att aat gat ttt ctt gat gta atg cta gaa gtc tac aaa gag tat ttc    528
Ile Asn Asp Phe Leu Asp Val Met Leu Glu Val Tyr Lys Glu Tyr Phe
```

|  |  |  |  |  |  |  |  |  |  |  |  |  |  |  |  |
|---|---|---|---|---|---|---|---|---|---|---|---|---|---|---|---|
| att | aat | gat | tat | caa | tat | aat | att | tat | cct | tac | gct | ttc | gca | ggt | aat | 576 |
| Ile | Asn | Asp | Tyr | Gln | Tyr | Asn | Ile | Tyr | Pro | Tyr | Ala | Phe | Ala | Gly | Asn |  |
|  |  | 180 |  |  |  | 185 |  |  |  | 190 |  |  |  |  |  |  |
| gac | tgg | ata | tat | aat | tgc | aga | aaa | tta | gaa | ttt | gta | gat | aaa | aaa | att | 624 |
| Asp | Trp | Ile | Tyr | Asn | Cys | Arg | Lys | Leu | Glu | Phe | Val | Asp | Lys | Lys | Ile |  |
|  |  | 195 |  |  |  | 200 |  |  |  | 205 |  |  |  |  |  |  |
| act | agt | aac | gat | tac | tat | atc | atc | aaa | tat | gat | gta | gat | aag | aaa | aat | 672 |
| Thr | Ser | Asn | Asp | Tyr | Tyr | Ile | Ile | Lys | Tyr | Asp | Val | Asp | Lys | Lys | Asn |  |
|  | 210 |  |  |  |  | 215 |  |  |  |  | 220 |  |  |  |  |  |
| ata | aac | act | caa | tta | gca | caa | aaa | ttt | ttt | gac | tta | gta | agt | gac | aat | 720 |
| Ile | Asn | Thr | Gln | Leu | Ala | Gln | Lys | Phe | Phe | Asp | Leu | Val | Ser | Asp | Asn |  |
| 225 |  |  |  |  | 230 |  |  |  |  | 235 |  |  |  |  | 240 |  |
| gaa | cgc | agt | aag | aat | aat | tta | atg | ttg | gta | cac | gct | tat | act | atg | tat | 768 |
| Glu | Arg | Ser | Lys | Asn | Asn | Leu | Met | Leu | Val | His | Ala | Tyr | Thr | Met | Tyr |  |
|  |  |  |  | 245 |  |  |  |  | 250 |  |  |  |  | 255 |  |  |
| cga | aaa | atg | aaa | ctt | att | caa | gca | gaa | aaa | tgg | ttc | tta | atc | aaa | gac | 816 |
| Arg | Lys | Met | Lys | Leu | Ile | Gln | Ala | Glu | Lys | Trp | Phe | Leu | Ile | Lys | Asp |  |
|  |  |  | 260 |  |  |  |  | 265 |  |  |  |  | 270 |  |  |  |
| ttt | ggg | cga | tct | ggt | aaa | ggt | tta | ttt | atg | gaa | act | ttt | gaa | aaa | ctt | 864 |
| Phe | Gly | Arg | Ser | Gly | Lys | Gly | Leu | Phe | Met | Glu | Thr | Phe | Glu | Lys | Leu |  |
|  |  | 275 |  |  |  |  | 280 |  |  |  |  | 285 |  |  |  |  |
| cta | aat | gta | aac | aaa | gtc | aat | ttt | gat | agc | tta | tta | tca | tct | ggc | ttt | 912 |
| Leu | Asn | Val | Asn | Lys | Val | Asn | Phe | Asp | Ser | Leu | Leu | Ser | Ser | Gly | Phe |  |
| 290 |  |  |  |  | 295 |  |  |  |  | 300 |  |  |  |  |  |  |
| gag | gct | gca | aat | gaa | tgg | ctt | aac | ttt | tat | ggt | gca | gat | att | gct | cat | 960 |
| Glu | Ala | Ala | Asn | Glu | Trp | Leu | Asn | Phe | Tyr | Gly | Ala | Asp | Ile | Ala | His |  |
| 305 |  |  |  |  | 310 |  |  |  |  | 315 |  |  |  |  | 320 |  |
| gca | aat | gaa | aca | ggc | gaa | att | aat | aaa | ggt | atg | atg | aga | ata | tta | cgc | 1008 |
| Ala | Asn | Glu | Thr | Gly | Glu | Ile | Asn | Lys | Gly | Met | Met | Arg | Ile | Leu | Arg |  |
|  |  |  | 325 |  |  |  |  | 330 |  |  |  |  | 335 |  |  |  |
| aaa | ata | gct | act | ggt | gag | aat | att | tca | ggg | cgt | ggc | ata | caa | cga | aat | 1056 |
| Lys | Ile | Ala | Thr | Gly | Glu | Asn | Ile | Ser | Gly | Arg | Gly | Ile | Gln | Arg | Asn |  |
|  |  |  | 340 |  |  |  |  | 345 |  |  |  |  | 350 |  |  |  |
| aac | gtt | aag | ttt | aaa | aat | aat | gca | gta | tta | att | tta | gat | act | aat | gaa | 1104 |
| Asn | Val | Lys | Phe | Lys | Asn | Asn | Ala | Val | Leu | Ile | Leu | Asp | Thr | Asn | Glu |  |
|  |  | 355 |  |  |  |  | 360 |  |  |  |  | 365 |  |  |  |  |
| agt | gtt | gat | act | ggt | gaa | att | aca | gca | aat | aga | aca | cgt | aca | gtt | aaa | 1152 |
| Ser | Val | Asp | Thr | Gly | Glu | Ile | Thr | Ala | Asn | Arg | Thr | Arg | Thr | Val | Lys |  |
|  | 370 |  |  |  |  | 375 |  |  |  |  | 380 |  |  |  |  |  |
| atc | gca | ttt | aag | gat | aga | cca | aag | aat | gaa | act | gat | gaa | gaa | cgt | tat | 1200 |
| Ile | Ala | Phe | Lys | Asp | Arg | Pro | Lys | Asn | Glu | Thr | Asp | Glu | Glu | Arg | Tyr |  |
| 385 |  |  |  |  | 390 |  |  |  |  | 395 |  |  |  |  | 400 |  |
| caa | gta | ttt | aaa | cca | ttt | tgg | gac | ttt | gtt | aag | cct | aac | ggg | aaa | aac | 1248 |
| Gln | Val | Phe | Lys | Pro | Phe | Trp | Asp | Phe | Val | Lys | Pro | Asn | Gly | Lys | Asn |  |
|  |  |  | 405 |  |  |  |  | 410 |  |  |  |  | 415 |  |  |  |
| tca | gtc | aat | gcg | tca | gta | tca | ttt | tta | ata | tta | agt | ctt | gag | tat | ctt | 1296 |
| Ser | Val | Asn | Ala | Ser | Val | Ser | Phe | Leu | Ile | Leu | Ser | Leu | Glu | Tyr | Leu |  |
|  |  |  | 420 |  |  |  |  | 425 |  |  |  |  | 430 |  |  |  |
| aaa | caa | ata | ggc | aga | gaa | ttt | aag | ttc | aat | aac | gta | aca | ctt | aaa | aac | 1344 |
| Lys | Gln | Ile | Gly | Arg | Glu | Phe | Lys | Phe | Asn | Asn | Val | Thr | Leu | Lys | Asn |  |
|  |  | 435 |  |  |  |  | 440 |  |  |  |  | 445 |  |  |  |  |
| tat | tac | acc | gaa | gat | gaa | ttg | acg | gac | act | caa | att | ctt | atg | ctc | aaa | 1392 |
| Tyr | Tyr | Thr | Glu | Asp | Glu | Leu | Thr | Asp | Thr | Gln | Ile | Leu | Met | Leu | Lys |  |
| 450 |  |  |  |  | 455 |  |  |  |  | 460 |  |  |  |  |  |  |
| gtc | tta | gct | aaa | caa | gat | ttt | att | ttt | tca | ggt | gat | gag | ata | cta | caa | 1440 |
| Val | Leu | Ala | Lys | Gln | Asp | Phe | Ile | Phe | Ser | Gly | Asp | Glu | Ile | Leu | Gln |  |
| 465 |  |  |  |  | 470 |  |  |  |  | 475 |  |  |  |  | 480 |  |
| aaa | act | att | gaa | gaa | gat | tat | aaa | aat | ctg | aaa | tat | aaa | aaa | gca | aaa | 1488 |

```
Lys Thr Ile Glu Glu Asp Tyr Lys Asn Leu Lys Tyr Lys Lys Ala Lys
                    485                 490                 495 gaa gat atg aaa aaa ata gga gtg gct att aac caa cag gaa tgg ata      1536
Glu Asp Met Lys Lys Ile Gly Val Ala Ile Asn Gln Gln Glu Trp Ile
                500                 505                 510 gag gga caa aac act aaa gtt cat aaa gtg aaa aat caa gaa tta ttt      1584
Glu Gly Gln Asn Thr Lys Val His Lys Val Lys Asn Gln Glu Leu Phe
                515                 520                 525 aat atg gct tta gct ttg att gaa act tag                              1614
Asn Met Ala Leu Ala Leu Ile Glu Thr
                530                 535

<210> SEQ ID NO 42
<211> LENGTH: 537
<212> TYPE: PRT
<213> ORGANISM: Staphylococcus saccharolyticus

<400> SEQUENCE: 42

Met Asp Glu Val Ser Leu Tyr Lys Lys His Tyr Gln Phe His Ser Lys
1               5                   10                  15

Leu Asp Asn Val Asp Thr Pro Asn Leu Ser Arg Ile Lys Glu Ile Ser
                20                  25                  30

Lys Arg Ile Tyr Phe Ala Ala Ile Thr Thr Glu Lys Gln Ile Phe Asn
            35                  40                  45

Asn Lys Gly Ser Val Tyr His Gln Thr Lys Asp Glu Phe Ala Gly Asp
        50                  55                  60

Tyr Ile Asn Asn Leu Thr Leu Asp Tyr Thr Ile Lys Pro Arg Glu Ile
65                  70                  75                  80

Gly Ala Val Tyr Gly Thr Ile Ser Val Lys Thr Thr Val Glu Asn Gly
                85                  90                  95

Glu Glu Asn Lys Glu Ala His Phe Lys Pro Ser Lys Thr Asn Ser Tyr
            100                 105                 110

Ala Lys Phe Ile Ile Asp Leu Ile Thr Glu Lys Val Ile Tyr Ser Lys
        115                 120                 125

Glu Leu Asp Ser Phe Ile Lys Leu Asn Ser Asn Gln Tyr Glu Ile Ile
    130                 135                 140

Asp Asn Thr Asn Phe Ser Leu Glu Tyr Pro Val Asp Asn Lys Tyr His
145                 150                 155                 160

Ile Asn Asp Phe Leu Asp Val Met Leu Glu Val Tyr Lys Glu Tyr Phe
                165                 170                 175

Ile Asn Asp Tyr Gln Tyr Asn Ile Tyr Pro Tyr Ala Phe Ala Gly Asn
            180                 185                 190

Asp Trp Ile Tyr Asn Cys Arg Lys Leu Glu Phe Val Asp Lys Lys Ile
        195                 200                 205

Thr Ser Asn Asp Tyr Tyr Ile Ile Lys Tyr Asp Val Lys Lys Asn
    210                 215                 220

Ile Asn Thr Gln Leu Ala Gln Lys Phe Phe Asp Leu Val Ser Asp Asn
225                 230                 235                 240

Glu Arg Ser Lys Asn Asn Leu Met Leu Val His Ala Tyr Thr Met Tyr
                245                 250                 255

Arg Lys Met Lys Leu Ile Gln Ala Glu Lys Trp Phe Leu Ile Lys Asp
            260                 265                 270

Phe Gly Arg Ser Gly Lys Gly Leu Phe Met Glu Thr Phe Glu Lys Leu
        275                 280                 285

Leu Asn Val Asn Lys Val Asn Phe Asp Ser Leu Leu Ser Ser Gly Phe
    290                 295                 300
```

```
Glu Ala Ala Asn Glu Trp Leu Asn Phe Tyr Gly Ala Asp Ile Ala His
305                 310                 315                 320

Ala Asn Glu Thr Gly Glu Ile Asn Lys Gly Met Met Arg Ile Leu Arg
            325                 330                 335

Lys Ile Ala Thr Gly Glu Asn Ile Ser Gly Arg Gly Ile Gln Arg Asn
            340                 345                 350

Asn Val Lys Phe Lys Asn Asn Ala Val Leu Ile Leu Asp Thr Asn Glu
        355                 360                 365

Ser Val Asp Thr Gly Glu Ile Thr Ala Asn Arg Thr Arg Thr Val Lys
    370                 375                 380

Ile Ala Phe Lys Asp Arg Pro Lys Asn Glu Thr Asp Glu Glu Arg Tyr
385                 390                 395                 400

Gln Val Phe Lys Pro Phe Trp Asp Phe Val Lys Pro Asn Gly Lys Asn
                405                 410                 415

Ser Val Asn Ala Ser Val Ser Phe Leu Ile Leu Ser Leu Glu Tyr Leu
            420                 425                 430

Lys Gln Ile Gly Arg Glu Phe Lys Phe Asn Asn Val Thr Leu Lys Asn
        435                 440                 445

Tyr Tyr Thr Glu Asp Glu Leu Thr Asp Thr Gln Ile Leu Met Leu Lys
    450                 455                 460

Val Leu Ala Lys Gln Asp Phe Ile Phe Ser Gly Asp Glu Ile Leu Gln
465                 470                 475                 480

Lys Thr Ile Glu Glu Asp Tyr Lys Asn Leu Lys Tyr Lys Lys Ala Lys
                485                 490                 495

Glu Asp Met Lys Lys Ile Gly Val Ala Ile Asn Gln Gln Glu Trp Ile
            500                 505                 510

Glu Gly Gln Asn Thr Lys Val His Lys Val Lys Asn Gln Glu Leu Phe
        515                 520                 525

Asn Met Ala Leu Ala Leu Ile Glu Thr
    530                 535

<210> SEQ ID NO 43
<211> LENGTH: 144
<212> TYPE: DNA
<213> ORGANISM: Staphylococcus epidermidis
<220> FEATURE:
<221> NAME/KEY: CDS
<222> LOCATION: (1)..(144)

<400> SEQUENCE: 43 ttg ctt gat gaa gtt gtt att cta tat ttt tca ttt aat ggt ttt ata     48
Leu Leu Asp Glu Val Val Ile Leu Tyr Phe Ser Phe Asn Gly Phe Ile
1               5                   10                  15 ttt act gta aac gaa aca ata ctt tca ttc cca ctt tta tct gtg gct     96
Phe Thr Val Asn Glu Thr Ile Leu Ser Phe Pro Leu Leu Ser Val Ala
                20                  25                  30 tta act ttt aca att tta ttt gtg cta tta gtt aca tta gga gcc tga    144
Leu Thr Phe Thr Ile Leu Phe Val Leu Leu Val Thr Leu Gly Ala
            35                  40                  45

<210> SEQ ID NO 44
<211> LENGTH: 47
<212> TYPE: PRT
<213> ORGANISM: Staphylococcus epidermidis

<400> SEQUENCE: 44

Leu Leu Asp Glu Val Val Ile Leu Tyr Phe Ser Phe Asn Gly Phe Ile
1               5                   10                  15
```

Phe Thr Val Asn Glu Thr Ile Leu Ser Phe Pro Leu Leu Ser Val Ala
            20                  25                  30

Leu Thr Phe Thr Ile Leu Phe Val Leu Leu Val Thr Leu Gly Ala
        35                  40                  45

<210> SEQ ID NO 45
<211> LENGTH: 357
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(357)

<400> SEQUENCE: 45

| | |
|---|---:|
| atg aat aaa tta aat aac aaa gat tat aaa aat att gaa ggc aaa ttg<br>Met Asn Lys Leu Asn Asn Lys Asp Tyr Lys Asn Ile Glu Gly Lys Leu<br>1               5                   10                  15 | 48 |
| aat tac gat cat atc gta aat ggc aaa aag cac att aaa aaa atg agc<br>Asn Tyr Asp His Ile Val Asn Gly Lys Lys His Ile Lys Lys Met Ser<br>            20                  25                  30 | 96 |
| aaa cta tta caa aaa cgt cgt aac aaa gat att tca att att aaa aaa<br>Lys Leu Leu Gln Lys Arg Arg Asn Lys Asp Ile Ser Ile Ile Lys Lys<br>        35                  40                  45 | 144 |
| atg tac cct tat tta aat aat aat gaa att tta gaa atc act aat gat<br>Met Tyr Pro Tyr Leu Asn Asn Asn Glu Ile Leu Glu Ile Thr Asn Asp<br>    50                  55                  60 | 192 |
| tat caa gaa tac aaa aat ctt gtt caa gct act gaa act ttt aca gac<br>Tyr Gln Glu Tyr Lys Asn Leu Val Gln Ala Thr Glu Thr Phe Thr Asp<br>65                  70                  75                  80 | 240 |
| ttt cct agc att tac gaa ggt tct aat att agt aaa ttc tta act gaa<br>Phe Pro Ser Ile Tyr Glu Gly Ser Asn Ile Ser Lys Phe Leu Thr Glu<br>                85                  90                  95 | 288 |
| gat gat att gca gat tta aaa atg gct gtt gaa gaa atg cta gct ttt<br>Asp Asp Ile Ala Asp Leu Lys Met Ala Val Glu Glu Met Leu Ala Phe<br>            100                 105                 110 | 336 |
| gtt gaa aga ttg gag gag tag<br>Val Glu Arg Leu Glu Glu<br>        115 | 357 |

<210> SEQ ID NO 46
<211> LENGTH: 118
<212> TYPE: PRT
<213> ORGANISM: Artificial Sequence
<220> FEATURE:
<223> OTHER INFORMATION: Synthetic Construct

<400> SEQUENCE: 46

Met Asn Lys Leu Asn Asn Lys Asp Tyr Lys Asn Ile Glu Gly Lys Leu
1               5                   10                  15

Asn Tyr Asp His Ile Val Asn Gly Lys Lys His Ile Lys Lys Met Ser
            20                  25                  30

Lys Leu Leu Gln Lys Arg Arg Asn Lys Asp Ile Ser Ile Ile Lys Lys
        35                  40                  45

Met Tyr Pro Tyr Leu Asn Asn Asn Glu Ile Leu Glu Ile Thr Asn Asp
    50                  55                  60

Tyr Gln Glu Tyr Lys Asn Leu Val Gln Ala Thr Glu Thr Phe Thr Asp
65                  70                  75                  80

Phe Pro Ser Ile Tyr Glu Gly Ser Asn Ile Ser Lys Phe Leu Thr Glu
                85                  90                  95

```
Asp Asp Ile Ala Asp Leu Lys Met Ala Val Glu Glu Met Leu Ala Phe
            100                 105                 110
Val Glu Arg Leu Glu Glu
        115

<210> SEQ ID NO 47
<211> LENGTH: 750
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(750)

<400> SEQUENCE: 47 atg cta aac ttt gag tta aag aaa cac tta aaa gat aaa gat atg act      48
Met Leu Asn Phe Glu Leu Lys Lys His Leu Lys Asp Lys Asp Met Thr
1               5                   10                  15 att agt gaa tta agc gaa aaa act gga ata tca aga aat tct tta gga      96
Ile Ser Glu Leu Ser Glu Lys Thr Gly Ile Ser Arg Asn Ser Leu Gly
            20                  25                  30 tta tta ata aat gga aaa agt aga gga gtt caa ttt gaa aca ctt gaa     144
Leu Leu Ile Asn Gly Lys Ser Arg Gly Val Gln Phe Glu Thr Leu Glu
        35                  40                  45 aaa att tct aga gtt atg aat gta gat atc aaa aat tta ttt tca atg     192
Lys Ile Ser Arg Val Met Asn Val Asp Ile Lys Asn Leu Phe Ser Met
    50                  55                  60 act ttt gac ttt ata gaa ata tct gca aaa aat gaa aaa tta cgt agt     240
Thr Phe Asp Phe Ile Glu Ile Ser Ala Lys Asn Glu Lys Leu Arg Ser
65                  70                  75                  80 tct gaa gta gga gtt gat tac aat gcg tct tat gat ttt aaa caa tta     288
Ser Glu Val Gly Val Asp Tyr Asn Ala Ser Tyr Asp Phe Lys Gln Leu
                85                  90                  95 gtc tgt aat atg aat ata gat gga aca gaa tat gaa ttt tct gtt caa     336
Val Cys Asn Met Asn Ile Asp Gly Thr Glu Tyr Glu Phe Ser Val Gln
            100                 105                 110 tat gaa ata gat tta cag tta aac ata tta aaa gat cat agt tct gaa     384
Tyr Glu Ile Asp Leu Gln Leu Asn Ile Leu Lys Asp His Ser Ser Glu
        115                 120                 125 gtt aaa att act att gat tta aga aag ttt aac tac cta aat tta ttt     432
Val Lys Ile Thr Ile Asp Leu Arg Lys Phe Asn Tyr Leu Asn Leu Phe
    130                 135                 140 tta ccc atc aat tct gac gta gat aat gaa ata gca tat tta act cat     480
Leu Pro Ile Asn Ser Asp Val Asp Asn Glu Ile Ala Tyr Leu Thr His
145                 150                 155                 160 gtt tat ttt ata gac act ata ctc aaa atc aat aaa gat gaa att tta     528
Val Tyr Phe Ile Asp Thr Ile Leu Lys Ile Asn Lys Asp Glu Ile Leu
                165                 170                 175 gaa tta atg ggt aaa ggt ata aaa ata tct tca aat caa att tct tat     576
Glu Leu Met Gly Lys Gly Ile Lys Ile Ser Ser Asn Gln Ile Ser Tyr
            180                 185                 190 gta ata ata aaa gac gct ttt cac att att tca tct ggt att tta tat     624
Val Ile Ile Lys Asp Ala Phe His Ile Ile Ser Ser Gly Ile Leu Tyr
        195                 200                 205 atg aat aat ttc aag att aca caa aaa gag ttt tat gtt aat aaa ctc     672
Met Asn Asn Phe Lys Ile Thr Gln Lys Glu Phe Tyr Val Asn Lys Leu
    210                 215                 220 aaa act agt aat act ata aat tac atc gaa gac tcc aat aaa ata ctt     720
Lys Thr Ser Asn Thr Ile Asn Tyr Ile Glu Asp Ser Asn Lys Ile Leu
225                 230                 235                 240
```

```
ttt aca agc agg cat aaa aat gtt aca taa                              750
Phe Thr Ser Arg His Lys Asn Val Thr
                245
```

<210> SEQ ID NO 48
<211> LENGTH: 249
<212> TYPE: PRT
<213> ORGANISM: Artificial Sequence
<220> FEATURE:
<223> OTHER INFORMATION: Synthetic Construct

<400> SEQUENCE: 48

```
Met Leu Asn Phe Glu Leu Lys Lys His Leu Lys Asp Lys Asp Met Thr
1               5                   10                  15

Ile Ser Glu Leu Ser Glu Lys Thr Gly Ile Ser Arg Asn Ser Leu Gly
            20                  25                  30

Leu Leu Ile Asn Gly Lys Ser Arg Gly Val Gln Phe Glu Thr Leu Glu
        35                  40                  45

Lys Ile Ser Arg Val Met Asn Val Asp Ile Lys Asn Leu Phe Ser Met
50                  55                  60

Thr Phe Asp Phe Ile Glu Ile Ser Ala Lys Asn Glu Lys Leu Arg Ser
65                  70                  75                  80

Ser Glu Val Gly Val Asp Tyr Asn Ala Ser Tyr Asp Phe Lys Gln Leu
                85                  90                  95

Val Cys Asn Met Asn Ile Asp Gly Thr Glu Tyr Glu Phe Ser Val Gln
            100                 105                 110

Tyr Glu Ile Asp Leu Gln Leu Asn Ile Leu Lys Asp His Ser Ser Glu
        115                 120                 125

Val Lys Ile Thr Ile Asp Leu Arg Lys Phe Asn Tyr Leu Asn Leu Phe
130                 135                 140

Leu Pro Ile Asn Ser Asp Val Asp Asn Glu Ile Ala Tyr Leu Thr His
145                 150                 155                 160

Val Tyr Phe Ile Asp Thr Ile Leu Lys Ile Asn Lys Asp Glu Ile Leu
                165                 170                 175

Glu Leu Met Gly Lys Gly Ile Lys Ile Ser Ser Asn Gln Ile Ser Tyr
            180                 185                 190

Val Ile Ile Lys Asp Ala Phe His Ile Ile Ser Ser Gly Ile Leu Tyr
        195                 200                 205

Met Asn Asn Phe Lys Ile Thr Gln Lys Glu Phe Tyr Val Asn Lys Leu
210                 215                 220

Lys Thr Ser Asn Thr Ile Asn Tyr Ile Glu Asp Ser Asn Lys Ile Leu
225                 230                 235                 240

Phe Thr Ser Arg His Lys Asn Val Thr
                245
```

<210> SEQ ID NO 49
<211> LENGTH: 600
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(600)

<400> SEQUENCE: 49

```
ttg tcg att tta att agt ttt ctt agt tta att tta tca act ttc gct    48
Leu Ser Ile Leu Ile Ser Phe Leu Ser Leu Ile Leu Ser Thr Phe Ala
1               5                   10                  15
```

```
ttt tta tat gcg aac aaa aga cat aag ttg aat atg tta gat cat tta        96
Phe Leu Tyr Ala Asn Lys Arg His Lys Leu Asn Met Leu Asp His Leu
            20                  25                  30 gat gat aaa tca gaa tgg aga aaa aaa cta ttt gaa att gca ggt tct       144
Asp Asp Lys Ser Glu Trp Arg Lys Lys Leu Phe Glu Ile Ala Gly Ser
        35                  40                  45 tca aaa att gga atg gga aat tta tat caa ttt aga gct gca tta aga       192
Ser Lys Ile Gly Met Gly Asn Leu Tyr Gln Phe Arg Ala Ala Leu Arg
    50                  55                  60 ttc aca tac aaa aat gaa gat gaa tat tat gaa tat aat tat ttt gag       240
Phe Thr Tyr Lys Asn Glu Asp Glu Tyr Tyr Glu Tyr Asn Tyr Phe Glu
65                  70                  75                  80 tgc atg aac ata att att ata aaa tat tgt gaa aaa tta ata agt caa       288
Cys Met Asn Ile Ile Ile Ile Lys Tyr Cys Glu Lys Leu Ile Ser Gln
                85                  90                  95 aat cga ata gaa gat cac aaa cac aac gaa aac gaa aag gat caa tct       336
Asn Arg Ile Glu Asp His Lys His Asn Glu Asn Glu Lys Asp Gln Ser
            100                 105                 110 tat tta aaa aat tat gaa atg gat tca att aga tta ttt tgt att tac       384
Tyr Leu Lys Asn Tyr Glu Met Asp Ser Ile Arg Leu Phe Cys Ile Tyr
        115                 120                 125 atg tta gca gat cat tgg gaa aaa aaa caa aac aaa aat ttt aaa ttt       432
Met Leu Ala Asp His Trp Glu Lys Lys Gln Asn Lys Asn Phe Lys Phe
    130                 135                 140 aac aat cca gta aaa gaa gta gaa tta tgt ata gac acc tta caa aaa       480
Asn Asn Pro Val Lys Glu Val Glu Leu Cys Ile Asp Thr Leu Gln Lys
145                 150                 155                 160 ttt ctc aat att aat gat aaa aac tat tgt tat aaa tgc cat aaa agt       528
Phe Leu Asn Ile Asn Asp Lys Asn Tyr Cys Tyr Lys Cys His Lys Ser
                165                 170                 175 aaa tta aat aga gat aat ttt tac tgt ttg tat cac caa agt ata agt       576
Lys Leu Asn Arg Asp Asn Phe Tyr Cys Leu Tyr His Gln Ser Ile Ser
            180                 185                 190 ttg ata aat tct atg aca tcc taa                                       600
Leu Ile Asn Ser Met Thr Ser
        195
```

<210> SEQ ID NO 50
<211> LENGTH: 199
<212> TYPE: PRT
<213> ORGANISM: Artificial Sequence
<220> FEATURE:
<223> OTHER INFORMATION: Synthetic Construct

<400> SEQUENCE: 50

```
Leu Ser Ile Leu Ile Ser Phe Leu Ser Leu Ile Leu Ser Thr Phe Ala
1               5                   10                  15

Phe Leu Tyr Ala Asn Lys Arg His Lys Leu Asn Met Leu Asp His Leu
            20                  25                  30

Asp Asp Lys Ser Glu Trp Arg Lys Lys Leu Phe Glu Ile Ala Gly Ser
        35                  40                  45

Ser Lys Ile Gly Met Gly Asn Leu Tyr Gln Phe Arg Ala Ala Leu Arg
    50                  55                  60

Phe Thr Tyr Lys Asn Glu Asp Glu Tyr Tyr Glu Tyr Asn Tyr Phe Glu
65                  70                  75                  80

Cys Met Asn Ile Ile Ile Ile Lys Tyr Cys Glu Lys Leu Ile Ser Gln
                85                  90                  95

Asn Arg Ile Glu Asp His Lys His Asn Glu Asn Glu Lys Asp Gln Ser
            100                 105                 110
```

```
Tyr Leu Lys Asn Tyr Glu Met Asp Ser Ile Arg Leu Phe Cys Ile Tyr
        115                 120                 125

Met Leu Ala Asp His Trp Glu Lys Lys Gln Asn Lys Asn Phe Lys Phe
        130                 135                 140

Asn Asn Pro Val Lys Glu Val Glu Leu Cys Ile Asp Thr Leu Gln Lys
145                 150                 155                 160

Phe Leu Asn Ile Asn Asp Lys Asn Tyr Cys Tyr Lys Cys His Lys Ser
                165                 170                 175

Lys Leu Asn Arg Asp Asn Phe Tyr Cys Leu Tyr His Gln Ser Ile Ser
                180                 185                 190

Leu Ile Asn Ser Met Thr Ser
            195

<210> SEQ ID NO 51
<211> LENGTH: 435
<212> TYPE: DNA
<213> ORGANISM: Staphylococcus epidermidis
<220> FEATURE:
<221> NAME/KEY: CDS
<222> LOCATION: (1)..(435)

<400> SEQUENCE: 51
```

| | | |
|---|---|---|
| atg ggc tgt acg act gct gat att tta gcc tgt ttt aat cct aat cta<br>Met Gly Cys Thr Thr Ala Asp Ile Leu Ala Cys Phe Asn Pro Asn Leu<br>1                  5                      10                15 | | 48 |
| tat att ttt tta aga ttt gta tgc gca tta tct aac tct aaa cgc tca<br>Tyr Ile Phe Leu Arg Phe Val Cys Ala Leu Ser Asn Ser Lys Arg Ser<br>                  20                    25                    30 | | 96 |
| gta tta gat act tta act aaa cgc att tcg gta agc act cta cct aat<br>Val Leu Asp Thr Leu Thr Lys Arg Ile Ser Val Ser Thr Leu Pro Asn<br>           35                    40                    45 | | 144 |
| aat cca ctg aag ttc gca att tca gat tgc gta ttg gta gat att ttt<br>Asn Pro Leu Lys Phe Ala Ile Ser Asp Cys Val Leu Val Asp Ile Phe<br>        50                    55                    60 | | 192 |
| tgc atc aca cgt ccc aga gga acg atg att aaa ata aat aca gga ata<br>Cys Ile Thr Arg Pro Arg Gly Thr Met Ile Lys Ile Asn Thr Gly Ile<br>65                  70                    75                    80 | | 240 |
| gta ata aat gtt aat aaa gtt aat ttc caa tcc atg ata aat agc atg<br>Val Ile Asn Val Asn Lys Val Asn Phe Gln Ser Met Ile Asn Ser Met<br>                  85                    90                    95 | | 288 |
| act aat gaa cct act aac gtt aaa aca gaa ggc aat aaa tta ggt agc<br>Thr Asn Glu Pro Thr Asn Val Lys Thr Glu Gly Asn Lys Leu Gly Ser<br>                     100                105                110 | | 336 |
| ttt tgt gaa ata aat tca tta atc act ttt gta tca tct gtt aga cga<br>Phe Cys Glu Ile Asn Ser Leu Ile Thr Phe Val Ser Ser Val Arg Arg<br>           115                    120                    125 | | 384 |
| ctc att aat tgg cca ctt tca ttt tta tca aag aac ggc att ttt aat<br>Leu Ile Asn Trp Pro Leu Ser Phe Leu Ser Lys Asn Gly Ile Phe Asn<br>        130                    135                    140 | | 432 |
| tga | | 435 |

```
<210> SEQ ID NO 52
<211> LENGTH: 144
<212> TYPE: PRT
<213> ORGANISM: Staphylococcus epidermidis

<400> SEQUENCE: 52

Met Gly Cys Thr Thr Ala Asp Ile Leu Ala Cys Phe Asn Pro Asn Leu
1               5                   10                  15
```

```
Tyr Ile Phe Leu Arg Phe Val Cys Ala Leu Ser Asn Ser Lys Arg Ser
                20                  25                  30

Val Leu Asp Thr Leu Thr Lys Arg Ile Ser Val Ser Thr Leu Pro Asn
            35                  40                  45

Asn Pro Leu Lys Phe Ala Ile Ser Asp Cys Val Leu Val Asp Ile Phe
        50                  55                  60

Cys Ile Thr Arg Pro Arg Gly Thr Met Ile Lys Ile Asn Thr Gly Ile
65                  70                  75                  80

Val Ile Asn Val Asn Lys Val Asn Phe Gln Ser Met Ile Asn Ser Met
                85                  90                  95

Thr Asn Glu Pro Thr Asn Val Lys Thr Glu Gly Asn Lys Leu Gly Ser
            100                 105                 110

Phe Cys Glu Ile Asn Ser Leu Ile Thr Phe Val Ser Ser Val Arg Arg
        115                 120                 125

Leu Ile Asn Trp Pro Leu Ser Phe Leu Ser Lys Asn Gly Ile Phe Asn
130                 135                 140
```

```
<210> SEQ ID NO 53
<211> LENGTH: 120
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(120)

<400> SEQUENCE: 53 atg att cta tgg aag aaa tat ggg agc tat gaa atg caa att gca ttt      48
Met Ile Leu Trp Lys Lys Tyr Gly Ser Tyr Glu Met Gln Ile Ala Phe
1               5                   10                  15 aaa gat ttc aat gaa gat aag caa act att aat gag tat act cat ttt      96
Lys Asp Phe Asn Glu Asp Lys Gln Thr Ile Asn Glu Tyr Thr His Phe
            20                  25                  30 tta gtt cag aaa gaa cta cat tga                                     120
Leu Val Gln Lys Glu Leu His
        35
```

```
<210> SEQ ID NO 54
<211> LENGTH: 39
<212> TYPE: PRT
<213> ORGANISM: Artificial Sequence
<220> FEATURE:
<223> OTHER INFORMATION: Synthetic Construct

<400> SEQUENCE: 54

Met Ile Leu Trp Lys Lys Tyr Gly Ser Tyr Glu Met Gln Ile Ala Phe
1               5                   10                  15

Lys Asp Phe Asn Glu Asp Lys Gln Thr Ile Asn Glu Tyr Thr His Phe
            20                  25                  30

Leu Val Gln Lys Glu Leu His
        35
```

```
<210> SEQ ID NO 55
<211> LENGTH: 270
<212> TYPE: DNA
<213> ORGANISM: Artificial Sequence
<220> FEATURE:
<223> OTHER INFORMATION: Hypothetical protein coding sequence
<220> FEATURE:
<221> NAME/KEY: CDS
<222> LOCATION: (1)..(270)
```

<400> SEQUENCE: 55

```
atg gat gat tat aac tct aat aat gat acg aat gat tgg cat gaa atc    48
Met Asp Asp Tyr Asn Ser Asn Asn Asp Thr Asn Asp Trp His Glu Ile
1               5                   10                  15 att gaa cag ctg aag aac gat aac gag ata ctc aaa tct aac aat caa    96
Ile Glu Gln Leu Lys Asn Asp Asn Glu Ile Leu Lys Ser Asn Asn Gln
            20                  25                  30 gaa ctt cag caa cat att cat cag ctg gaa gac gag ata gac cca atg    144
Glu Leu Gln Gln His Ile His Gln Leu Glu Asp Glu Ile Asp Pro Met
        35                  40                  45 aga caa gaa aat gat gtt ttt cat cat tta tta caa cat ttt gat agt    192
Arg Gln Glu Asn Asp Val Phe His His Leu Leu Gln His Phe Asp Ser
50                  55                  60 aca gca ttt atg aac ttc aat aca tat cgt gat gat cgc cca tta aaa    240
Thr Ala Phe Met Asn Phe Asn Thr Tyr Arg Asp Asp Arg Pro Leu Lys
65                  70                  75                  80 aat gcg att aaa cga ttg aaa gaa caa taa                            270
Asn Ala Ile Lys Arg Leu Lys Glu Gln
                85
```

<210> SEQ ID NO 56
<211> LENGTH: 89
<212> TYPE: PRT
<213> ORGANISM: Artificial Sequence
<220> FEATURE:
<223> OTHER INFORMATION: Synthetic Construct

<400> SEQUENCE: 56

Met Asp Asp Tyr Asn Ser Asn Asn Asp Thr Asn Asp Trp His Glu Ile
1               5                   10                  15

Ile Glu Gln Leu Lys Asn Asp Asn Glu Ile Leu Lys Ser Asn Asn Gln
            20                  25                  30

Glu Leu Gln Gln His Ile His Gln Leu Glu Asp Glu Ile Asp Pro Met
        35                  40                  45

Arg Gln Glu Asn Asp Val Phe His His Leu Leu Gln His Phe Asp Ser
50                  55                  60

Thr Ala Phe Met Asn Phe Asn Thr Tyr Arg Asp Asp Arg Pro Leu Lys
65                  70                  75                  80

Asn Ala Ile Lys Arg Leu Lys Glu Gln
                85

<210> SEQ ID NO 57
<211> LENGTH: 18
<212> TYPE: DNA
<213> ORGANISM: Artificial Sequence
<220> FEATURE:
<223> OTHER INFORMATION: Primer sequence

<400> SEQUENCE: 57
cgcgcgaaga ccggttac                                                18

<210> SEQ ID NO 58
<211> LENGTH: 25
<212> TYPE: DNA
<213> ORGANISM: Artificial Sequence
<220> FEATURE:
<223> OTHER INFORMATION: Partial template strand
<220> FEATURE:
<221> NAME/KEY: misc_feature
<222> LOCATION: (7)..(7)
<223> OTHER INFORMATION: N is T or G

```
<400> SEQUENCE: 58
ggcggcngta accggtcttc gcgcg                    25
```

COMPOSITIONS AND METHOD OF TREATING CANCER

CROSS REFERENCE TO RELATED APPLICATIONS

This application is a divisional of U.S. application Ser. No. 16/497,430, filed Sep. 24, 2019, which is a U.S. National Stage Application filed under 35 U.S.C. § 371 and claims priority to International Application No. PCT/US2018/024511, filed Mar. 27, 2018, which claims priority under 35 U.S.C. § 119 from Provisional Application Ser. No. 62/477,370, filed Mar. 27, 2017, and from Provisional Application Ser. No. 62/638,058, filed Mar. 2, 2018, the disclosures of which are incorporated herein by reference.

STATEMENT REGARDING FEDERALLY SPONSORED RESEARCH

This invention was made with Government support under Grant No. AI083358, awarded by the National Institutes of Health. The Government has certain rights in the invention.

TECHNICAL FIELD

The disclosure relates to anti-cancer agents, methods of making, and methods of use thereof.

INCORPORATION BY REFERENCE OF SEQUENCE LISTING

Accompanying this filing is a Sequence Listing entitled "Sequence_ST25.txt", created on Jan. 18, 2022 and having 98,329 bytes of data, machine formatted on IBM-PC, MS-Windows operating system. The sequence listing is hereby incorporated herein by reference in its entirety for all purposes.

MICROORGANISM DEPOSIT

Exemplary microorganisms of the disclosure (*Staphylococcus epidermidis* MO34 and *Staphylococcus epidermidis* MO38) were deposited on Mar. 22, 2018 with the American Type Culture Collection, 10801 University Boulevard, Manassas, Va. 20110-2209, as ATCC Number PTA-125026 (strain designation S.epi-MO38 UCSD 20180315) and as ATCC Number PTA-125025 (strain designation S.epi-MO34 UCSD 20180315) under the Budapest Treaty. This deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

BACKGROUND

It is estimated that in 2017 there will be over 1.5 million new cancer cases diagnosed and greater than 600,000 cancer deaths in the U.S. Although advances have been made to treat and prevent various cancers, new methods and compositions are need.

SUMMARY

The disclosure provides compositions and methods useful for the treatment of neoplasias and cancers.

In a particular embodiment, the disclosure provides for a compound having the general formula of Formula I(a):

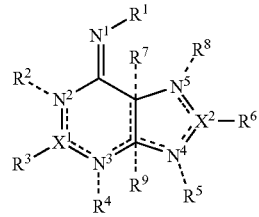

Formula I(a)

or a pharmaceutically acceptable salt or prodrug thereof, wherein, $N^1$-$N^5$ are nitrogen atoms; $X^1$-$X^2$ are carbon atoms; the R groups attached by a dashed line are present, or are not present if the R group is connected to an atom that is bound to another atom by a double covalent bond; the bond indicated by both a straight line and a dashed line indicate that the bond may be a single covalent bond or a double covalent bond; the fused heterocyclic ring system comprises three double bonds with $N^2$ or $N^3$ forming a double bond and with $X^1$, and with $N^4$ or $N^5$ forming a double bond with $X^2$; $R^1$ is a hydroxyl, ester, carboxylic acid, or —O—$R^{10}$; $R^2$, $R^4$, $R^5$, $R^7$-$R^9$ are independently a H, D, optionally substituted ($C_1$-$C_6$)-alkyl, optionally substituted ($C_1$-$C_6$)-alkenyl, optionally substituted ($C_1$-$C_6$)-alkynyl, optionally substituted ($C_3$-$C_{12}$)cycloalkyl, optionally substituted ($C_4$-$C_{12}$) cycloalkenyl, optionally substituted aryl; $R^3$ and $R^6$ are independently selected from a H, D, optionally substituted ($C_1$-$C_6$)-alkyl, optionally substituted ($C_1$-$C_6$)-heteroalkyl, optionally substituted ($C_1$-$C_6$)-alkenyl, optionally substituted ($C_1$-$C_6$)-heteroalkenyl, optionally substituted ($C_1$-$C_6$)-alkynyl, optionally substituted ($C_1$-$C_6$)-heteroalkynyl, optionally substituted ($C_3$-$C_{12}$)cycloalkyl, optionally substituted ($C_4$-$C_{12}$)cycloalkenyl, optionally substituted aryl, optionally substituted heterocycle, halide, hydroxyl, carbonyl, aldehyde, carboxyl, ester, alkoxy, carboxyamide, amine, imine, azide, cyano, nitro, nitroso, thiol, sulfide, sulfoxide, sulfone, and phosphate; $R^{10}$ is selected from D, optionally substituted ($C_1$-$C_6$)-alkyl, optionally substituted ($C_1$-$C_6$)-heteroalkyl, optionally substituted ($C_1$-$C_6$)-alkenyl, optionally substituted ($C_1$-$C_6$)-heteroalkenyl, optionally substituted ($C_1$-$C_6$)-alkynyl, optionally substituted ($C_1$-$C_6$)-heteroalkynyl, optionally substituted ($C_3$-$C_{12}$)cycloalkyl, optionally substituted ($C_4$-$C_{12}$)cycloalkenyl, optionally substituted aryl, and optionally substituted heterocycle.

In another embodiment, the disclosure provides a compound having the general formula of Formula I(b):

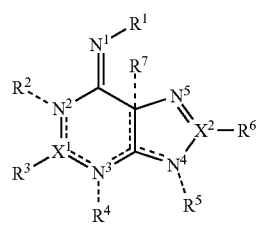

Formula I(b)

or a pharmaceutically acceptable salt or prodrug thereof, wherein, $N^1$-$N^5$ are nitrogen atoms; $X^1$-$X^2$ are carbon atoms; the R groups attached by a dashed line are present, or are not present if the R group is connected to an atom that is bound to another atom by a double covalent bond; the bond indicated by both a straight line and a dashed line indicate that the bond may be a single covalent bond or a double covalent bond; the fused heterocyclic ring system comprises three double bonds with $N^2$ or $N^3$ forming a double bond with $X^1$, and with $N^4$ or $N^5$ forming a double bond with $X^2$; $R^1$ is a hydroxyl, ester, carboxylic acid, or —O—$R^{10}$; $R^2$, $R^4$, $R^5$, and $R^7$ are independently a H, D, optionally substituted ($C_1$-$C_6$)-alkyl, optionally substituted ($C_1$-$C_6$)-alkenyl, optionally substituted ($C_1$-$C_6$)-alkynyl, optionally substituted ($C_3$-$C_{12}$)cycloalkyl, optionally substituted ($C_4$-$C_{12}$) cycloalkenyl, optionally substituted aryl; $R^{10}$ is selected from D, optionally substituted ($C_1$-$C_6$)-alkyl, optionally substituted ($C_1$-$C_6$)-heteroalkyl, optionally substituted ($C_1$-$C_6$)-alkenyl, optionally substituted ($C_1$-$C_6$)-heteroalkenyl, optionally substituted ($C_1$-$C_6$)-alkynyl, optionally substituted ($C_1$-$C_6$)-heteroalkynyl, optionally substituted ($C_3$-$C_{12}$) cycloalkyl, optionally substituted ($C_4$-$C_{12}$)cycloalkenyl, optionally substituted aryl, and optionally substituted heterocycle.

In yet another embodiment, the disclosure provides a compound of general formula II (6-N-hydroxyaminopurine (6-HAP)):

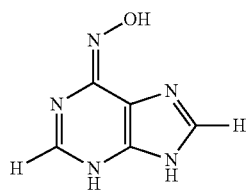

Formula II or a pharmaceutically acceptable salt or prodrug thereof; or a tautomer of the compound of Formula II, or a pharmaceutically acceptable salt or prodrug of the tautomer of compound of Formula II thereof.

In another embodiment, the disclosure provides a pharmaceutical composition comprising a compound of formula I(a), I(b) and/or II and a pharmaceutically acceptable carrier. In yet another embodiment, the pharmaceutical composition comprises at least one additional active agent. In still a further embodiment, the at least one additional active agent is a chemotherapeutic agent. If still a further embodiment, the chemotherapeutic agent is selected from the group consisting of an alkylating agent, an antimetabolite, an anti-microtubule agent, a topoisomerase inhibitor, and a cytotoxic antibiotic. In a further embodiment, the anticancer agent is selected from the group consisting of cisplatin (CDDP), carboplatin, procarbazine, mechlorethamine, cyclophosphamide, camptothecin, ifosfamide, melphalan, chlorambucil, busulfan, nitrosourea, dactinomycin, daunorubicin, doxorubicin, bleomycin, plicamycin, mitomycin, etoposide (VP16), tamoxifen, raloxifene, estrogen receptor binding agents, docetaxel, paclitaxel, gemcitabine, navelbine, farnesyl-protein transferase inhibitors, transplatinum, 5-fluorouracil, vincristine, vinblastine, 6-mercaptopurine; capecitabine; cladribine; clorfarabine; cytarabine; doxorubicin; fludarabine; floxuridine; gemcitabine; hydroxyurea; methotrexate; pemetrexed; pentostatin; prednisone; procarbazineand methotrexate, or any analog or derivative variant thereof.

The disclosure also provides a method of treating a neoplasm (including precancerous), cell proliferative disorder or cancer comprising contacting a subject topically or parenterally with a compound or pharmaceutical composition containing the compound of Formula I(a), I(b) and/or II in an amount effective to treat the neoplasm, cancer or cell proliferative disorder.

S. epidermidis produces 6-HAP, which was found to inhibit DNA synthesis and has the potential to convey protection against neoplasia. A beneficial role for skin bacteria in host defense is consistent with observations of a role for commensal bacteria to resist S. aureus infection, but further extends this concept to host defense functions against cancer and pre-cancerous neoplasms, e.g., papillomas and actinic keratosis). Moreover, a loss of S. epidermidis strains that produce 6-HAP may increase a subject's risk for developing skin cancer. As such the disclosure provides for probiotic compositions which comprise an S. epidermidis strains that produces 6-HAP for preventing, attenuating and/or inhibiting neoplasia in a subject.

In a particular embodiment, the disclosure provides for a composition that protects a subject from skin cancer or other type of neoplasia, comprising (i) a composition of formula I, II or II and/or (ii) a probiotic commensal microorganism that produces 6-N-hydroxyaminopurine (6-HAP). In a further embodiment, the probiotic commensal microorganism is a strain of Staphylococcus epidermis. In yet a further embodiment, the strain is one or more of Staphylococcus epidermis is Staphylococcus epidermis MO34 and/or Staphylococcus epidermis MO38. In another embodiment, the composition is formulated for topical or dermal delivery. In yet another embodiment, the composition is in the form of a lotion, shake lotion, cream, ointment, gel, foam, powder, solid, paste or tincture. In a further embodiment, the composition further comprises one or more sunscreen agents. Examples of sunscreen agents include, but are not limited to, aminobenzoic acid, avobenzone, cinoxate, dioxybenzone, ecamsule, ensulizole, homosalate, meradimate, octocrylene, octinoxate, octisalate, oxybenzone, padimate 0, sulisobenzone, titanium dioxide, trolamine salicylate, and zinc oxide. In yet a further embodiment, the skin protectant composition further comprises one or more topical antibiotics. Examples of topical antibiotics include, but are not limited to, sulfacetamide sodium, bacitracin, polymyxin b, erythromycin, silver sulfadiazine, neomycin, retapamulin, and mupirocin.

In a certain embodiment, the disclosure further provides for a method of preventing a subject from developing skin cancer or other type of neoplasia, comprising topically administering to the subject a composition of the disclosure. In a further embodiment, the neoplasia is an epithelial neoplasia. In yet a further embodiment, the neoplasia is induced by or from UV exposure.

BRIEF DESCRIPTION OF THE DRAWINGS

FIG. 8A-D shows Productions of 6-HAP by skin isolate strains and laboratory strains of *S. epidermidis*. (a-d) MO34 (a) and MO38 (b) strains of *S. epidermidis* isolated from the surface of normal human skin, or ATCC12228 (c) and ATCC1457 (d) laboratory strains were cultured overnight in TSB. 6-HAP was partially purified from culture supernatant according to the Method section. Left panel shows a HPLC-elution profile of 6-HAP (Arrow) on a TSKgel NH2-100 amino column (4.6×150 mm) (Tosoh Biosci. LLC, Tokyo, Japan) after Sep-Pak step (See method). The elution profile was monitored at 270 nm. Green line represents a gradient of $H_2O$ in acetonitrile. The right panel represents antimicrobial activity of each fraction on radial diffusion assay against GAS.

DETAILED DESCRIPTION

Figure 1A:
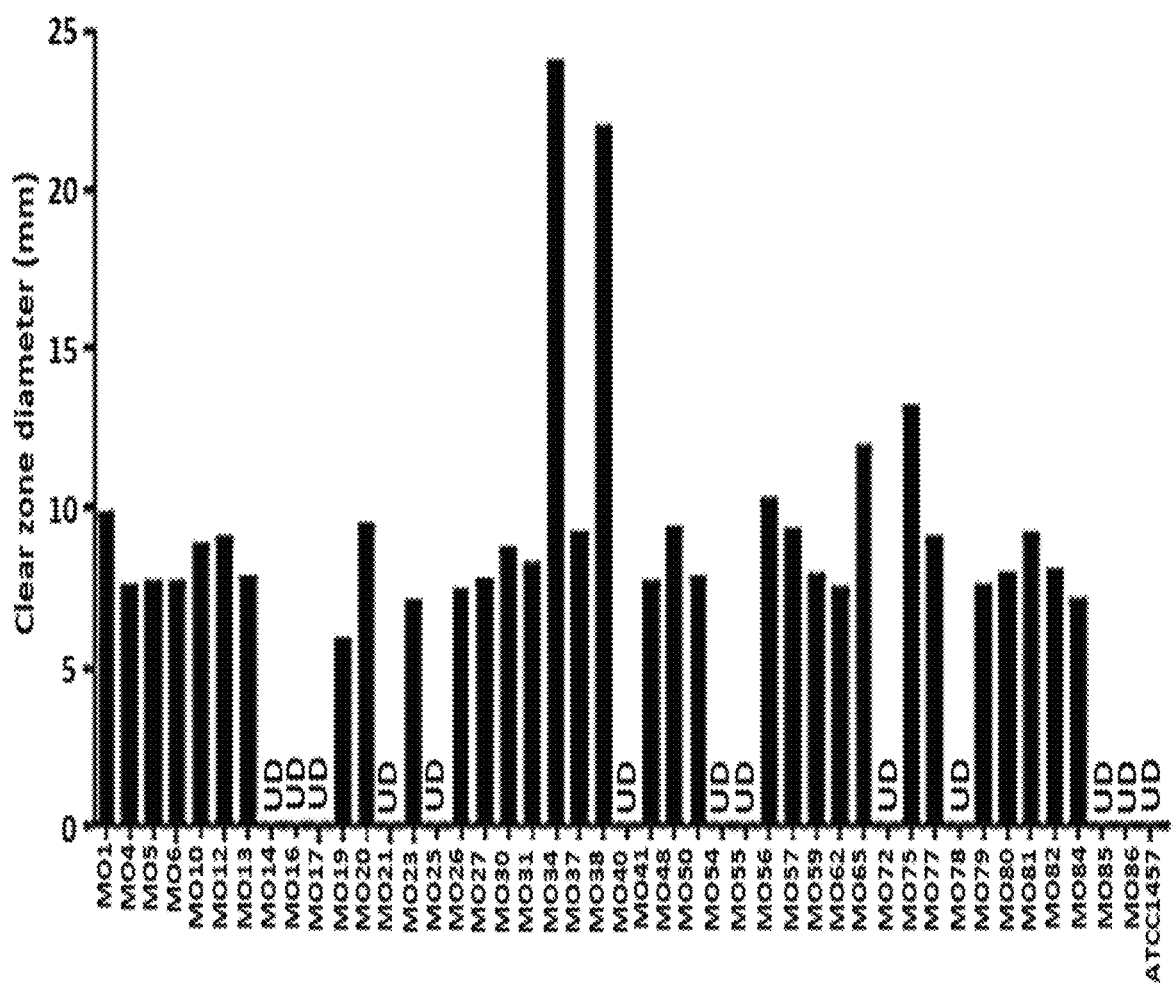
FIG. 1A-D shows S. epidermidis strains isolated from normal human skin produce non-proteinaceous molecule with antimicrobial activity. (a) Screening for antimicrobial activity of culture supernatant from 44 strains of S. epidermidis strains isolated from normal human skin by radial diffusion assay against group A streptococcus (GAS). Data represent diameter of growth inhibition zone of conditioned media of each strain. UD=undetectable. (b) Elution profile of the antimicrobial compound purified from culture supernatant of S. epidermidis MO34 by HPLC using a PolyHYDROXYMETHYL. The last step of 5 purification steps is shown. The insert panel represents antimicrobial activity of each fraction on radial diffusion assay against GAS. Green line represents a gradient of $H_2O$ in acetonitrile. (c-d) Stability of antimicrobial molecules from S. epidermidis producing the strongest antibiotic activity (MO34) against GAS after heat-treatment (100° C. for indicated time) (c) and incubation with proteinase K (2 mg/mL) or papain (2 mg/mL) at 37° C. for 3 hrs, followed by 5-min incubation at 90° C. to inactivate enzyme (d). Antimicrobial activity against GAS was determined by radial diffusion assay.

As used herein and in the appended claims, the singular forms "a," "an," and "the" include plural referents unless the context clearly dictates otherwise. Thus, for example, reference to "a compound" includes a plurality of such compounds and reference to "the cell" includes reference to one or more cells and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. However, with respect to any similar or identical terms found in both the incorporated publications or references and those expressly put forth or defined in this application, then those terms definitions or meanings expressly put forth in this application shall control in all respects. The publications discussed above and throughout the text are provided solely for their disclosure prior to the filing date of the present application. Nothing herein is to be construed as an admission that the inventors are not entitled to antedate such disclosure by virtue of prior disclosure.

The term "alkyl", refers to an organic group that is comprised of carbon and hydrogen atoms that contains single covalent bonds between the carbons. Generally, an "alkyl" as used in this disclosure, refers to an organic group that contains 1 to 20 carbon atoms, unless stated otherwise. Wherein if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Specific substituted alkyl groups include haloalkyl groups, particularly trihalomethyl groups and specifically trifluoromethyl groups.

The term "alkenyl", refers to an organic group that is comprised of carbon and hydrogen atoms that contains at least one double covalent bond between two carbons. Generally, an "alkenyl" as used in this disclosure, refers to organic group that contains 1 to 20 carbon atoms, unless stated otherwise. While a $C_1$-alkenyl can form a double bond to an atom of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise. Substituted alkenyl groups include among others those which are substituted with alkyl or aryl groups, which groups in turn can be optionally substituted. Specific alkenyl groups include ethenyl, prop-1-enyl, prop-2-enyl, but-1- enyl, but-2-enyl, pent-1-enyl, pent-2-enyl, branched pentenyl, hex-1-enyl, branched hexenyl, all of which are optionally substituted.

The term "alkynyl", refers to an organic group that is comprised of carbon and hydrogen atoms that contains a triple covalent bond between two carbons. Generally, an "alkynyl" as used in this disclosure, refers to organic group that contains 1 to 20 carbon atoms, unless stated otherwise. While a $C_1$-alkynyl can form a triple bond to an atom of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "antimicrobial" as it relates to treatments, agents, and compounds refers to an agent that can be used to suppress, attenuate, ameliorate, any symptom caused by or resulting from an infection by a foreign agent. For the purposes of this disclosure a foreign agent includes, but is not limited to, bacteria, parasites, viruses, and fungi.

The term "anticancer" as it relates to treatments, agents, and compounds refers to an agent (e.g., small molecule such as 6-HAP or a probiotic) that can be used to suppress, attenuate, ameliorate, any symptom caused by or resulting from a cell proliferative disorder, neoplasm or cancer.

The term "aryl", as used in this disclosure, refers to a conjugated planar ring system with delocalized pi electron clouds that contain only carbon as ring atoms. An "aryl" for the purposes of this disclosure encompass from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof. Substituted aryl groups include among others those which are substituted with alkyl or alkenyl groups, which groups in turn can be optionally substituted. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups. Specific aryl groups include phenyl groups, biphenyl groups, and naphthyl groups, all of which are optionally substituted.

For purposes of the disclosure the term "cancer" will be used to encompass cell proliferative disorders, neoplasms, precancerous cell disorders and cancers. Thus, a "cancer" refers to any cell that undergoes aberrant cell proliferation that can lead to metastasis or tumor growth. Exemplary cancers include but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some embodiments, the cancer is selected from the group consisting of melanoma, colorectal cancer, pancreatic cancer, bladder cancer, breast cancer, triple negative breast cancer, ovarian cancer and lung cancer.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 7 cycloalkyl rings, wherein when the cycloalkyl is greater than 1 ring, then the cycloalkyl rings are joined so that they are linked, fused, or a combination thereof. A "cycloalkyl" can also include bicyclic and tricyclic-based groups. A cycloalkyl may be substituted or unsubstituted, or in the case of more than one cycloalkyl ring, one or more rings may be unsubstituted, one or more rings may be substituted, or a combination thereof.

The term "cycloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 7 cycloalkenyl rings, wherein when the cycloalkenyl is greater than 1 ring, then the cycloalkenyl rings are joined so that they are linked, fused, or a combination thereof. "Cycloalkenyl" can include bicyclic and tricyclic-based groups. A cycloalkenyl may be substituted or unsubstituted, or in the case of more than one cycloalkenyl ring, one or more rings may be unsubstituted, one or more rings may be substituted, or a combination thereof. Specific alkenyl groups include cycloprop-1-enyl, cyclobut-1-enyl, cyclobut-2-enyl, cyclopent-1-enyl, cyclohexenyl, all of which are optionally substituted.

The term "heterocycle", as used in this disclosure, refers to ring structures that contain at least 1 noncarbon ring atom. A "heterocycle" for the purposes of this disclosure encompass from 1 to 7 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "heterocyclyl" used alone or as a suffix or prefix, refers a monovalent radical derived from a heterocycle by removing a hydrogen therefrom. Heterocyclyl includes, for example, monocyclic heterocyclyls, such as, aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl. In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include, but are not limited to, quinuclidinyl, diazabicyclo[2.2.1]heptyl; and 7-oxabicyclo[2.2.1]heptyl.

The term "hetero-aryl" used alone or as a suffix or prefix, refers to a heterocycle or heterocyclyl having aromatic character. Examples of heteroaryls include, but are not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain.

Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

As used herein, the term "Probiotic Composition" includes a composition comprising a probiotic commensal skin bacteria of the disclosure and may optionally include compounds described as Formula I or II, that affects the microbiome balance of the human skin and which can inhibit cancer growth, invasion and/or metastasis and which can affect pathogen spread and proliferation. A probiotic composition can comprise an unnatural ratio or composition of an agent or microbe found in nature. For example, a microbial probiotic composition can comprise a single type of organism found on the skin (e.g., *S. epidermidis* MO34 or MO38 or MO34 and MO38) at a cell density or amount not normally found in nature. Alternatively, or in addition, the microbial probiotic composition can include a single type of organism as mentioned above, but which is present in a composition that does not occur in nature such as a salve, lotion, suspension, ointment and the like. In still another embodiment, a microbial probiotic composition can comprise a microbe at a density not normally found in nature or mixed with a non-naturally occurring composition at a density not found in nature. In still another embodiment, a microbial probiotic composition can comprise a recombinantly engineered microorganism (e.g., an attenuated bacterial species). In one embodiment, commensal skin bacteria is a bacteria that produces 6-HAP. In another or further embodiment, the bacteria comprises *S. epidermidis* MO34 and/or MO38.

The term "purified" and "substantially purified" as used herein refers to cultures, or co-cultures of microorganisms or of biological agent (e.g. fermentation media and extracts, fractionated fermentation media, fermentation by-products, compounds of Formula I or II etc.) that is substantially free of other cells or components found in the natural environment with which an in vivo-produced agent would naturally be associated. In some embodiments, a co-culture probiotic can comprise one or a plurality of commensal skin bacteria.

The term "substituted" with respect to hydrocarbons, heterocycles, and the like, refers to structures wherein the parent chain contains one or more substituents. For example, optionally substituted hydrocarbons, hetero-hydrocarbons, heterocycles, mixed ring systems, and the like, can include substitution with one or more of the following substituents: halogens, CN, —COOR, —OR, —COR, —OCOOR, —CON(R)$_2$, —OCON(R)$_2$, —N(R)$_2$, NO$_2$, —SR, —SO$_2$R, —SO$_2$N(R)$_2$ or —SOR groups, wherein R is selected from the group comprising a hydrocarbon, a hetero-hydrocarbon, heterocycle, and mixed ring system. Optional substitution of alkyl groups includes substitution with one or more alkenyl groups, aryl groups or both, wherein the alkenyl groups or aryl groups are also optionally substituted. Optional substitution of alkenyl groups includes substitution with one or more alkyl groups, aryl groups, or both, wherein the alkyl groups or aryl groups are also optionally substituted. Optional substitution of aryl groups includes substitution of the aryl ring with one or more alkyl groups, alkenyl groups, or both, wherein the alkyl groups or alkenyl groups are also optionally substituted.

The term "substituent" refers to an atom or group of atoms substituted in place of a hydrogen atom. For purposes of this disclosure, a substituent would include deuterium atoms.

Optional substituents for hydrocarbons, hetero-hydrocarbons, heterocycles, mixed ring systems, and the like, include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl groups and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds;
- —SR, —SO$_2$R, or —SOR where R is an alkyl group or an aryl groups and more specifically where R is methyl, ethyl, propyl, butyl, phenyl groups all of which are optionally substituted; for example —SR, R can be hydrogen;
- —OCOOR where R is an alkyl group or an aryl groups;
- —SO$_2$N(R)$_2$ where R is a hydrogen, an alkyl group, or an aryl group and R and R can form a ring; and
- —OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, the term "Topical" can include administration to the skin externally, as well as shallow injection (e.g., intradermally and intralesionally as described in the Examples) such that a topical probiotic composition described herein comes in direct contact with skin.

The term "unsubstituted" with respect to hydrocarbons, heterocycles, and the like, refers to structures wherein the parent chain contains no substituents.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

A bond indicated by a straight line and a dashed line indicates that the bond may be a single covalent bond or alternatively a double covalent bond. But in the case where a ring atom's maximum valence would be exceeded by forming a double covalent bond with another ring atom, then the bond would be a single covalent bond.

For the purposes of this disclosure, in the instance that a ring atom designated as X would exceed its maximum valence by binding a group designated by R, then the group designated by R would be absent.

Mammalian skin harbors diverse microbial communities whose growth is influenced by ecological factors on the body surface such as humidity, temperature, pH, lipid content, and the presence of antimicrobials produced by the host. Although the specific mechanisms through which skin surface microbes influence host function are incompletely understood, specific strains of coagulase-negative staphylococcal species have been shown to produce proteins that work together with endogenous host antimicrobial peptides (AMPs) to provide direct protection against infectious pathogens. For example, the production of phenol-soluble modulins (PSMg and PSMd) by S. epidermidis can selectively kill bacterial pathogens such as S. aureus and group A Streptococcus (GAS). This species has also been shown to benefit skin immune function by diminishing inflammation after injury, enhancing development of cutaneous T cells and promoting expression of host AMPs such as cathelicidins and b-defensins. Germ-free mice are more susceptible to skin infection than mice maintained under specific pathogen-free conditions or mono associated with S. epidermidis.

Further evidence that commensal Staphylococcus species provide host defense has come from observations that nasal colonization with either a specific strain of S. epidermidis that produces a serine protease or a strain of Staphylococcus lugdunensis that produces a thiazolidine containing cyclic peptide can inhibit nasal colonization by S. aureus. More recently, several strains of S. epidermidis, S. hominis, and other coagulase-negative staphylococcal species that produce a variety of previously unknown AMPs were found to be deficient in atopic dermatitis patients colonized by S. aureus, and a clinical trial evaluating the effect of reintroduction of these strains demonstrated that they directly reduced S. aureus colonization on humans. Thus, evidence is increasing that the skin microbiome has an important role in promoting host defense.

These observations suggest that the skin microbiome may contribute to aspects of host defense. The disclosure describes the molecular analysis of the metabolic products of human skin commensal bacteria. Unexpectedly it was found that S. epidermidis strain MO34 and MO38 produce a nucleobase analog with the capacity to inhibit DNA synthesis. When administered intravenously or topically applied to mice, this molecule or the live S. epidermidis strain(s) itself suppressed tumor growth in vivo.

The disclosure provides a composition for treating cancer and/or a pathogen infection comprising a compound of formula I(a), I(b) and/or II, alone or in combination with (e.g., produced by) a commensal probiotic composition comprising an S. epidermidis strain that produces a compound of the disclosure. In one embodiment, the disclosure provides a method and composition comprising 6-HAP. In one embodiment, the composition and method comprise a probiotic commensal bacterial the produces 6-HAP. In another embodiment, the composition and method comprise a substantially purified 6-HAP or analog or derivative thereof. In another or further embodiment, the composition comprising 6-HAP comprises a commensal probiotic and a purified 6-HAP or analog or derivative thereof.

The disclosure demonstrates that compounds comprising a structure of Formula I(a), Formula I(b) and/or Formula II have the ability to inhibit replication and expression of DNA. For example, the disclosure demonstrates that a compound for Formula II (6-HAP) has important and unique host defense capabilities. 6-HAP suppressed growth of major skin pathogens such as GAS, GBS, S. aureus (including MRSA) and P. aeruginosa. Importantly, this antimicrobial activity was selective for these skin pathogens over human skin commensals such as S. epidermidis, S. hominis and P. acnes. Thus, the disclosure provides methods and compositions useful for treating infections by contacting a pathogen with a compound of Formula I(a), I(b) and/or II alone or in combination with a probiotic commensal bacterial of the disclosure.

In addition, an unexpected discovery was made while studying the mechanism of action of 6-HAP that led to the identification that this molecule also has selective anti-proliferative function against mammalian tumor cell lines and UV-induced skin tumor. As described elsewhere herein, the 6-HAP compound or derivatives thereof (e.g., Formula I(a), and I(b)) as well as probiotic commensal bacterial of the disclosure that can produce 6-HAP can be used to treat neoplasm and cancer.

The disclosure demonstrates that 6-HAP did not exert activity through disruption of cell membranes. 6-HAP directly inhibited adenine-thymidine base pair matching in a cell free assay. Thus, the mechanism of action of 6-HAP is through inhibition of DNA synthesis. In 6-HAP, the amino group at the carbon C-6 position of the purine ring is replaced with a hydroxyamino group. This is a critical position for DNA synthesis since the hydrogen of the amino group at the carbon C-6 position of adenine is required to bind with oxygen at the carbon C-4 position of thymine.

Commensal skin microbes have not previously been shown to produce nucleobase analogs with such activity. However, the capacity of other chemically-synthesized nucleobase analogs to inhibit DNA synthesis is known. For example, 6-mercaptopurine is converted in vivo to 6-thioguanine and is then incorporated into DNA in place of guanine. 8-Azaguanine also suppresses DNA synthesis by a similar mechanism. Similarly to 6-HAP, 6-thioguanine and 8-azaguanine have both antibiotic and antineoplastic activities. It is highly unlikely that a common commensal produces a potent mutagen that would not be previously detected. However, if this was indeed the case, the current observations would remain highly significant since this would identify a previously undetected risk factor for cancer. Thus, this observation of the capacity of a commensal skin microbe to produce a nucleobase analog is highly significant.

A remarkable quality of 6-HAP as a nucleobase analog is the capacity to exert selective activity against pathogenic bacteria and tumor cell lines, but little toxicity to commensals or normal cells. Previously identified AMPs from S. epidermidis or S. hominis were also known to exert selective killing, a logical behavior if the host cell is to resist killing itself. The mechanism responsible for selective killing by these AMPs is poorly understood but thought to be due to differences in the capacity to disrupt the cell membrane. In the case of 6-HAP, only some pathogens and cancer cell lines were inhibited in vitro and in vivo. No systemic toxicity of 6-HAP was observed when mice were repeatedly administrated this intravenously, nor were growth of normal keratinocytes inhibited by high concentrations of 6-HAP in culture. In contrast, the DNA synthesis inhibitor mitomycin C did not show such selective effects on cell growth. The evidence therefore suggest that the selectivity by 6-HAP is not simply due to the rate of cell division. 6-HAP exhibits no toxicity to a wild-type strain of *E. coli*, whereas it inhibited growth of mutant strains deficient in genes involved in molybdenum cofactors. The data herein demonstrate that the molybdoenzyme mARC2 protected NHEKs from 6-HAP. In addition, relative expression level of mARC2 was higher in NHEKs than cancer cell lines. Moreover, the disclosure demonstrates the involvement of molybdoenzymes that may be capable of detoxifying 6-HAP to enable selective activity. Thus, in one embodiment, the disclosure provides a method of treating an infection or cancer, wherein the pathogen of the infection or the cancer cell has mARC2 expression at a level that is less than normal healthy cells of the subject, the method comprising administering a probiotic of the disclosure and/or a compound of formula I(a), I(b) and/or II to the pathogen or cancer cell.

The disclosure thus provides an entirely new concept that some members of our skin microbiome may suppress tumor growth and UV-induced tumor formation. Most prior observations have reported that dysbiosis (a state of altered microbiome) can promote cancer. Observations associating bacteria in the gut with an increase in carcinogenesis suggested this effect was dependent on inflammation. Intestinal inflammation has also been reported to promote development of tumors through increasing the capacity of microbiota to produce genotoxins which elicit DNA damage.

The importance of this disclosure are several fold. The selective activity of 6-HAP may be essential for maintaining homeostasis of the skin microbiome and could be exploited therapeutically to treat *S. aureus* infection or colonization, which plays important role in pathogenesis of atopic dermatitis, as well as in treating cancer progression or skin damage leading to cancer. Such a strategy for defense is theoretically superior to the use of existing pharmaceutical antibiotics or antiseptics that non-specifically kill beneficial commensal bacteria and disrupt homeostasis by killing the normal microflora. In addition, long-lasting protection could be achieved if the applied beneficial bacteria could successfully colonize on the skin surface. Further, the disclosure shows the surprising presence of anti-neoplastic activity from *S. epidermidis*. The observation that a bacterial product can directly limit tumor growth suggests a paradigm shift in the understanding of the functions of the human skin microbiome.

The disclosure thus provides a method of treating or reducing the risk of skin infection and/or cancer (e.g., skin cancer) by promoting an effective skin biome comprising *S. epidermidis* that produces 6-HAP. The disclosure also provides a method of treating or reducing the risk of infection and/or skin cancer comprising administering a probiotic comprising *S. epidermidis* that produces an anticancer agent of the disclosure. In one embodiment, the probiotic composition comprises *S. epidermidis* MO34 and/or MO38 or attenuated or genetically engineered strains thereof.

The disclosure provides a probiotic composition for inhibiting and/or modulating skin damage and neoplasms, more particularly of the skin, and preferably human skin. In particular embodiment, the probiotic composition of the disclosure comprises a commensal strain of *Staphylococcus epidermidis* that protects against skin neoplasia by producing the compound 6-N-hydroxyaminopurine (6-HAP). In one embodiment, the strain is *S. epidermidis* MO34 and/or MO38.

The probiotic compositions of the disclosure can be used to treat neoplastic diseases and disorders, improve healing and reduce morbidity associated with skin damage and neoplasms as well as treating infection through the antimicrobial activity of 6-HAP. For example, a topical probiotic compositions can be used to treat a skin damage caused by UV irradiation by contacting the skin with a therapeutically effective amount or inhibitive effective amount of a composition as described below and herein. The composition can comprise one or more of an *S. epidermidis* MO34 and/or MO35 alone or in combination with 6-HAP or the 6-HAP or a derivative thereof alone and any other desired active ingredients that improves skin health.

Any of a variety of methods known in the art can be used to administer a probiotic composition or compound of the disclosure to a subject. For example, a 6-HAP anti-neoplastic agent and/or microbial probiotic composition of the disclosure may be formulated for topical administration (e.g., as a lotion, cream, spray, gel, or ointment). Such topical formulations are useful in treating or inhibiting neoplastic cells, UV damage leading to neoplasms and the like. Examples of formulations include topical lotions, creams, soaps, wipes, and the like. In embodiments, where a neoplasia or cancer is not topical, the administration of a compound of formula I(a), I(b) and/or II can be delivered intraperitoneally, intravenously, by inhalation etc.

The disclosure thus provides a method of treating or reducing the risk of cancer (e.g., skin cancer) by promoting an effective skin biome comprising *S. epidermidis*. The disclosure also provides a method of treating or reducing the risk of skin cancer comprising administering a probiotic comprising *S. epidermidis* that produces an anticancer agent of the disclosure.

The disclosure also provides an antimicrobial/anticancer molecule having the general formula of Formula I(a):

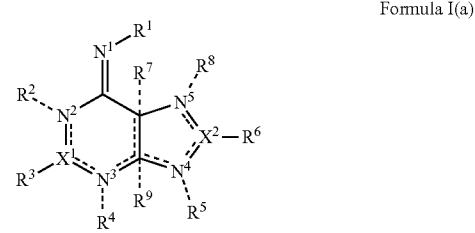

Formula I(a)

or a pharmaceutically acceptable salt or prodrug thereof, wherein, $N^1$-$N^5$ are nitrogen atoms;

$X^1$-$X^2$ are carbon atoms;

the R groups attached by a dashed line are present, or are not present if the R group is connected to an atom that is bound to another atom by a double covalent bond;

the bond indicated by both a straight line and a dashed line indicate that the bond may be a single covalent bond or a double covalent bond;

the fused heterocyclic ring system comprises three double bonds with $N^2$ or $N^3$ forming a double bond and with $X^1$, and with $N^4$ or $N^5$ forming a double bond with $X^2$;

$R^1$ is a hydroxyl, ester, carboxylic acid, or —O—$R^{10}$;

$R^2$, $R^4$, $R^5$, $R^7$-$R^9$ are independently a H, D, optionally substituted ($C_1$-$C_6$)-alkyl, optionally substituted ($C_1$-$C_6$)-alkenyl, optionally substituted ($C_1$-$C_6$)-alkynyl, optionally substituted ($C_3$-$C_{12}$)cycloalkyl, optionally substituted ($C_4$-$C_{12}$)cycloalkenyl, optionally substituted aryl;

$R^3$ and $R^6$ are independently selected from a H, D, optionally substituted ($C_1$-$C_6$)-alkyl, optionally substituted ($C_1$-$C_6$)-heteroalkyl, optionally substituted ($C_1$-$C_6$)-alkenyl, optionally substituted ($C_1$-$C_6$)-heteroalkenyl, optionally substituted $(C_1-C_6)$-alkynyl, optionally substituted $(C_1-C_6)$-heteroalkynyl, optionally substituted $(C_3-C_{12})$cycloalkyl, optionally substituted $(C_4-C_{12})$cycloalkenyl, optionally substituted aryl, optionally substituted heterocycle, halide, hydroxyl, carbonyl, aldehyde, carboxyl, ester, alkoxy, carboxyamide, amine, imine, azide, cyano, nitro, nitroso, thiol, sulfide, sulfoxide, sulfone, and phosphate;

$R^{10}$ is selected from D, optionally substituted $(C_1-C_6)$-alkyl, optionally substituted $(C_1-C_6)$-heteroalkyl, optionally substituted $(C_1-C_6)$-alkenyl, optionally substituted $(C_1-C_6)$-heteroalkenyl, optionally substituted $(C_1-C_6)$-alkynyl, optionally substituted $(C_1-C_6)$-heteroalkynyl, optionally substituted $(C_3-C_{12})$cycloalkyl, optionally substituted $(C_4-C_{12})$cycloalkenyl, optionally substituted aryl, and optionally substituted heterocycle.

In another embodiment, the compound has the general formula of Formula I(b):

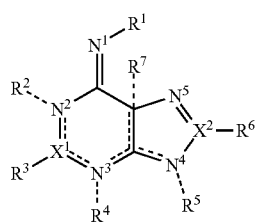

Formula I(b)

or a pharmaceutically acceptable salt or prodrug thereof, wherein, $N^1$-$N^5$ are nitrogen atoms;

$X^1$-$X^2$ are carbon atoms;

the R groups attached by a dashed line are present, or are not present if the R group is connected to an atom that is bound to another atom by a double covalent bond; the bond indicated by both a straight line and a dashed line indicate that the bond may be a single covalent bond or a double covalent bond;

the fused heterocyclic ring system comprises three double bonds with $N^2$ or $N^3$ forming a double bond with $X^1$, and with $N^4$ or $N^5$ forming a double bond with $X^2$;

$R^1$ is a hydroxyl, ester, carboxylic acid, or —O—$R^{10}$;

$R^2$, $R^4$, $R^5$, and $R^7$ are independently a H, D, optionally substituted $(C_1-C_6)$-alkyl, optionally substituted $(C_1-C_6)$-alkenyl, optionally substituted $(C_1-C_6)$-alkynyl, optionally substituted $(C_3-C_{12})$cycloalkyl, optionally substituted $(C_4-C_{12})$cycloalkenyl, optionally substituted aryl;

$R^{10}$ is selected from D, optionally substituted $(C_1-C_6)$-alkyl, optionally substituted $(C_1-C_6)$-heteroalkyl, optionally substituted $(C_1-C_6)$-alkenyl, optionally substituted $(C_1-C_6)$-heteroalkenyl, optionally substituted $(C_1-C_6)$-alkynyl, optionally substituted $(C_1-C_6)$-heteroalkynyl, optionally substituted $(C_3-C_{12})$cycloalkyl, optionally substituted $(C_4-C_{12})$cycloalkenyl, optionally substituted aryl, and optionally substituted heterocycle.

In yet another embodiment, the disclosure provides a compound of general formula II.

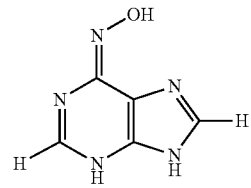

Formula II or a pharmaceutically acceptable salt or prodrug thereof; or a tautomer of the compound of Formula II, or a pharmaceutically acceptable salt or prodrug of the tautomer of compound of Formula II thereof.

Methods and compositions useful for treatment of cancer are provided. In one embodiment the disclosure provides compositions and methods useful for treating a cancer wherein the methods and compositions comprise Formula I(a), I(b) and/or II, a derivative or salt thereof. The methods and compositions of the disclosure can be used alone or in combination with other anticancer agents to treat such cancer. In one embodiment, the composition comprises S. epidermidis MO34 and/or MO38 in addition to a compound of Formula I(a), I(b) and/or II.

Suitable acids for use in the preparation of pharmaceutically acceptable salts of a compound of the disclosure, include, but are not limited to, aceptic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, a-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphtoic acid, nicotinic acid, nitric acid, oleic acid, orotic acid, oxalic acid, palmitic acid, pamoic acid, perchloric acid, phosphoric acid, L-pyroglutamic acid, saccharic acid, salicyclic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable acids for use in the preparation of pharmaceutically acceptable salts, include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-Lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

Pharmaceutically acceptable salts comprise pharmaceutically-acceptable anions and/or cations. Pharmaceutically-acceptable cations include among others, alkali metal cations (e.g., Li+, Na+, K+), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl—, Br—), sulfate, acetates (e.g., acetate, trifluoroacetate), ascorbates, aspartates, benzoates, citrates, and lactate.

A compound disclosed herein may also have a prodrug form. A prodrug is a functional derivative of the compound disclosed herein and is readily convertible into the parent compound in vivo. Prodrugs are often useful because, in some situations, they may be easier to administer than the parent compound. They may, for instance, be bio-available by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). In a specific example, if a parent compound disclosed herein has a hydroxyl group, this hydroxyl group may be converted to an ester in attempts to increase bioavailability, solubility, injection site pain relief, elimination of an unpleasant taste, decreased toxicity, decreased metabolic inactivation, increased chemical stability, and/or prolonged or shortened action of the hydroxyl containing parent compound. In another specific example, if a parent compound disclosed herein has an amine group, this amine group may be converted to a Schiff base in attempts to increase bio-availability, solubility, injection site pain relief, elimination of an unpleasant taste, decreased toxicity, decreased metabolic inactivation, increased chemical stability, and/or prolonged or shortened action of the hydroxyl containing parent compound.

A pharmaceutical composition comprising a compound disclosed herein, a derivative or analog thereof, including pharmaceutical salt forms and prodrug forms, can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

A pharmaceutical composition comprising a probiotic disclosed herein comprising a commensal bacterial (e.g., *S. epidermidis* MO34 and/or MO38) or an engineered form thereof (e.g., attenuated or genetically modified), may be formulated in any dosage form that is suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation comprising a probiotic disclosed herein may also comprise liposomes, micelles, microspheres, nanosystems, and mixtures thereof.

In one embodiment, a bandage or dressing is provided comprising a compound of formula I(a), I(b) and/or II, and/or a probiotic commensal skin bacteria described herein. In various aspects, a bandage or dressing is provided the major constituents of which includes a matrix and a topical probiotic composition of Formulas I or II described above. In various aspects, a bandage or dressing is provided the major constituents of which includes a matrix and a probiotic commensal skin bacteria. In various aspects, a bandage or dressing is provided the major constituents of which includes a matrix and a probiotic commensal skin bacteria fermentation extract. In various aspects, a bandage or dressing is provided the major constituents of which includes a matrix and glycerol. In one embodiment, the bandage or dressing is applied to site of skin damage or injury. In another embodiment, the bandage or dressing is applied to a site of infection.

A "pharmaceutically acceptable carrier" is intended to include solvents, dispersion media, coatings, antibacterial and antifungal agents (as needed so long as they are not detrimental to the probiotic commensal bacteria), isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

Pharmaceutically acceptable carriers and excipients suitable for use in the topical formulations disclosed herein include, but are not limited to, aqueous vehicles, water-miscible vehicles, non-aqueous vehicles, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

A pharmaceutical composition comprising a probiotic may be formulated in the forms of ointments, creams, sprays and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain material substantially uniformly throughout the liquid carrier. Suitable gelling agents include cross-linked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

A pharmaceutical composition comprising a probiotic disclosed herein, may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy.

The pharmaceutical compositions according to the disclosure may be administered locally or systemically. A "therapeutically effective dose" is the quantity of an agent (e.g., a compound of Formula I(a), I(b) and/or II) or a probiotic comprising a commensal bacterial according to the disclosure necessary to prevent, to cure, or at least partially arrest the symptoms of cancer (e.g., proliferation, metastasis, growth etc.). Amounts effective for this use will, of course, depend on the severity of the cancer, the weight and general state of the subject and/or the surface area to be treated. Typically, dosages used in vitro may provide useful guidance in the amounts useful for human and animal treatment. Various considerations are described, e.g., in Langer, Science, 249: 1527, (1990); Gilman et al. (eds.) (1990), each of which is herein incorporated by reference. Dosage regima can be adjusted to provide the optimum therapeutic response. For example, several divided doses can be administered daily or the dose can be proportionally reduced as indicated by the exigencies of the therapeutic situation.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The disclosure provides for a compound (e.g., a compound of Formula I(a), I(b) and/or II) disclosed herein, derivative or analog thereof, including pharmaceutical salt forms and prodrug forms, that can be administered to any host, including a human or non-human animal, in an amount effective to inhibit the growth, spread or proliferation of a cancer cell or neoplasm. In one embodiment, the administration results in the inhibition of growth, proliferation, migration and/or metastasis of a cancer or neoplastic cell.

Any of a variety of art-known methods can be used to administer a compound (e.g., a compound of Formula I(a), I(b) and/or II) disclosed herein, a derivative or analog thereof, including pharmaceutical salt forms and prodrug forms, either alone or used in combination with one or more other therapeutic agents. For example, administration can be parenterally by injection or by gradual infusion over time. The agent(s) can be administered intravenously, intraperitoneally, intramuscularly, subcutaneously, intracavity, by inhalation, topically or transdermally.

A pharmaceutical composition (e.g., a compound of Formula I(a), I(b) and/or II or a probiotic composition comprising a commensal bacterial such as *S. epidermidis* MO34 and/or MO38, or a combination of a commensal bacteria and a compound of the disclosure) can be administered in a convenient and appropriate manner, such as by injection (subcutaneous, intravenous, etc.), oral administration, inhalation, transdermal application, topical via lotion, cream or ointment, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

In another embodiment, a pharmaceutical composition comprising a compound and/or a commensal probiotic disclosed herein, a derivative or analog thereof, including pharmaceutical salt forms and prodrug forms, can be formulated either alone or in combination with one or more additional therapeutic agents, including, but not limited to, chemotherapeutics, antibiotics (so long as they don't destroy the probiotic benefits), antifungal-agents, anti-pruritics, analgesics, and/or antiviral agents.

Topical administration, as used herein, include (intra) dermal, conjunctival, intracorneal, intraocular, ophthalmic, auricular, transdermal, nasal, vaginal, uretheral, respiratory, and rectal administration. Such topical formulations are useful in treating or inhibiting cancers of the eye, skin, and mucous membranes (e.g., mouth, vagina, rectum). Examples of formulations in the market place include topical lotions, creams, soaps, wipes, and the like.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions disclosed herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient disclosed herein, a propellant as solvent; and/or a surfactant, such as sorbitan trioleate, oleic acid, or an oligolactic acid.

A pharmaceutical composition comprising a compound disclosed herein, a derivative or analog thereof, including pharmaceutical salt forms and prodrug forms, may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions disclosed herein; a suitable powder base, such as lactose or starch; and a performance modifier, such as 1-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. A pharmaceutical composition comprising a compound disclosed herein, a derivative or analog thereof, including pharmaceutical salt forms and prodrug forms, for inhaled/intranasal administration may further comprise a suitable flavor, such as menthol and levomenthol, or sweeteners, such as saccharin or saccharin sodium.

A pharmaceutical composition comprising a compound disclosed herein, a derivative or analog thereof, including pharmaceutical salt forms and prodrug forms, for topical administration may be formulated to be immediate release or modified release, including delayed-, sustained-, pulsed-, controlled-, targeted, and programmed release.

A pharmaceutical composition comprising a compound disclosed herein, a derivative or analog thereof, including pharmaceutical salt forms and prodrug forms, may be formulated into liposomes to reduce toxicity or increase bioavailability. Other methods for delivery include oral methods that entail encapsulation of the in microspheres or proteinoids, aerosol delivery (e.g., to the lungs), or transdermal delivery (e.g., by iontophoresis or transdermal electroporation). Other methods of administration will be known to those skilled in the art.

A pharmaceutical composition comprising a compound disclosed herein, a derivative or analog thereof, including pharmaceutical salt forms and prodrug forms, may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s). Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

The pharmaceutical composition comprising a compound disclosed herein, a derivative or analog thereof, including pharmaceutical salt forms and prodrug forms, that is formulated in a modified release dosage form may be fabricated using a matrix controlled release device (see, Takada et al in "Encyclopedia of Controlled Drug Delivery," Vol. 2, Mathiowitz ed., Wiley, 1999).

In one embodiment, the pharmaceutical composition comprising a compound disclosed herein, a derivative or analog thereof, including pharmaceutical salt forms and prodrug forms, in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, a pharmaceutical composition comprising a compound disclosed herein, a derivative or analog thereof, including pharmaceutical salt forms and prodrug forms are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

A pharmaceutical composition comprising a compound disclosed herein, a derivative or analog thereof, including pharmaceutical salt forms and prodrug forms, in a modified release dosage form may be prepared by methods known to those skilled in the art, including direct compression, dry or wet granulation followed by compression, melt-granulation followed by compression.

The pharmaceutical composition comprising a compound disclosed herein, a derivative or analog thereof, including pharmaceutical salt forms and prodrug forms, in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s) and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-tolunesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

The total amount of the active ingredient(s) released and the release rate can substantially by modulated via the thickness and porosity of the semipermeable membrane, the composition of the core, and the number, size, and position of the delivery ports.

The pharmaceutical composition comprising a compound disclosed herein, a derivative or analog thereof, including pharmaceutical salt forms and prodrug forms, in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In a certain embodiment, a pharmaceutical composition comprising a compound disclosed herein, a derivative or analog thereof, including pharmaceutical salt forms and prodrug forms are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In a particular embodiment, a pharmaceutical composition comprising a compound disclosed herein, a derivative or analog thereof, including pharmaceutical salt forms and prodrug forms are formulated as ESC controlled-release dosage form, which comprises an osmotic membrane that coats a core comprising the active ingredient(s), a hydroxylethyl cellulose, and other pharmaceutically acceptable excipients or carriers.

A pharmaceutical composition comprising a compound disclosed herein, a derivative or analog thereof, including pharmaceutical salt forms and prodrug forms, may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

A pharmaceutical composition comprising a compound disclosed herein, a derivative or analog thereof, including pharmaceutical salt forms and prodrug forms, may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical composition comprising a compound disclosed herein, a derivative or analog thereof, including pharmaceutical salt forms and prodrug forms, may include one or more pharmaceutically acceptable carriers and excipients, including, but not limited to, aqueous vehicles, water-miscible vehicles, non-aqueous vehicles, antibacterial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Preparations for parenteral administration of a pharmaceutical composition comprising a compound disclosed herein, a derivative or analog thereof, including pharmaceutical salt forms and prodrug forms include sterile aqueous or non-aqueous solutions, suspensions, and emulsions. Suitable aqueous vehicles include, but are not limited to, water, saline, physiological saline or phosphate buffered saline (PBS), sodium chloride injection, Ringers injection, isotonic dextrose injection, sterile water injection, dextrose, lactated Ringers injection, alcoholic/aqueous solutions, and emulsions or suspensions. Non-aqueous vehicles include, but are not limited to, injectable organic esters such as ethyl oleate, and fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antibacterials, anti-oxidants, cheating agents, inert gases and the like also can be included.

Suitable antibacterial agents or preservatives that can be used with a compound of the disclosure include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

A pharmaceutical composition comprising a compound disclosed herein, a derivative or analog thereof, including pharmaceutical salt forms and prodrug forms may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. Parenteral formulations are sterile, as known and practiced in the art.

In one embodiment, the pharmaceutical composition comprising a compound disclosed herein, a derivative or analog thereof, including pharmaceutical salt forms and prodrug forms are formulated as ready-to-use sterile solutions. In another embodiment, the pharmaceutical composition comprising a compound disclosed herein, a derivative or analog thereof, including pharmaceutical salt forms and prodrug forms are formulated as sterile dry soluble products, including lyophilized powders and hypodermic tablets, to be reconstituted with a vehicle prior to use. In yet another embodiment, the pharmaceutical composition comprising a compound disclosed herein, a derivative or analog thereof, including pharmaceutical salt forms and prodrug forms are formulated as ready-to-use sterile suspensions. In yet another embodiment, the pharmaceutical composition comprising a compound disclosed herein, a derivative or analog thereof, including pharmaceutical salt forms and prodrug forms are formulated as sterile dry insoluble products to be reconstituted with a vehicle prior to use. In still another embodiment, the pharmaceutical composition comprising a compound disclosed herein, a derivative or analog thereof, including pharmaceutical salt forms and prodrug forms are formulated as ready-to-use sterile emulsions.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

A pharmaceutical composition comprising a compound disclosed herein, a derivative or analog thereof, including pharmaceutical salt forms and prodrug forms, suitable for injectable use include sterile aqueous solutions (where water soluble) or dispersions and sterile powders for the extemporaneous preparation of sterile injectable solutions or dispersions. In all cases, the pharmaceutical composition comprising a compound disclosed herein, a derivative or analog thereof, including pharmaceutical salt forms and prodrug forms, should be sterile and should be fluid to the extent that easy syringability exists. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating a pharmaceutical composition comprising a compound disclosed herein, a derivative or analog thereof, including pharmaceutical salt forms and prodrug form in the required amount in an appropriate solvent with one or a combination of ingredients enumerated above, as required, followed by filtered sterilization. Generally, dispersions are prepared by incorporating a pharmaceutical composition comprising a compound disclosed herein, a derivative or analog thereof, including pharmaceutical salt forms and prodrug forms, into a sterile vehicle that contains a basic dispersion medium and the required other ingredients from those enumerated above.

A pharmaceutical composition comprising a compound disclosed herein, a derivative or analog thereof, including pharmaceutical salt forms and prodrug forms, can be orally administered, for example, with an inert diluent or an assimilable edible carrier. The pharmaceutical composition comprising a compound disclosed herein, a derivative or analog thereof, including pharmaceutical salt forms and prodrug forms, and other ingredients can also be enclosed in a hard or soft-shell gelatin capsule, compressed into tablets, or incorporated directly into the individual's diet. For oral therapeutic administration, the pharmaceutical composition comprising a compound disclosed herein, a derivative or analog thereof, including pharmaceutical salt forms and prodrug forms, can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed.

A pharmaceutical composition comprising a compound disclosed herein, a derivative or analog thereof, including pharmaceutical salt forms and prodrug forms are disclosed herein, may be formulated as immediate or modified release dosage forms, including delayed-, sustained-, pulsed-, controlled, targeted-, and programmed-release forms.

A pharmaceutical composition comprising a compound disclosed herein, a derivative or analog thereof, including pharmaceutical salt forms and prodrug forms are disclosed herein, may be formulated as a suspension, solid, semi-solid, or thixotropic liquid, for administration as an implanted depot. In one embodiment, the pharmaceutical composition comprising a compound disclosed herein, a derivative or analog thereof, including pharmaceutical salt forms and prodrug forms are dispersed in a solid inner matrix, which is surrounded by an outer polymeric membrane that is insoluble in body fluids but allows the active ingredient in the pharmaceutical compositions to diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, poly dimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

A therapeutically effective amount can be measured as the amount sufficient to decrease a subject's symptoms (e.g., tumor growth, cancer spread and the like). Typically, the subject is treated with an amount of a therapeutic composition comprising a compound disclosed herein, a derivative or analog thereof, including pharmaceutical salt forms and prodrug forms, sufficient to reduce a symptom of a disease or disorder by at least 50%, 90% or 100%. Generally, the optimal dosage will depend upon the disorder and factors such as the weight of the subject, the type of cancer or neoplasm, the weight, sex, and degree of symptoms. Nonetheless, suitable dosages can readily be determined by one skilled in the art. Typically, a suitable dosage is 0.5 to 40 mg/kg body weight, e.g., 1 to 8 mg/kg body weight.

The compounds disclosed herein may also be combined or used in combination with other agents useful in the treatment, prevention, or amelioration of one or more symptoms of various syndromes, disorders, and/or diseases. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously (at the same time or in the same formulation) or sequentially with a compound as disclosed herein. When a compound as disclosed herein disclosed herein is used contemporaneously with one or more other drugs, a pharmaceutical composition containing such other drugs in addition to the compound disclosed herein may be utilized, but is not required. Accordingly, the pharmaceutical compositions disclosed herein include those that also contain one or more other active ingredients or therapeutic agents (e.g., a chemotherapeutic or other anti-cancer agent, an antibiotic, and the like), in addition to a compound disclosed herein.

Examples of chemotherapeutic agents include: alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammaII and calicheamicin omegaII; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® (docetaxel) (Rhone-Poulenc Rorer, Antony, France); chloranbucil; GEMZAR® (gemcitabine); 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN® topoisomerase 1 inhibitor; ABARELLX® rmRH; antibodies such as trastuzumab and pharmaceutically acceptable salts, acids or derivatives of any of the above.

Suitable antibiotics include aminoglycosides (e.g., gentamicin), beta-lactams (e.g., penicillins and cephalosporins), quinolones (e.g., ciprofloxacin), and novobiocin. Generally, the antibiotic is administered in a bactericidal, antiviral and/or antifungal amount. In a certain embodiment, a compound disclosed herein can be combined with one or more antibiotics, including, but not limited to, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, clofazimine, cloxacillin, colistin, dalfopristan, demeclocycline, dicloxacillin, dirithromycin, doxycycline, erythromycin, enafloxacin, enviomycin, ertepenem, ethambutol, flucloxacillin, fosfomycin, furazolidone, gatifloxacin, geldanamycin, gentamicin, herbimicin, imipenem, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, oxytetracycline, penicillin, piperacillin, platensimycin, polymixin B, prochlorperazine, prontocil, quinupristine, rifabutin, roxithromycin, spectinomycin, sulfacetamide, sulfamethizole, sulfamethoxazole, teicoplanin, telithromycin, tetracycline, thioacetazone, thioridazine, ticarcillin, tobramycin, trimethoprim, troleandomycin, trovafloxacin, and vancomycin.

In yet a further embodiment, a compound provided herein can be combined with one or more steroidal drugs known in the art, including, but not limited to, aldosterone, beclometasone, betamethasone, deoxycorticosterone acetate, fludrocortisone acetate, hydrocortisone (cortisol), prednisolone, prednisone, methylprenisolone, dexamethasone, and triamcinolone.

In certain embodiments, a compound disclosed herein can be combined with one or more anti-fungal agents, including, but not limited to, amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

The compounds disclosed herein can also be administered in combination, preferably sequentially, with other classes of compounds, including, but not limited to, antipruritics; anticoagulants, such as bivalirudin; thrombolytics, such as streptokinase; non-steroidal anti-inflammatory agents, such as aspirin; antiplatelet agents, such as clopidogrel; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepam; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anti-coagulants, such as warfarin; low molecular weight heparins, such as enoxaparin; Factor VIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; anti-inflammatories; anti-proliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); anti-metabolites, such as folate antagonists, purine analogues, and pyrridine analogues; antibiotics, such as anthracyclines, bleomycins, mitomycin, dactinomycin, and plicamycin; enzymes, such as L-asparaginase; famesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

The disclosure provides a method for inhibiting a cancer and/or neoplastic disorders by contacting or administering a therapeutically effective amount of a compound disclosed herein, derivative or analog thereof either alone or in combination with other anticancer agents to a subject who has, or is at risk of having, such a disorder. The term "inhibiting"

means preventing or ameliorating a sign or symptoms of a syndrome, disorder, and/or disease (e.g., tumor growth, cancer cell proliferation and/or migration, cancer cell metastasis, and the like).

The disclosure also provides a method for inhibiting the growth of a tumor or cancer by contacting the tumor cells, cancer cells or neoplastic cells with a compound, derivative or analog thereof, including pharmaceutical salt and prodrug forms, with an inhibiting effective amount. The term "contacting" refers to exposing the cells (e.g., tumor, cancer or neoplastic cell) to an agent. Contacting of an organism with a topical probiotic composition of the disclosure can occur in vitro, for example, by adding the topical probiotic composition to a bacterial culture to test for susceptibility of the bacteria. Alternatively, contacting can occur in vivo, for example by contacting the topical probiotic composition with a subject afflicted with a bacterial infection, a subject susceptible to infection or a subject suffering from or at risk of developing a cancer.

Contacting can occur in vivo, for example, by administering the compound, derivative or analog thereof, including pharmaceutical salt and prodrug forms, to a subject afflicted with an infection, a tumor, cancer or neoplasm. In vivo contacting includes both parenteral as well as topical. "Inhibiting" or "inhibiting effective amount" refers to the amount of agent that is sufficient to cause, for example, tumor, cancer or neoplastic cell death, inhibition of growth and/or migration and/or inhibition of prevention of metastasis.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound disclosed herein with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The disclosure also provides method of identifying commensal bacteria that can produce 6-HAP comprising determining the presence of or expression of one or more of the sequences of Table 2 (i.e., SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, and/or 55) or sequences that are at least 98% identical thereto. Method of determining identity and homology are incredibly well known in the art and have been performed for at least the past 20 years. Detecting expression of a gene can be determined by quantitative RT-PCR, southern blot, norther blot etc. Microorganisms that have an expression profile similar to *S. epidermidis* strains MO34 and/or MO38 and containing or expression sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, and/or 55 can be used in the methods and compositions of the disclosure.

The disclosure also provide a diagnostic to determine risk or presence of skin cancer. The method comprising obtaining a microbiome sample from the skin of a subject at risk of or having skin cancer and measuring the production of a compound of formula I or II or identifying bacteria in the microbiome that produce a compound of formula I or II, wherein the presence of a compound of formula I or II or a bacteria that produces a compound of formula I or II is indicative of a cancer or risk of developing cancer. In one embodiment, the subject is a human subject. In another embodiment, the method comprises identifying the presence of a *S. epidermidis* strain. In another embodiment, the *S. epidermidis* strain has the phenotype of ATCC Number _____ (strain designation S.epi-MO38 UCSD 20180315) and/or ATCC Number _____ (strain designation S.epi-MO34 UCSD 20180315).

The invention is further illustrated by the following examples:

Examples

Bacteria. Clinical strains of *S. epidermidis* were isolated from the skin surface of healthy donors who had no contact with hospitals over 6 months. All strains were characterized by coagulase and catalase activities on rabbit plasma. *S. epidermidis* strains were further characterized using API-Staph (BIOMERIEUX Inc., Lyon, France) and by full-length 16SrRNA gene sequence. *S. epidermidis* (ATCC12228 and ATCC1457), *S. aureus* (ATCC35556), *S. hominis* (ATCC27844) *E. coli* (ATCC25922) and *P. aeruginosa* (ATCC14213) were obtained from American Type Culture Collection (Manassas, VA). GAS (NZ131), GBS (DK23) and MRSA (USA300 and Sanger252) were generously gifted.

Characterization and purification of 6-HAP. *S. epidermidis* MO34 strain was cultured in tryptic soy broth (TSB) at 37° C. for 24 hrs and was removed from culture supernatant with 0.22 µm filter. The filtrated culture supernatant was lyophilized and the residue was suspended in methanol to precipitate proteins. The supernatant was dried under vacuum and the residual substance was dissolved in water. As 6-HAP is weakly retained C18 reverse phase column, the solution was applied on Sep-Pak cartridge (Waters Co., Milford, MA) and washed with $H_2O$, and eluted with 5% acetonitrile in $H_2O$. The elution was lyophilized and suspended in 90% acetonitrile/10% water. The supernatant was separated by HPLC. After each purification step, activity was determined by radial diffusion assay against GAS (NZ131). Purified compound was characterized by Mass Spectrometry and NMR. The purified 6-HAP was lyophilized and dry weight was measured to measure specific activity.

Antimicrobial assays. Radial diffusion assay was performed using GAS (NZ131) strain. Briefly, melted Todd-Hewitt broth (THB) agar (10 mL) was mixed with GAS [$1 \times 10^6$ colony forming unit (CFU)] and poured in a 10 cm petri dish. Two to four μL of test samples was applied in a small well punched on the agar plate. Plates were incubated at 37° C. overnight to allow visible growth of bacteria. Antibacterial activity was indicated by the clear zone (no bacterial growth) around the well.

To determine MBC, bacteria were cultured in TSB (*Staphylococcus*), THB (*Streptococcus*) or Nutrient broth (*P. aeruginosa* and *E. coli*) by reaching exponential phase ($OD_{600}$=0.5-0.8). MBC of 6-HAP was determined by incubating $1 \times 10^5$ CFU/mL bacteria with 2-fold serial dilutions of synthetic 6-HAP in half strength Muller-Hinton broth (MHB) in PBS at 37° C. for 24 hrs. After incubation, the number of viable bacteria was measured by counting CFU after spreading 10-fold serial dilutions of bacteria on suitable agar plates. MBC was determined as a 3-log reduction (99.9%) of viable bacteria after 24 hour incubation.

BrdU incorporation assay. GAS (NZ131) or *S. epidermidis* (ATCC12228) were cultured in THB or TSB, respectively, by reaching exponential phase. The bacteria ($1 \times 10^6$ CFU) were incubated in 100 μL of THB or TSB containing 10 μM BrdU, and 25 μg/mL 6-HAP or 5 μg/mL mitomycin C at 37° C. until 60 min. After incubation, bacteria cells were immediately fixed FixDenat solution (Roche, Mannheim, Germany). BrdU incorporation into nascent DNA was measured in a time-dependent manner using BrdU incorporation assay kit (Roche) according to the manual.

Figure 3A:
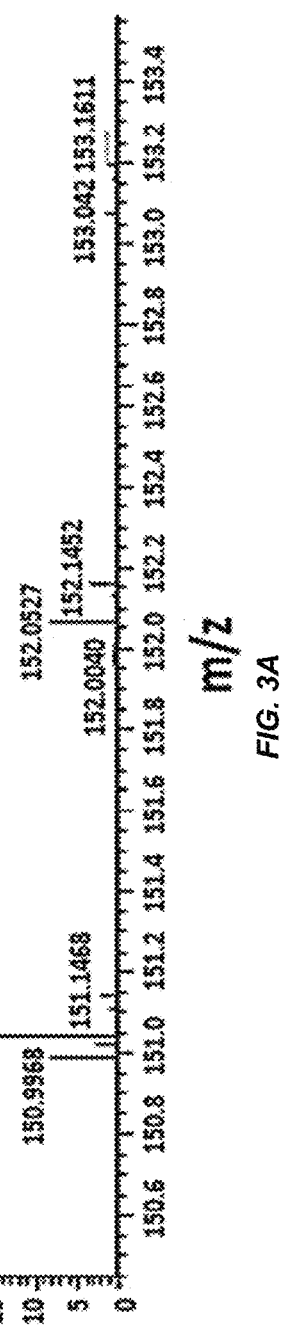
FIG. 3A-G shows *S. epidermidis* strains produce 6-N-hydroxyaminopurine with antimicrobial activity. (a) Molecular mass of purified antibiotic from *S. epidermidis* MO34 strain analyzed by high-resolution electron spray ionization mass spectrometry. (b) $^{15}N$ isotope incorporation into the antibiotic molecule after culturing *S. epidermidis* MO34 in TSB containing ammonium-$^{15}N$ chloride (12.5 mM) for 24 hrs. (c-d) Comparison of chemical shifts of purified antibiotic (c) with those of synthetic 6-HAP (d) in $^1$H-NMR. (e-f) Comparison of the fragmentation profile of purified antibiotic (e) with that of synthetic 6-HAP (f) on electron-impact mass spectrometry. (g) The determined chemical structure of the antibiotic (6-HAP).
Figure 3B:
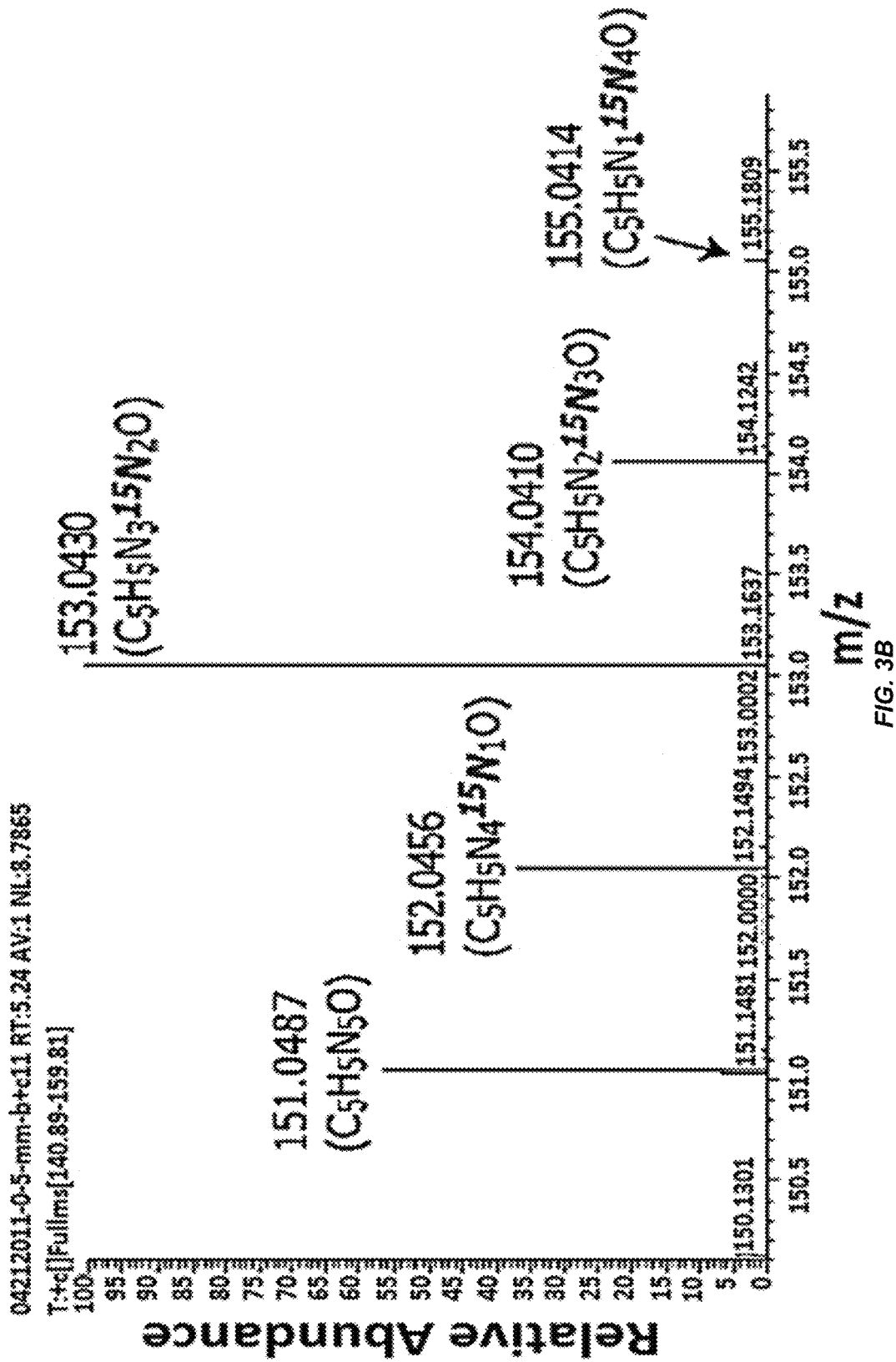
Figure 3C:
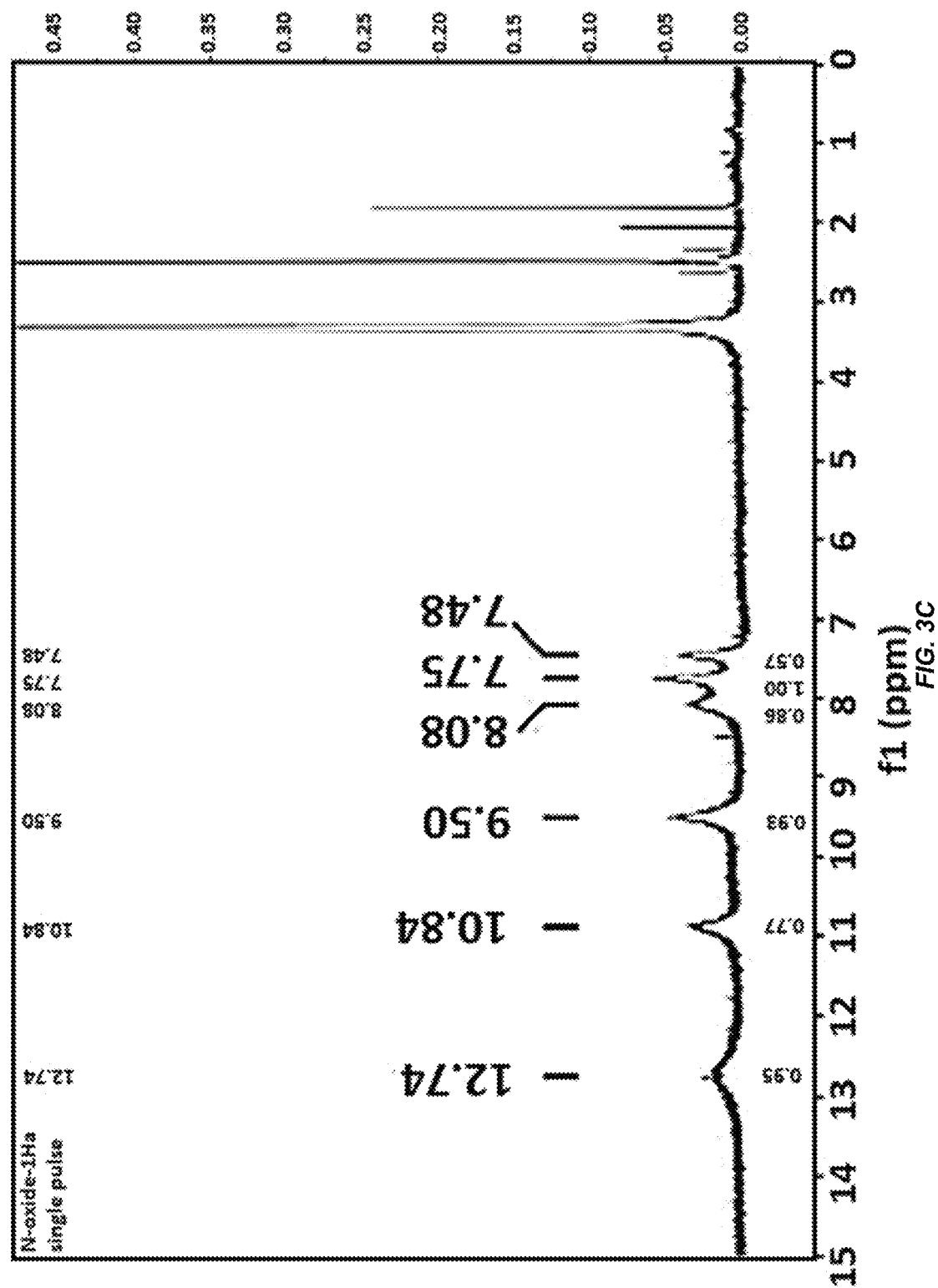
Figure 3D:
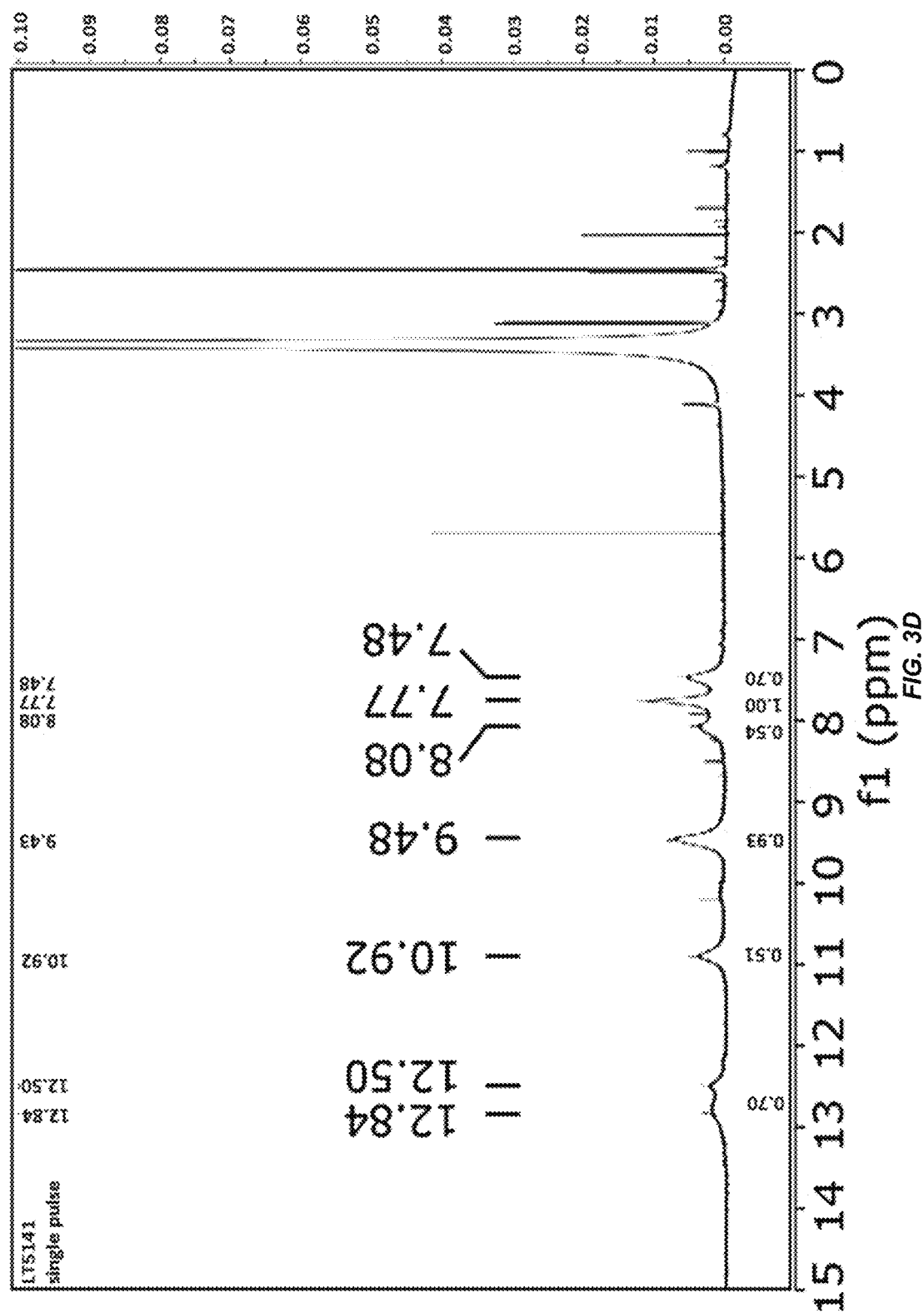
Figure 3E:
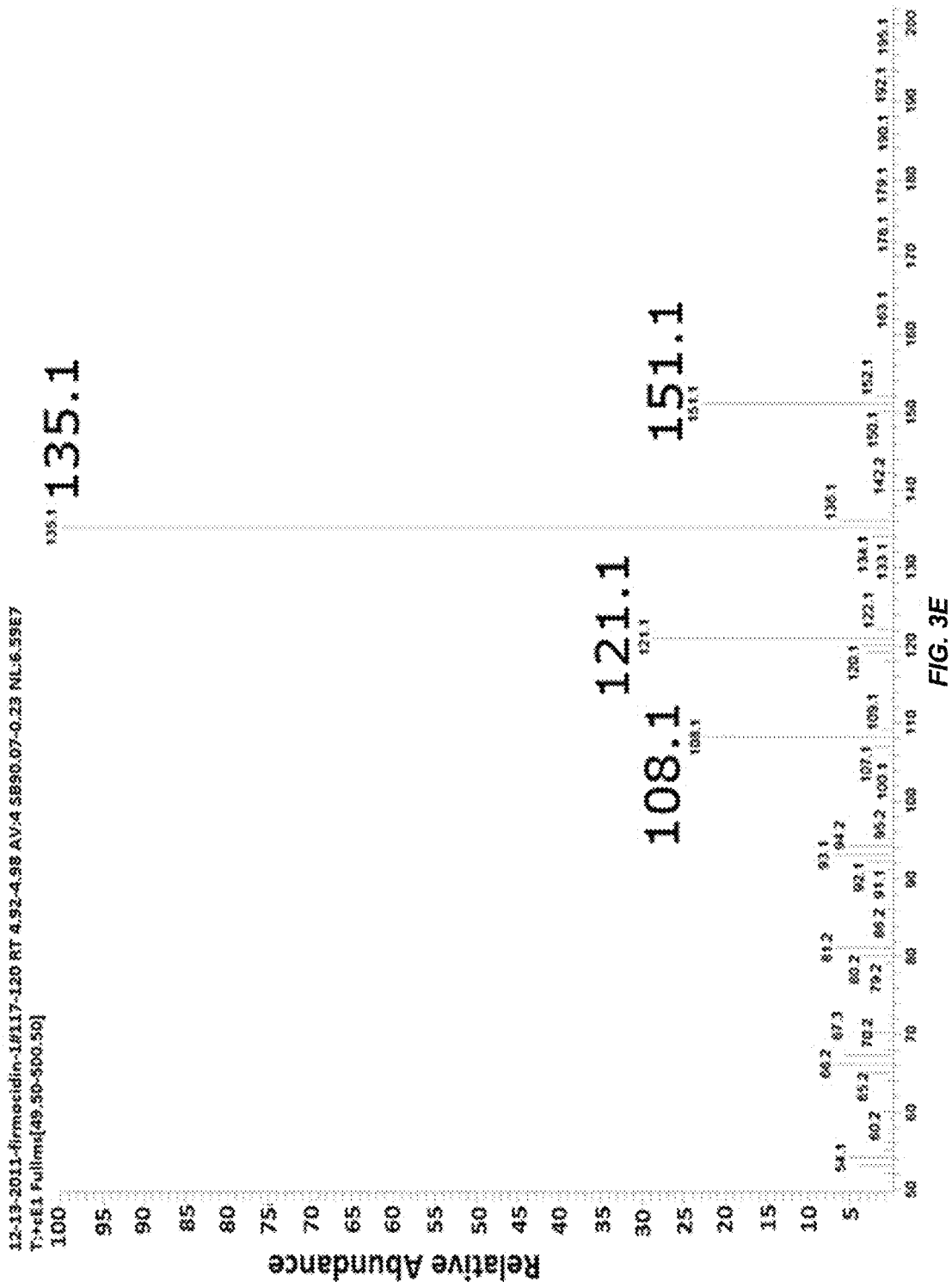

In vitro DNA polymerization assay. To examine if 6-HAP disrupts adenosine-thymidine base pair matching in DNA extension, IRDye800-labeled 18-bp primer and 25-bp template which required adenosine (X=T) or cytidine (X=G) at the initial base of overhang for extension were designed (FIG. 3e). The reaction mixture contained 100 nM primer/template, 0.1 U Klenow fragment (exo) DNA polymerase (Promega, Madison, WI), 1 μM dNPTs in DNA polymerase buffer. The mixture was incubated at 37° C. for 10 min. The reaction was terminated by adding stop solution (98% formaldehyde and 20 mM EDTA). The extended DNA was separated from primer by electrophoresis on a 20% denaturing polyacrylamide gel containing 7 M urea. Fluorescence was visualized with Oddyssey Imaging System (LI-COR Biosciences, Lincoln, NE).

Cell culture and cell proliferation assay. B16F10 mouse melanoma, Pam212, L5178 and YAC-1 mouse melanoma cell lines were obtained from American Type Culture Collection. Pam212, L5178 and YAC-1 cell lines were maintained in RPMI-1640 supplemented with sodium pyruvate (1 mM), nonessential amino acids (0.1 mM), penicillin (100 unit/mL), streptomycin (100 μg/mL) and 10% heat-inactivated fetal bovine serum (FBS) or horse serum at 37° C. under atmosphere of 5% (v/v) $CO_2$ in air. B16F10 cell line was maintained in DMEM supplemented with penicillin (100 unit/mL), streptomycin (100 μg/mL) and 10% heat-inactivated FBS. NHEKs were obtained from Invitrogen (Life technologies, Grand Island, NY) and maintained in EpiLife medium (Life technologies) supplemented with 60 μM Calcium, epidermal growth factors, penicillin and streptomycin. After 4-hr (tumor cell lines) or 24-hr (NHEK) incubation with 6-HAP, proliferative activity of cells was colorimetrically determined by monitoring BrdU incorporation with Cell Proliferation kit according to the manual (Roche).

Gene silencing of mARCs with siRNA. NHEK was cultured in EpiLife® media containing pre-designed siRNA for mARC1 or mARC2 (Thermo Fisher, Waltham, MA), and RNAiMAX® reagent for 24 hrs. Cells were maintained in EpiLife for 72 hrs, and incubated with 6-HAP (10 μg/mL) for 24 hrs. Anti-proliferative activity of 6-HAP was determined by measuring BrdU incorporation as described above.

HPLC. The active fraction from SepPak cartridge was separated by HPLC in a hydrophilic interaction mode with Venusil XBP NH2 (5 μm, 100 Å, 10×250 mm) (Agela Technologies, Wilmington, DE) with a linier gradient of $H_2O$ from 5% to 35% in acetonitrile at 4 mL/min. The active fraction was fractionated, lyophilized and dissolved in 90% acetonitrile in $H_2O$. The active fraction was further cleaned with PolyHYDROXYETHYL A (5 μm, 60 Å, 9.4×250 mm) with a linier gradient of $H_2O$ from 5% to 35% in acetonitrile at 3 ml/min. Elution profile was monitored with absorbance at 270 nm. After each purification step, activity was determined by radial diffusion assay against GAS (NZ131). The purified 6-HAP was lyophilized and dry weight was measured to measure specific activity.

Mass spectrometry. A Thermo Finnigan MAT900XL mass spectrometer (Thermo Scientific, Waltham, MA) was employed for both low resolution electron impact mass spectrometry (LR-EI-MS) analysis and high resolution electrospray ionization mass spectrometry (HR-EI-MS) using direct insertion probe for sample introduction. The electron energy was set at 70 eV with an emission current of 1.0 mA. High resolution electrospray ionization MS (HR-ESI-MS) analysis was performed on a Thermo LTQ Orbitrap XL mass spectrometer. The source voltage was set at 4500 V with a heated capillary temperature of 250° C. and a sheath gas flow rate of 60 units.

$^1$H-NMR. $^1$H NMR spectra of 6-HAP were recorded on a Mercury Plus 500 MHz Varian instrument. Chemical shifts (δ) are quoted in parts per million (ppm) referenced to the appropriate residual solvent peak (DMSO-d6 or D2O), with abbreviations s and br s denoting singlet and broad singlet. The 1H NMR spectrum of 6-HAP in AcOD-D2O (1:5 v/v) displayed two proton signals in the aromatic region, whereas six signals in DMSO-d6. 1H NMR (500 MHz, AcOD-D2O) δ 8.19 (s, 1H), 8.17 (s, 1H). 1H NMR (500 MHz, DMSO-d6) δ 12.74 (br s, 1H), 10.87 (br s, 0.7H), 9.50 (br s, 1H), 8.08 (br s, 1H), 7.75 (br s, 1H), 7.48 (br s, 0.4H).

Synthesis of 6-HAP. 6-HAP was prepared according to the previous reported procedure with slight modifications (Preparation of nucleobases and nucleosides as antiparasitic agents, Loakes, D.; Too, K., PCT Int. Apl., 2007135380, 29 Nov. 2007). Hydroxylamine hydrochloride (1.20 g, 17.3 mmole) was dissolved in 20 mL of boiling absolute ethanol and a solution of potassium hydroxide (1.12 g, 20.0 mmole) in 4 mL of hot absolute ethanol was added. The precipitated KCl was filtered and washed three times with 2 mL of hot ethanol. Then, 6-chloropurine (300 mg, 1.94 mmole) (Sigma, St. Louis, MO), dissolved in 7 mL of absolute ethanol, was added to the hydroxylamine solution. The reaction was refluxed for 2 hours then cooled to room temperature and allowed to stand overnight. The white precipitate formed was filtered and washed thoroughly with water and then ethanol, and dried under high vacuum to provide 6-HAP (230 mg, 78%) as a white solid. $^1$H NMR (500 MHz, DMSO-d6) δ 12.84 (br s, 1H), 10.92 (br s, 0.5H), 9.48 (br s, 1H), 8.08 (br s, 0.6H), 7.77 (s, 1H), 7.48 (br s, 0.7), in agreement with those reported. The generated 6-HAP was purified by HPLC using Venusil XBP NH2 and PolyHYDROXYETHYL A as described above.

Animals. All experiments involving animal work were in accordance with the approval of the Institutional Animal Care and Use Guidelines of the University of California San Diego (Protocol number: S09074).

In vivo skin infection assay. Dorsal skin of C57BL6 mouse (6-8 weeks female) was shaved, treated with depilatory cream and rinsed with water at least 24 hrs before bacteria application. The shaved skin was cleaned with alcohol swab twice to remove originally colonized bacteria. S. epidermidis (MO34 or ATCC1457) were cultured in TSB overnight, washed with PBS, and then re-suspended in PBS. GAS (NZ131) and MRSA (Sanger252) were cultured in THB or TSB, respectively, until exponential phase ($OD_{600}$=0.5-0.8), washed and re-suspended in PBS. Mouse dorsal skin (2×2 cm) was applied with either strain of S. epidermidis ($1\times10^8$ CFU/10 μL) or PBS (10 μL) for 2 hrs. GAS or MRSA ($1\times10^5$ CFU/10 μL) were epicutaneously challenged on the dorsal skin for 6 hrs. Live bacteria were harvested with a Catch-All Swab (Epicentre Biotechnologies, Madison, WI) pre-wetted with TSB or THB from the skin surface (2×2 cm). Bacteria were suspended by vortex swab head vigorously in 1 mL THB or TSB. Ten-fold serial dilution of the bacteria suspension was spread on a blood agar plate or mannitol salt agar plate to count CFU. GAS (hemolytic) were distinguished from S. epidermidis (non-hemolytic) on a blood agar plate and MRSA (mannitol positive: a large yellow colony) were distinguished from S. epidermidis (mannitol negative: a small pink colony) on a mannitol salt agar plate.

For subcutaneous infection, mouse dorsal skin was subcutaneously injected with GAS ($1\times10^7$ CFU/50 μL in PBS) by 31 G needle. The mice were intravenously injected with 6-HAP at a dose of 20 mg/kg weight or equal volume of vehicle (2.5% DMSO in 0.9% NaCl) after GAS infection. Wound development was monitored everyday by taking photographs along with a wound ruler and lesion size was measured with ImageJ ([http://]rsbweb.nih.gov/ij/)(hyperlink disabled by brackets).

In vivo tumor growth assay. B16F10 were suspended in sterile PBS. Shaved mouse dorsal skin was intradermally injected with $3\times10^5$ cells/50 μL. The C57BL6 mice were subsequently injected with 6-HAP dissolved in 2.5% DMSO/0.9% NaCl solution (40 mg/mL) at the dose of 20 mg/kg mouse via intravascular route every 48 hrs for 2 weeks. Control mice received an equal volume of vehicle. Tumor size was measured as the two perpendicular diameters with a caliper and volume was estimated by a formula, $width^2 \times length/2$. The mice were sacrificed when tumor size reached >2 cm according to the animal protocol.

UV-induced tumor formation in SKH-1 mice. Female SKH-1 hairless mice (4-week old) were purchased from Charles River Laboratories (Wilmington, MA). The back skin of mouse was topically treated with a single application of DMBA (200 nmoles/100 μL acetone) as a tumor initiator. A week after tumor initiation mice were irradiated with 180 $mJ/cm^2$ of UV-B twice a week, and were simultaneously treated with epicutaneous application with live S. epidermidis MO34 or ATCC1457 strain ($1\times10^7$ CFU) 6 times a week for 12 weeks. Tumor incidence and tumor number in each mouse were recoded every week.

Statistical analysis. Statistical analyses were performed using GraphPad Prism 5 software (GraphPad, La Jolla, CA). Independent t-test was used. Independent two-tailed t-tests were used to compare experimental and control groups for significance of differences (P<0.05).

S. epidermidis strains from human skin produce non-proteinaceous antibiotic. To screen for commensal skin bacteria producing antimicrobial activity, 44 strains of S. epidermidis from clinical isolates of normal human skin were cultured overnight and the antimicrobial activity produced by each isolate was determined by radial diffusion assay of their conditioned media against GAS (FIG. 1a). Thirty three strains produced detectable zone of GAS growth inhibition. The S. epidermidis ATCC1457 strain did not show activity and was used as a negative control. Some specific strains, named as MO34 and MO38, produced the largest zone of GAS growth inhibition and were selected first to characterize the most potent antimicrobial molecules.

Figure 1B:
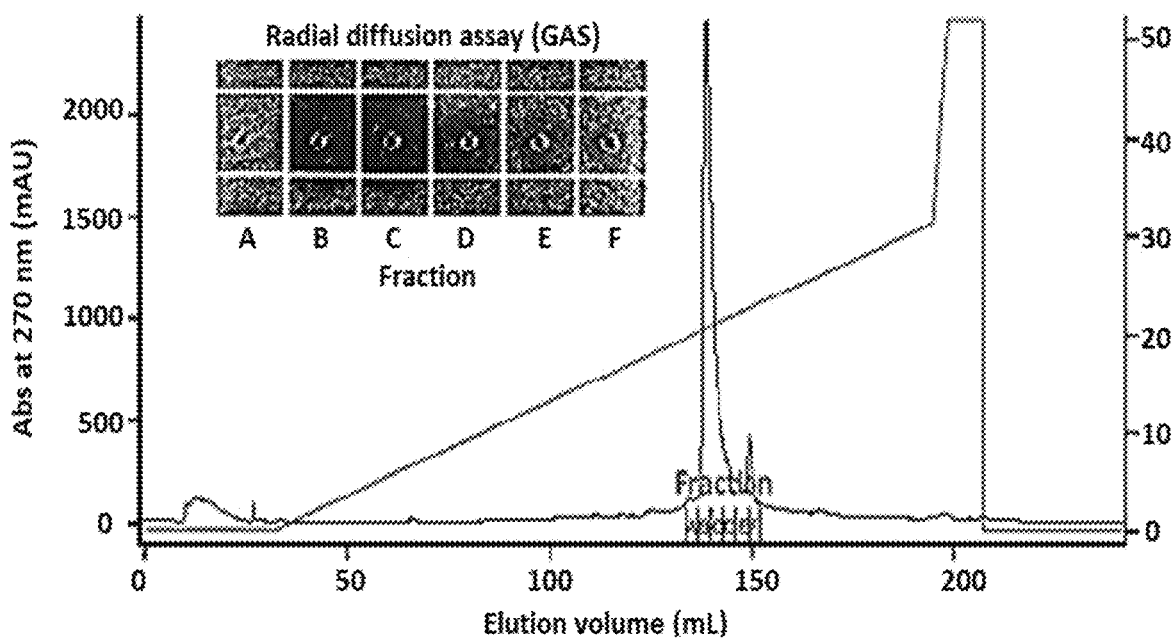
Figure 9:
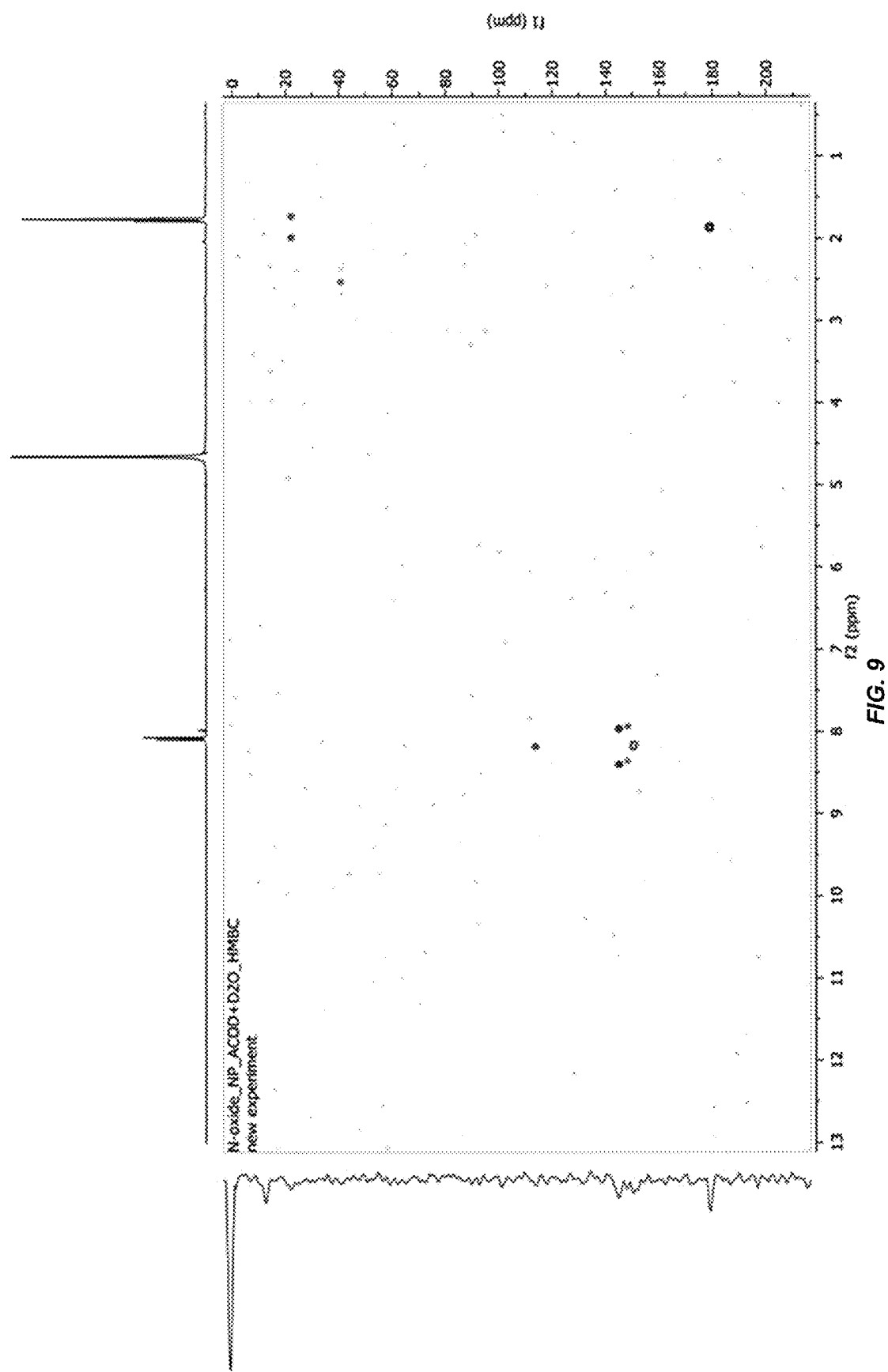
FIG. 9 shows the gHMBC Spectrum (500 MHz) of 6-HAP in AcOD-D2O. The carbon spectrum of 6-HAP was measured indirectly by the gHMBC experiment. The gHMBC spectral data was recorded on a Mercury Pluss 500 (Varian) spectrometer. FID file was processed using MestRenova 8.1 (MestreLab Research). The gHMBC spectrum of 6-HAP in AcOD-D20 (1:5 v/v) revealed five carbon signals in the aromatic region ($\delta C$=113.60, 144.94, 148.17, 150.28, 150.45).

To characterize the molecule(s) responsible for antimicrobial activity secreted from the MO34 strain, the antimicrobial molecule was purified from the conditioned media based on activity against GAS. A single peak was isolated in the last chromatography of 5 purification steps (FIG. 1b). The final yield of purified compound was 7 mg from 6.4 L culture supernatant. This purified fraction showed strong zones of inhibition of GAS growth, and was found only in the culture supernatant of MO34 and MO38 strains, but not in laboratory strains such as ATCC12228 and ATCC1457 strains (FIG. 9). This antimicrobial molecule was heat-stable (FIG. 1c) and protease-insensitive (FIG. 1d), thus suggesting the activity may not be a protein.

Figure 2A:
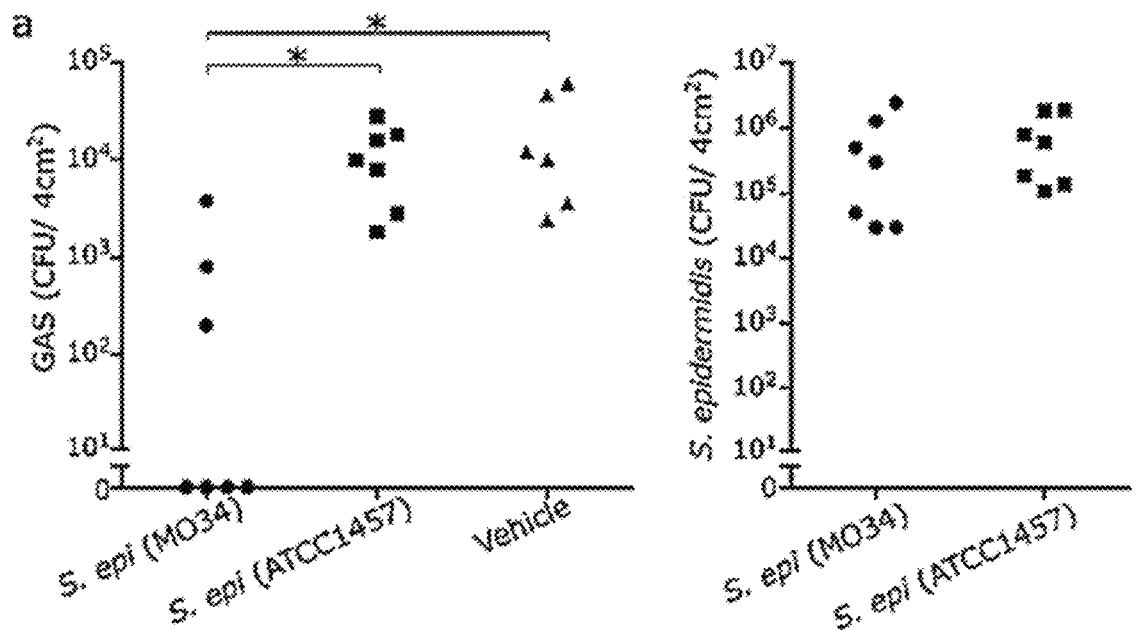
FIG. 2A-B shows colonization by *S. epidermidis* strain producing 6-HAP enhances antimicrobial activity against pathogenic bacteria on skin surface. (a-b) Antimicrobial activity of mouse skin colonized by either *S. epidermidis* producing 6-HAP (MO34), a non-antimicrobial strain (ATCC1457), or vehicle against GAS or methicillin resistant *Staphylococcus aureus* (MRSA) challenge. Mouse dorsal skin was applied with *S. epidermidis* (MO34 or ATCC1457) or PBS (vehicle) for 2 hrs. Pathogens were then applied to the skin surface for 6 hrs. Bacterial survival was measured by swabbing and counting serial dilutions of the swab sample plated on a blood agar plate for GAS (hemolytic) and *S. epidermidis* (non-hemolytic) or a mannitol salt agar with egg yolk for MRSA (mannitol positive: a large yellow colony with egg yolk reaction) and *S. epidermidis* (mannitol negative: a small pink colony without egg yolk reaction). Each dot represents data from an individual mouse. $*P<0.05$ and $**P<0.01$ by Student's t-test.
Figure 2B:
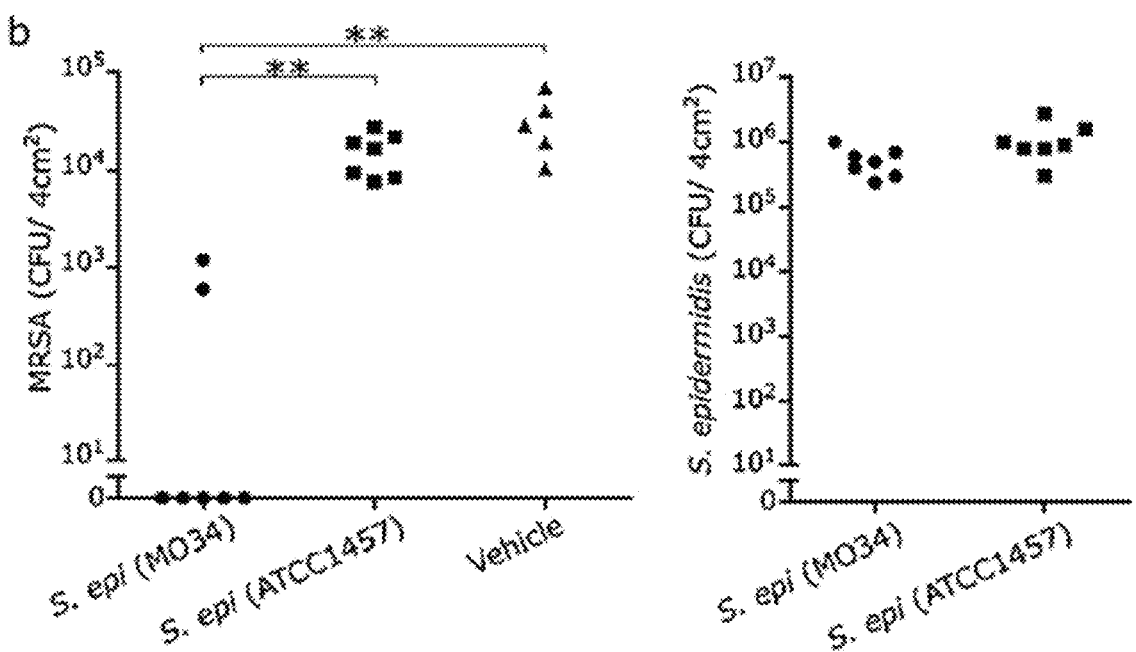

Skin colonization by antimicrobial S. epidermidis strains protects against pathogens. To examine the physiological relevance of colonization by the strains of S. epidermidis that produce non-proteinaceous antibiotic on the skin surface, MO34 or a control strain of S. epidermidis without detectable antimicrobial activity (ATCC1457) (FIG. 1a), or the vehicle alone, was applied to the surface of mouse dorsal skin. 2 hrs after application this site was then challenged with defined amounts of GAS or MRSA. Skin colonized by the antimicrobial strain inhibited growth of the pathogens within 6 hrs, but skin colonized by the control strain or vehicle did not (FIGS. 2a and b). These data suggest that colonization by this antimicrobial S. epidermidis strains is protective against microbial pathogens on the skin surface.

Figure 1C:
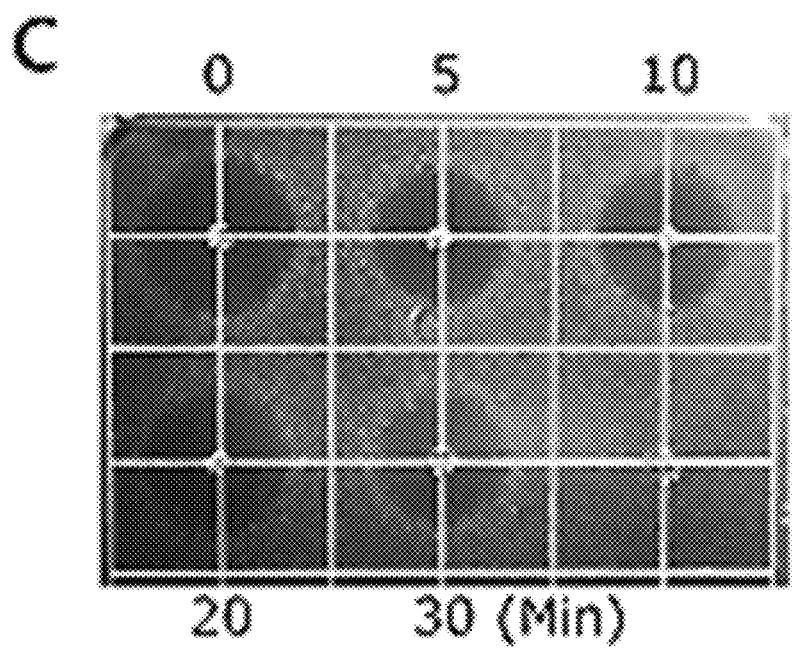
Figure 1D:
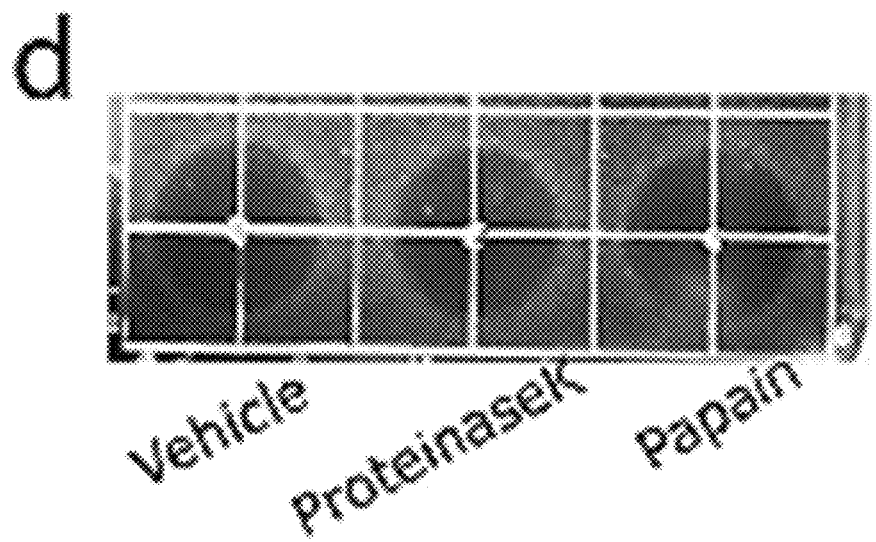
Figure 3F:
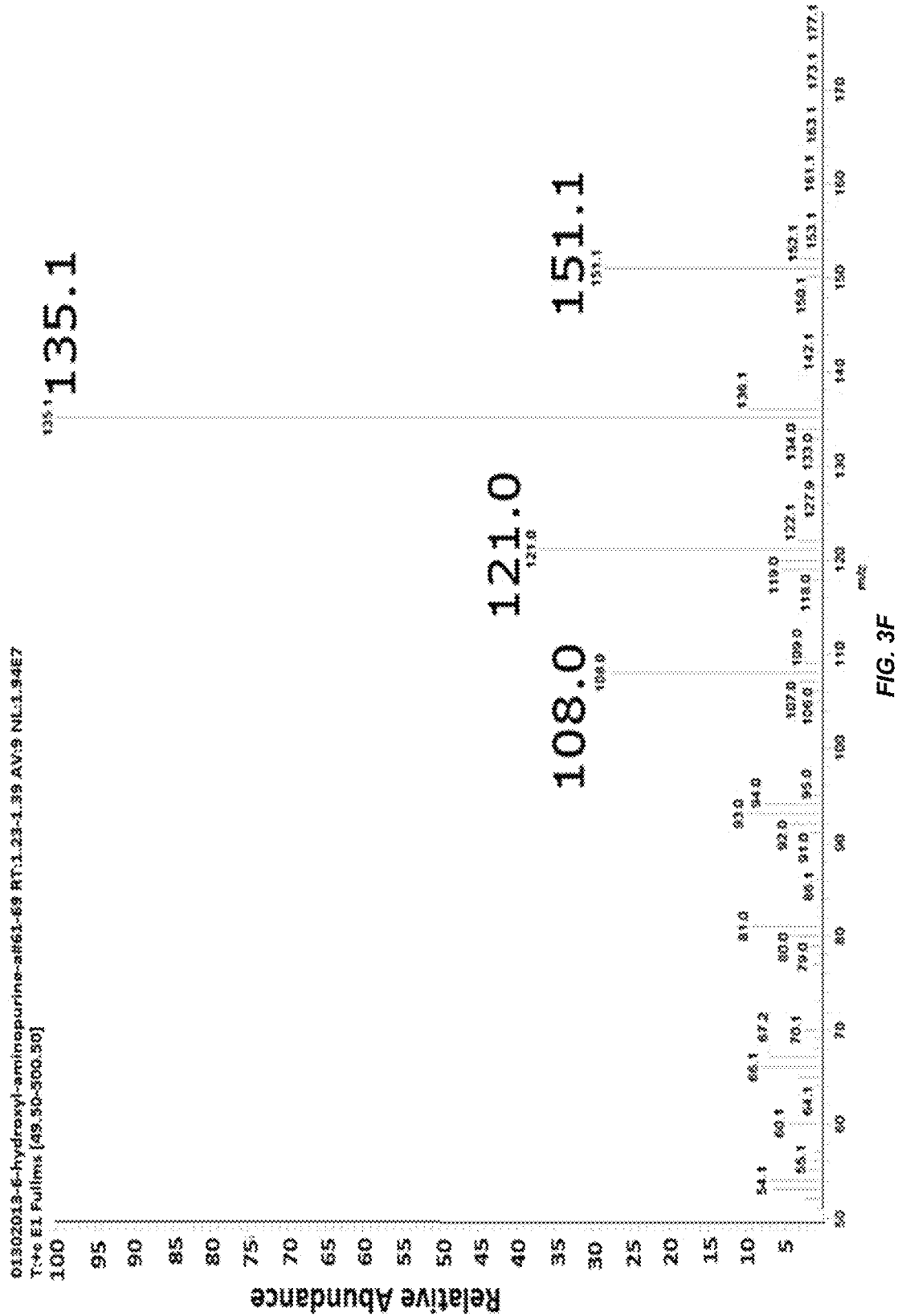
Figure 3G:
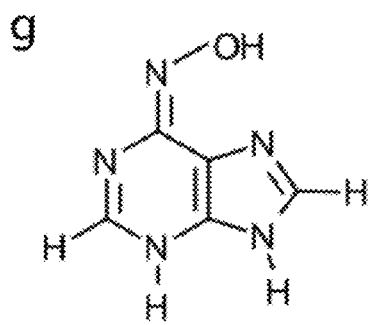
Figure 10:
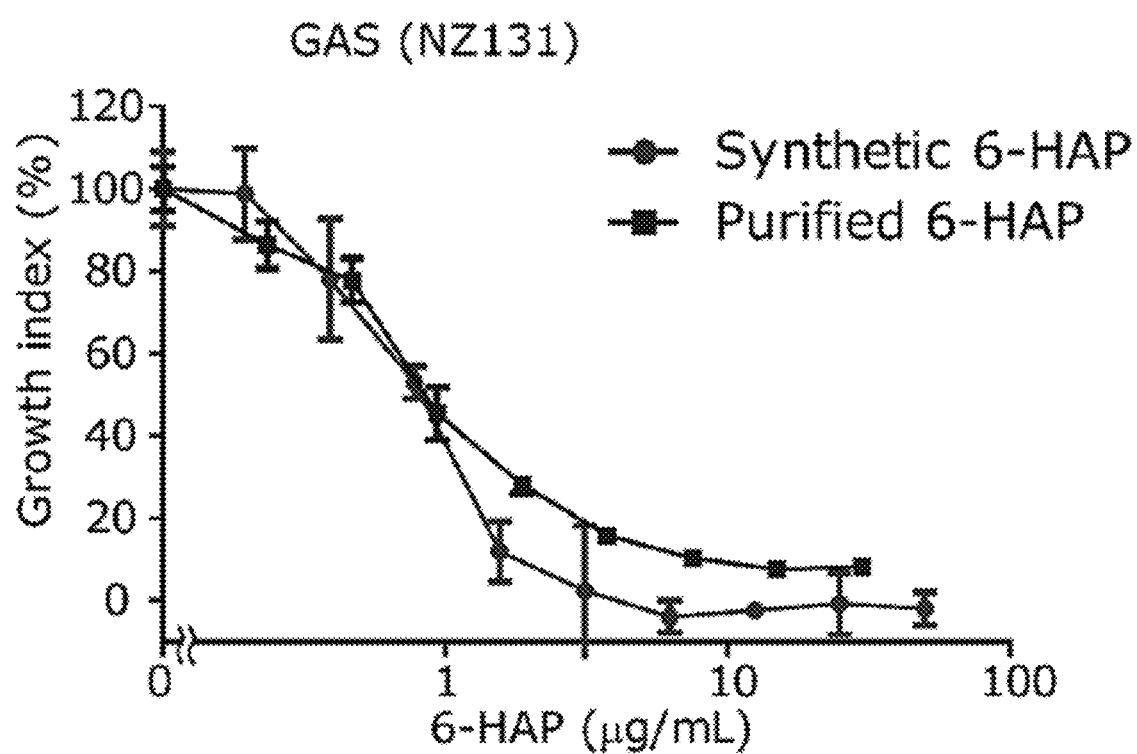
FIG. 10 shows a comparison of antimicrobial activity of natural 6-HAP and synthetic 6-HAP. GAS ($1 \times 10^5$ CFU/mL) were incubated with indicated concentrations of purified 6-HAP or synthetic 6-HAP in THB overnight. Bacterial growth was monitored by measuring OD600 (relative % of growth index).
Figure 11:
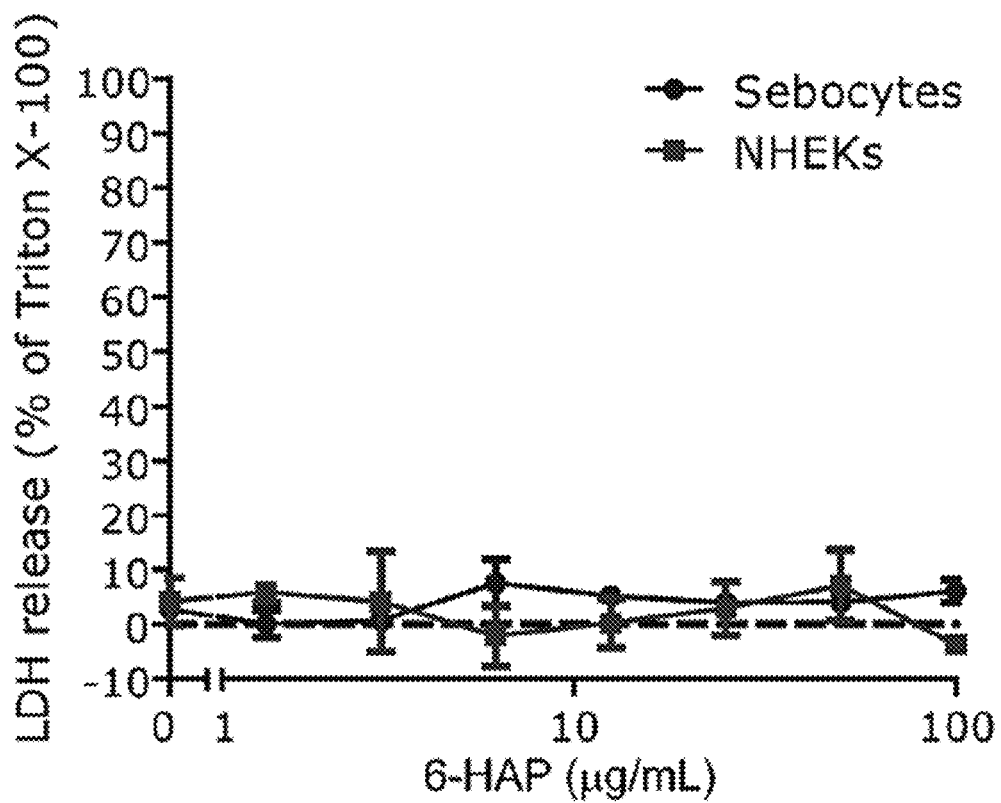
FIG. 11 shows the capacity of 6-HAP to directly disrupt plasma membrane of human keratinocytes and sebocytes. Normal human epidermal keratinocytes (NHEKs) or immortalized human sebocyte cell line (SZ95) ($1 \times 10^5$ cells) were incubated with the indicated concentrations of 6-HAP in Epilife or Sebmed medium, respectively, at 37° C. for 6 hrs. Vehicle (0.5% DMSO) or Triton X-100 (0.1%) was added to achieve 0% or 100% of LDH release, respectively. LDH release was determined with Cytotoxicity Detection Kit (LDH) (Roche, Mannheim, Germany) according to the protocol provided. Data represent mean±SE of three individual experiments.

Structural analyses of antibiotic produced by S. epidermidis. High-resolution electrospray (ES)-mass spectrometry analysis of the purified antimicrobial fraction identified a molecule with a mass of 151.0487, predicting a molecular formula of $C_5H_5N_5O$ (calculated: 151.0489) (FIG. 3a). When S. epidermidis was cultured in the presence of ammonium-$^{15}N$ chloride, the isotope was incorporated into the nitrogen atoms of this molecule, indicating that it was produced via de novo synthesis, but not by fermentation or breakdown of components in the culture media (FIG. 3b). The $^1H$ NMR spectrum of the purified compound displayed two proton signals in the aromatic region (δH=8.19, 8.17), whereas six signals in DMSO-d5 (6H=12.74, 1H; 10.87 0.7H; 9.50, 1H; 8.08, 1H; 7.75, 1H; 7.48, 0.4H) (FIG. 1c). The gHMBC spectrum of purified compound revealed five carbon signals in the aromatic region (δC=113.60, 144.94, 148.17, 150.28, 150.45) (FIG. 10). These NMR chemical shifts suggested the presence of a purine moiety with an additional oxygen atom attached to one of the five nitrogen atoms. Given the chemical formula as $C_5H_5N_5O$, the structure was predicted as 6-N-hydroxyaminopurine (6-HAP). To confirm this predicted structure we performed a chemical synthesis of 6-HAP. The natural compound had an identical chemical shift to synthetic 6-HAP by $^1H$-NMR (FIG. 3d). In addition, the fragmentation profile of natural compound by electron-impact MS (FIG. 3e) also matched that of synthetic product (FIG. 3f). Most importantly, the antimicrobial activity of synthesized 6-HAP against GAS was comparable to that of natural product (FIG. 11). Thus, the combined data indicated that antimicrobial activity produced by this S. epidermidis strain is mediated by 6-HAP (FIG. 3g).

Antimicrobial activity of 6-HAP in vitro. To examine the specificity of 6-HAP for various bacteria, minimal bactericidal concentrations (MBCs) were determined according to dose-dependent killing curves at 24 hrs of incubation in vitro (Table 1). 6-HAP killed or suppressed growth of several major skin pathogens including GAS (NZ131), group B Streptococcus (GBS) (DK23), methicillin-sensitive S. aureus (ATCC35556), methicillin-resistant S. aureus (MRSA) strains (USA300 and Sanger252), Pseudomonas aeruginosa (P. aeruginosa) (ATCC14213) in vitro. In contrast, 6-HAP showed weak antimicrobial activity against Staphylococcus hominis (S. hominis) (ATCC27844) and Escherichia coli (E. coli) (ATCC25922) and Propionibacterium acnes (ATCC6919). S. epidermidis (ATCC12228) was also resistant to 6-HAP.

TABLE 1

MBCs of 6-HAP against indicated bacterial strains.

| Bacteria | Strain | MBC (μg/mL)* |
|---|---|---|
| GAS | NZ131 | 0.156 |
| GBS | DK23 | 0.781 |
| S. aureus | ATCC35556 | 6.25 |
| MRSA | USA300 | 6.25 |
| MRSA | Sanger252 | 0.781 |
| E. coli | ATCC25922 | 50 |
| P. aeruginosa | ATCC14213 | 1.56 |
| S. hominis | ATCC27844 | 12.5 |
| S. epidermidis | ATCC12228 | >50 |
| P. acnes | ATCC6919 | >100 |
| M. luteus | ATCC4698 | 12.5 |

*MBCs were determined as a 3-log reduction of viable bacteria after 24 hour incubation at 37° C. in half strength of MHB in PBS. After incubation, live bacteria were measured by counting CFU after plating serial dilutions on agar plates. The data are representative of three independent experiments.

Figure 4A:
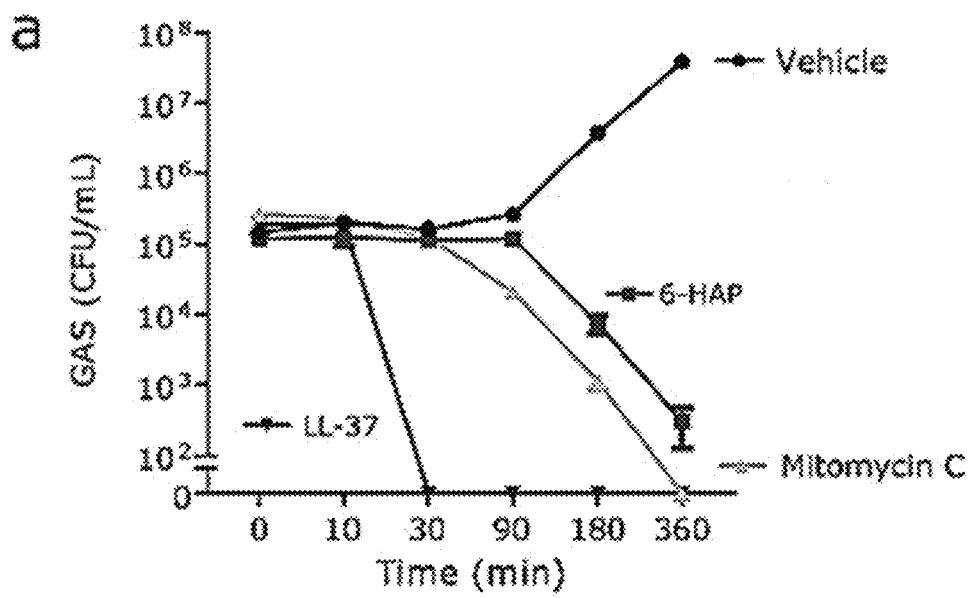
FIG. 4A-G shows 6-HAP is a direct inhibitor of DNA polymerization. (a) Time course killing of GAS in THB containing 6-HAP (25 μg/mL), mitomycin C (5 μg/mL), or LL-37 (10 μM). At each indicated time point, live GAS in the media was measured by counting CFU on an agar plate. The data represent mean±SE of four individual experiments. (b) Membrane permeability of GAS incubated in THB containing 6-HAP (25 μg/mL), mitomycin C (5 μg/mL) and LL-37 (10 μM) for 1 hr. The bacteria with compromised plasma membranes (Red) can be distinguished from those with intact membranes (Green). (c) BrdU incorporation into nascent DNA of GAS after incubation with 6-HAP (25 μg/mL) or mitomycin C (5 μg/mL) in THB containing BrdU (10 μM) for 30 or 60 min. (d) BrdU incorporation into nascent DNA of *S. epidermidis* ATCC12228 after incubation with 6-HAP (25 μg/mL) or mitomycin C (5 μg/mL) in THB containing BrdU (10 μM) for 60 min. The data represent mean±SE of five individual experiments ($*P<0.05$ and $P<0.01$ by Student's t-test vs vehicle control). (e-f) Capacity of 6-HAP to block in vitro DNA extension by Klenow fragment polymerase. Extension reaction was carried out with IRDye800-labeled 18-nt primer (SEQ ID NO:57) and 25-nt template which required adenosine (X=T) or cytidine (X=G) at the initial base for extension (SEQ ID NO:58) (e). Extension reaction was analyzed on a 20% acrylamide gel by electrophoresis (f). (g) Antimicrobial activity of 6-HAP against GAS in the presence of adenine. GAS was incubated in media containing 6-HAP with or without adenine for 20 hrs. GAS survival was measured by counting CFU. The data represent mean±SE of four individual experiments ($P<0.01$ by Student's t-test).
Figure 4B:
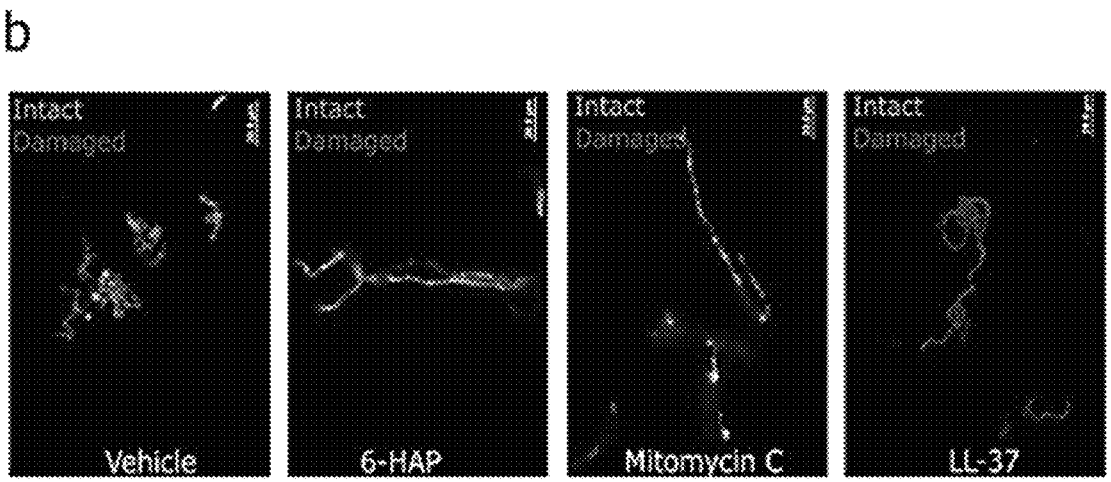
Figure 12A:
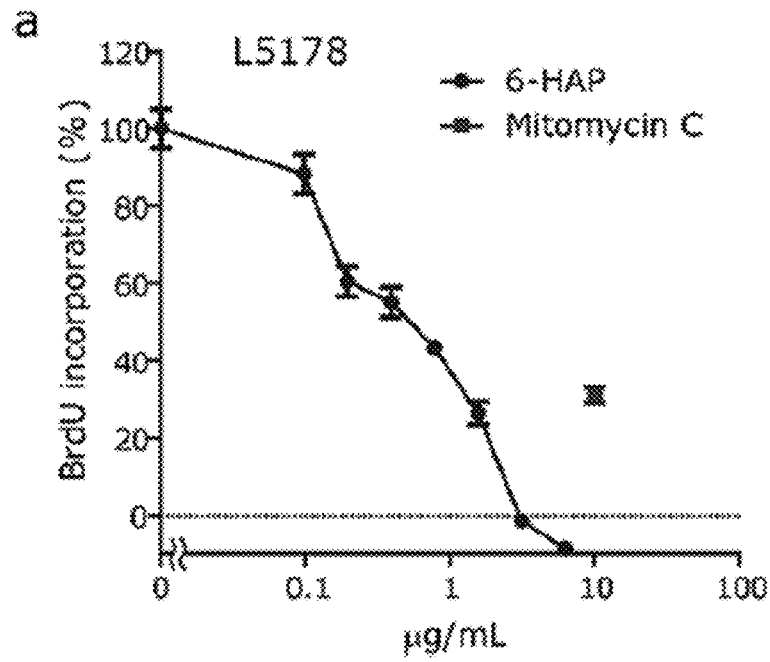
FIG. 12A-C shows 6-HAP exerts antiproliferative activity against tumor cell lines. Proliferative activity of tumor cell line, L5178 (a), YAC-1 lymphoma (b), B16F10 melanoma (c) after 4-hr incubation in suitable media containing indicated concentrations of 6-HAP or mitomycin C (10 µg/mL). Proliferative activity of cells was determined by monitoring BrdU incorporation. The data represent mean±SE of four individual experiments.
Figure 12B:
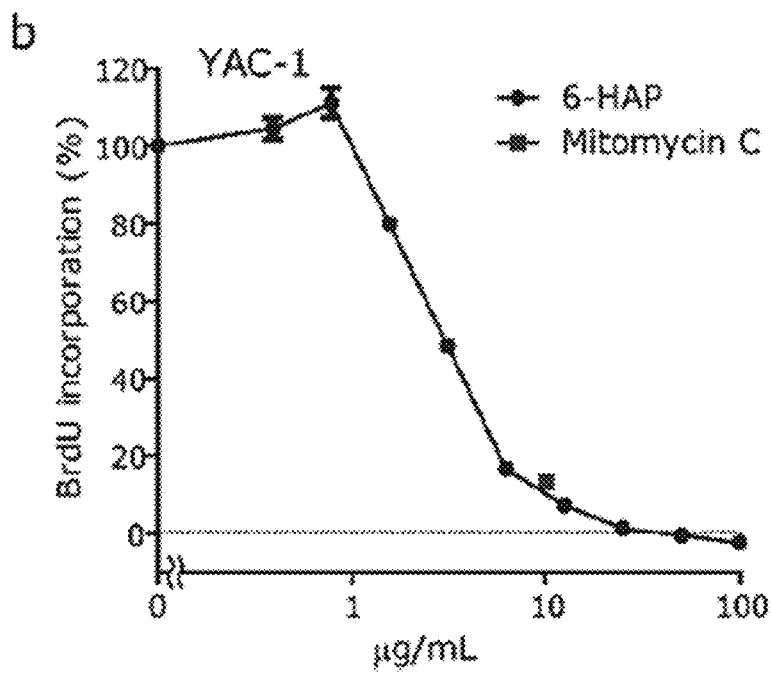
Figure 12C:
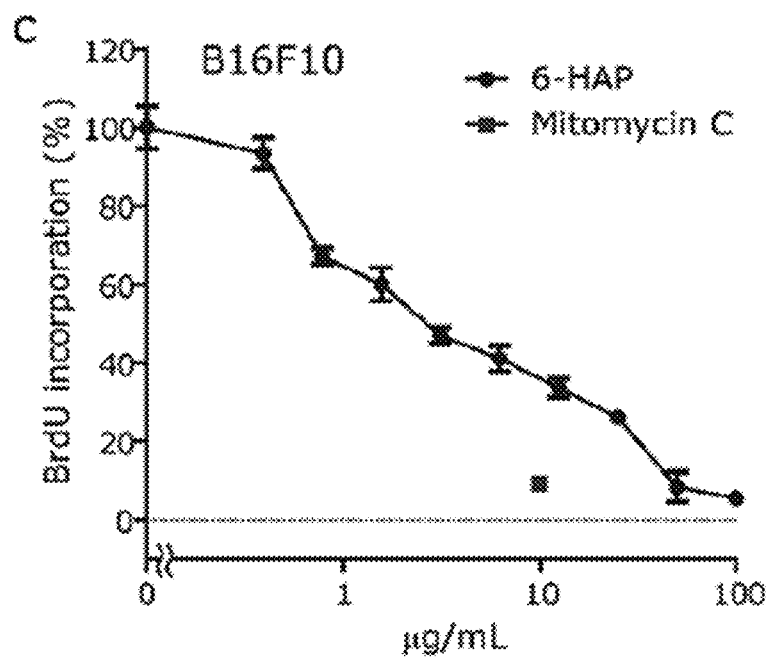

Antimetabolite mechanism of action of 6-HAP. As 6-HAP is structurally similar to adenine, we hypothesized that it inhibited bacterial growth by a different mechanism than membrane permeation used by most other skin surface AMPs produced by the host[2], or bacteriocins previously described from S. epidermidis[17, 18]. To examine this we first compared the kinetics of killing by 6-HAP to those by LL37, a potent human AMP with capacity to disrupt membranes, and mitomycin C, a known DNA synthesis inhibitor. Growth of GAS over time was inhibited by 6-HAP at a rate similar to mitomycin C but slower than LL37 (FIG. 4a). LL37 disrupted permeability of the GAS membrane after 1-hr incubation, whereas 6-HAP and mitomycin C did not (FIG. 4b). 6-HAP also did not directly affect plasma membrane permeability of normal human epidermal keratinocytes (NHEKs) or the human sebocyte line SZ95 after 6-hr incubation (FIG. 12).

Figure 4C:
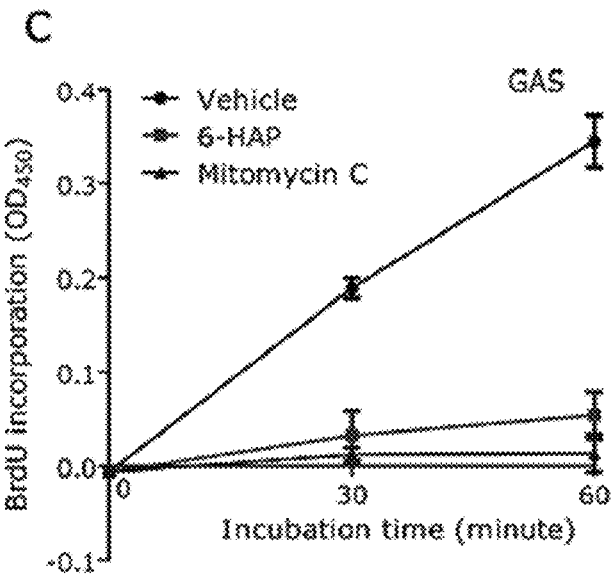
Figure 4D:
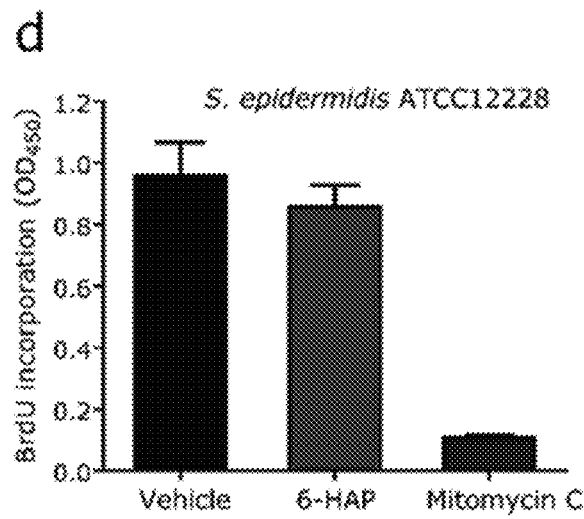
Figure 4E:
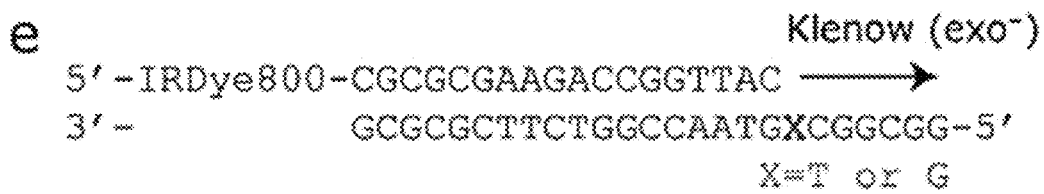
Figure 4F:
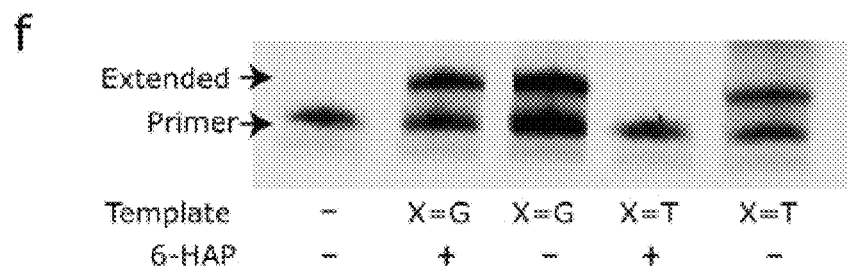
Figure 4G:
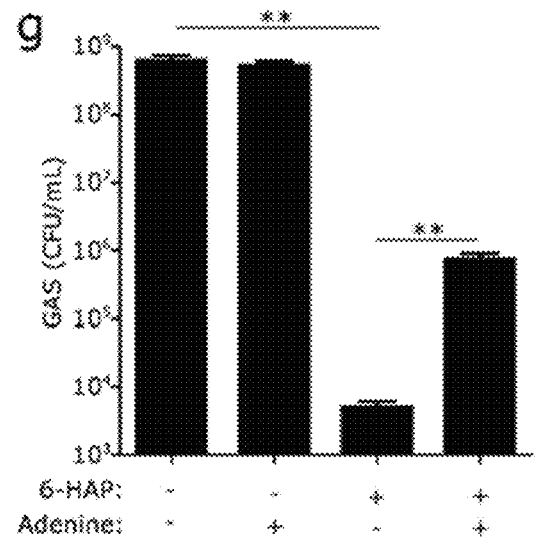

We next assessed the effect of 6-HAP on DNA synthesis. Significant suppression of BrdU incorporation into the genomic DNA of GAS could be observed in a time-dependent manner (FIG. 4c). However, 6-HAP did not affect BrdU incorporation in S. epidermidis (FIG. 4d). To directly examine the action of 6-HAP on DNA extension in a cell free system, 25-bp templates and matching 18-bp fluorescence primers were designed to measure DNA extension in vitro by Klenow (exo) DNA polymerase (FIG. 4e). In the presence of 6-HAP, we observed synthesis of the expected extended DNA product when the template required cytosine (X=G), but lack of extension when adenosine was required (X=T) (FIG. 4f). These data suggest that 6-HAP inhibits DNA synthesis by interfering with adenosine-thymidine base pairing. Indeed, addition of excessive adenine partially decreased antimicrobial activity of 6-HAP against GAS (FIG. 4g).

Figure 5A:
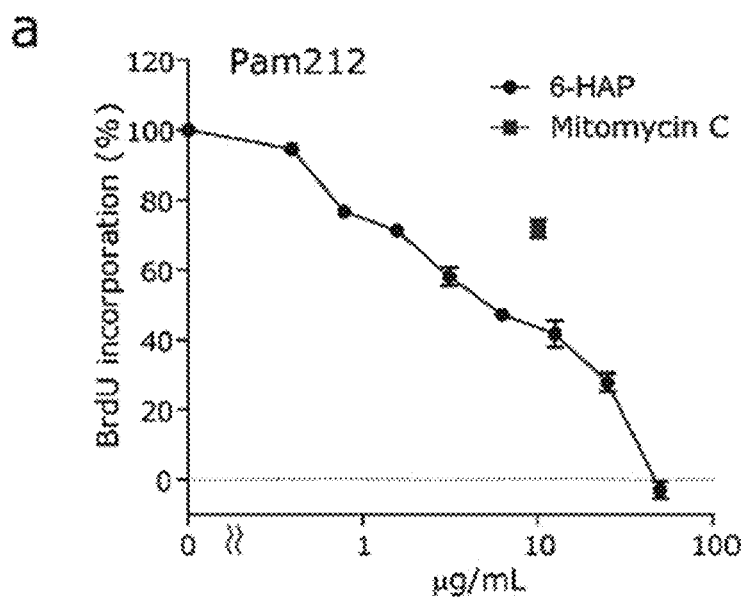
FIG. 5A-E shows mARC2 responsible for selective antiproliferative activity of 6-HAP. (a-b) Selective antiproliferative activity of 6-HAP against Pam212 squamous cell carcinoma, but not against normal keratinocytes. BrdU incorporation into Pam212 cells (b) or NHEKs (b) after 4-hr or 24-hr incubation, respectively, in suitable media containing indicated concentrations of 6-HAP or mitomycin C (10 μg/mL) (a). (c) Expression of mARC1 and mARC2 in NHEKs, squamous cell carcinoma (Pam212), melanoma (B16F10) and lymphoma cell lines (L5178). To compare relative expression level in each cells, data was shown as relative to GAPDH expression. (d) Expression of mARC1 and mARC2 in NHEKs treated with control siRNA, mARC1 siRNA and mARC2 siRNA. (e) Effect of gene silencing with mARC1 and mARC2 siRNA on sensitivity to 6-HAP in NHEKs. NHEKs treated with each siRNA were incubated for 48 hrs and then incubated with 10 μg/mL of 6-HAP for 24 hrs.
Figure 5B:
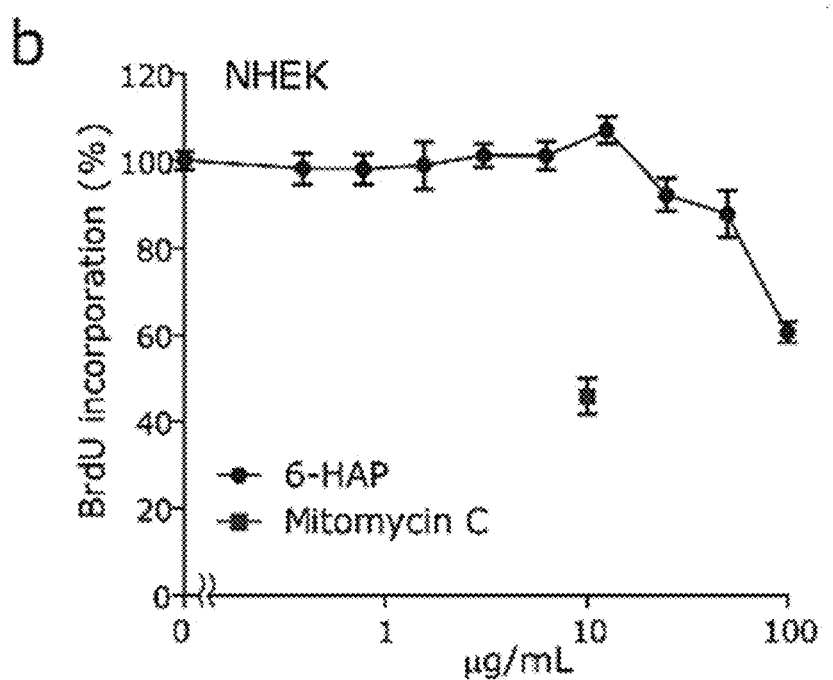
Figure 13:
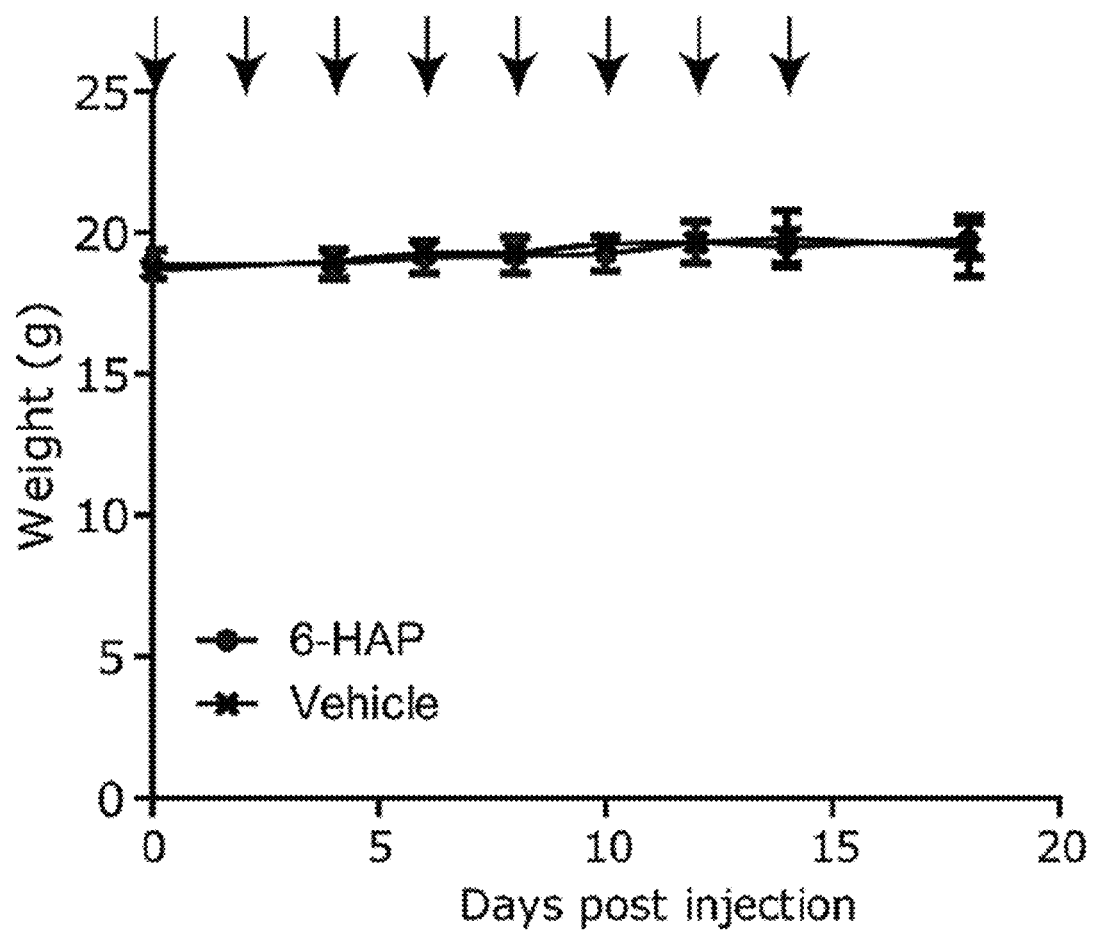
FIG. 13 shows Systemic toxicity of 6-HAP in mice. C57BL6 mice (8 week female) were intravascularly administrated with 6-HAP (20 mg/kg) or with an equal volume of vehicle (2.5% DMSO in 0.9% NaCl) every 48 hours for 2 weeks (Arrows). To observe toxicity of 6-HAP, mouse weight was determined at indicated time points. Data represent mean±SE of 10 mice.

Mechanism for selective antiproliferative activity of 6-HAP. Given the capacity to inhibit DNA synthesis, we next explored the anti-proliferative effects of 6-HAP on mammalian cells. 6-HAP inhibited BrdU incorporation in several tumor cell lines, including Pam212 squamous cell carcinoma (FIG. 5a), B16F10 melanoma and L5178 and YAC-1 lymphoma (FIG. 13). In contrast, BrdU incorporation in normal human keratinocytes (NHEK) was not affected by 6-HAP until a very high dose (100 μg/mL) (FIG. 5b). The mechanism of selective inhibition of mammalian cell lines, as well as selective inhibition of bacterial pathogens, is currently unknown and a subject of ongoing investigation.

Because some nucleobase analogs exert mutagenic activities due to their misrecognition of wrong bases, mutagenic activity of 6-HAP was determined by detecting mutagenic events at the thymidine kinase (tk) locus of L5178Y tk$^{+/-}$ mouse lymphoma cells. This sensitive assay of mutagenic activity did not detect a difference between 6-HAP compared to vehicle, whereas treatment with methyl methanesulfonate was a positive control for the assay and did induce a high mutation frequency. These data are consistent with a lack of association between S. epidermidis and neoplastic transformation despite the chronic presence of this molecule as a product of the normal commensal microbiome.

Figure 5C:
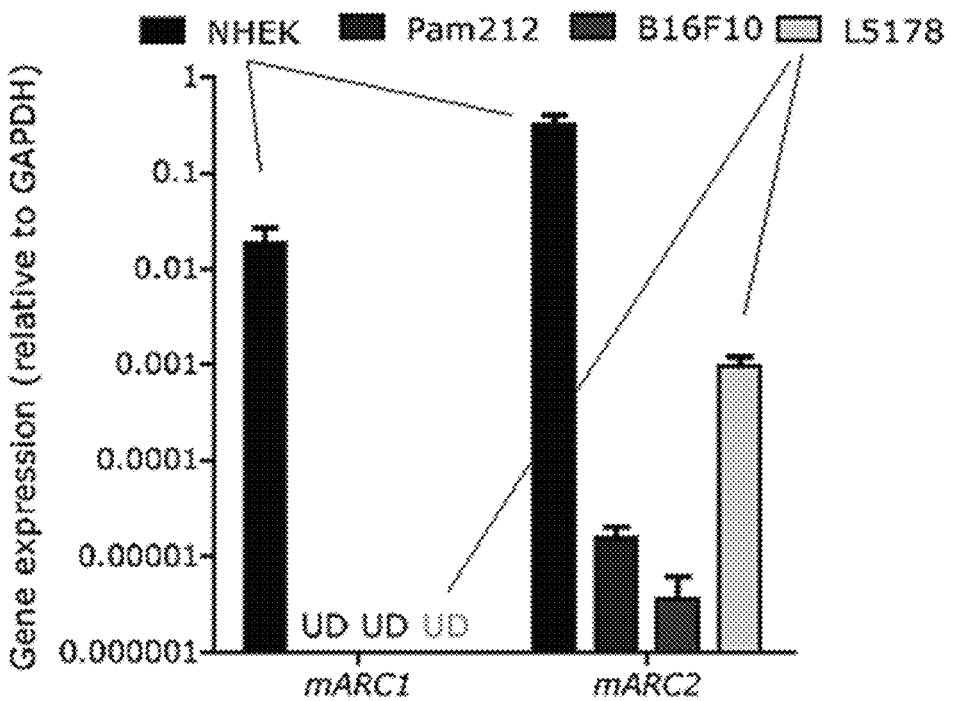
Figure 5D:
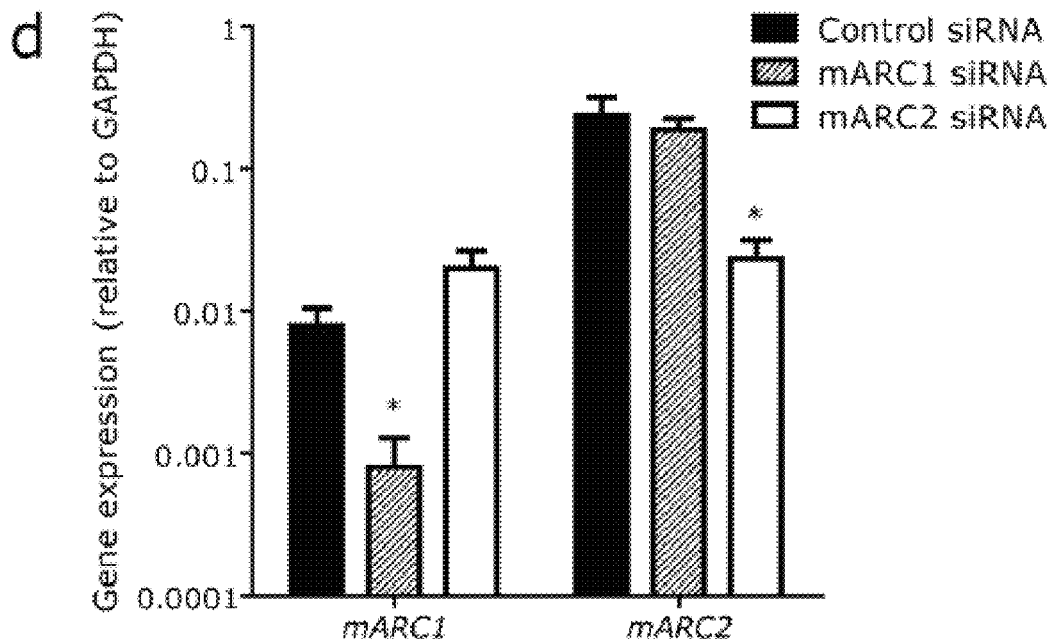
Figure 5E:
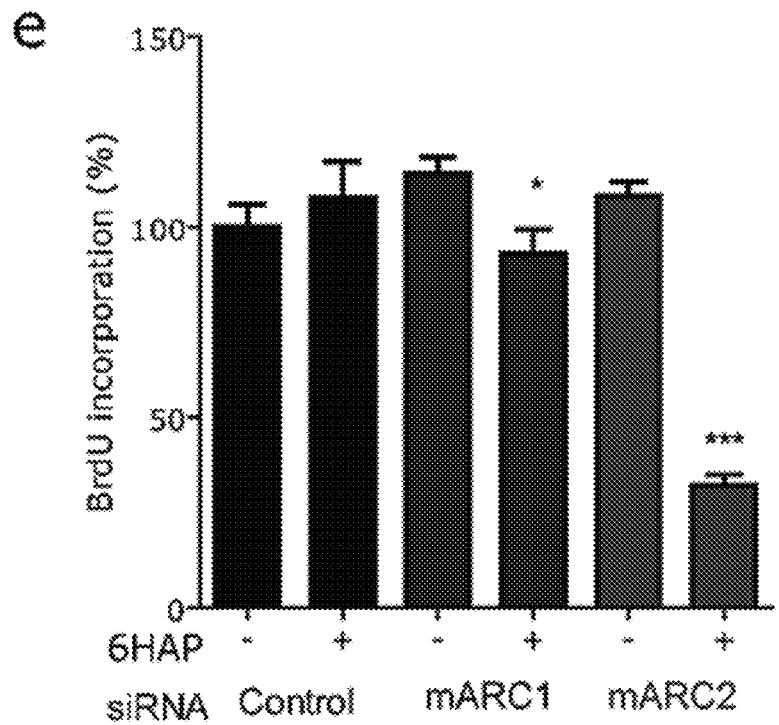

In mammalian cells, mitochondrial monoxide reducing components (mARC) 1 and 2 have shown to be capable of reducing N-hydroxylated nucleobase analogs to canonical nucleobases. Relative expression level of mARC1 and mARC2 was much higher in NHEKs than that in cancer cell lines, such as Pam212, L5178 and B16F10 (FIG. 5c). Thus, we hypothesized that mARCs may contribute to detoxification of 6-HAP in NHEKs. Gene silencing with siRNA significantly decreased expression of mARC1 and mARC2 in NHEKs (FIG. 5d) and increased cellular sensitivity to 6-HAP, suggesting that mARC2 protects cells from 6-HAP.

Figure 6A:
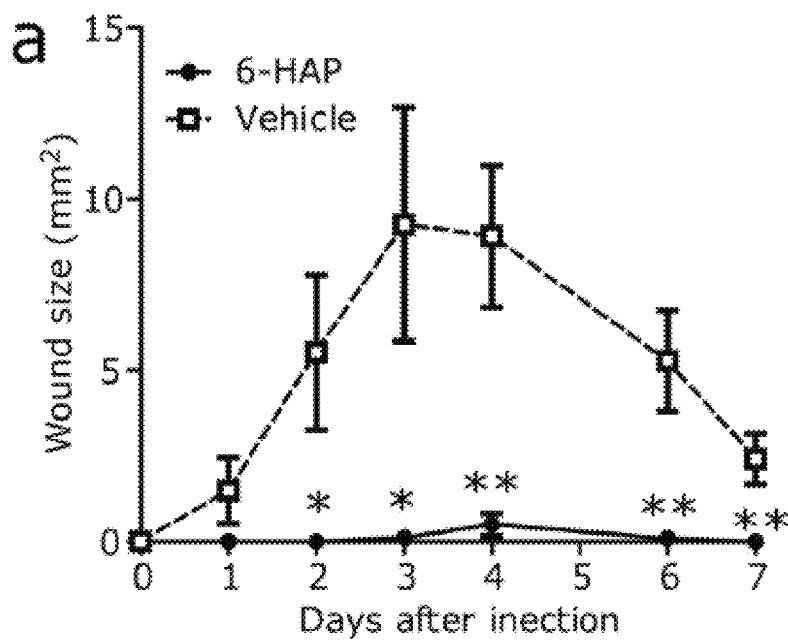
FIG. 6A-E shows 6-HAP improves deep skin infection and slows growth of B16 melanoma in mice. (a-c) Effect of a single intravascular injection of 6-HAP on skin infection by GAS. The size of the infected lesion was measured by Image-J software (a). Representative images of infected skin (arrow) of mouse treated with 6-HAP or vehicle at Day-1 and Day-3 post infection are shown in (b). Infected skin was removed 24 and 72 hrs after bacterial injection and homogenized in PBS (c). CFUs were enumerated by plating serial dilutions of the homogenate on an agar plate. The data represent mean±SE of eight individual experiments ($*P<0.05$ and $**P<0.01$ by Student's t-test vs vehicle control). (d-e) Effect of repeated intravascular administrations with 6-HAP on growth of melanoma in mice. The data represent mean±SE of 10 individual experiments ($*P<0.05$, $P<0.01$ and $*P<0.001$ by Student's t-test vs vehicle control) (d). Representative images of tumor (broken line) in mouse treated with 6-HAP or vehicle at Day-9 and Day-13 are shown in (e).
Figure 6B:
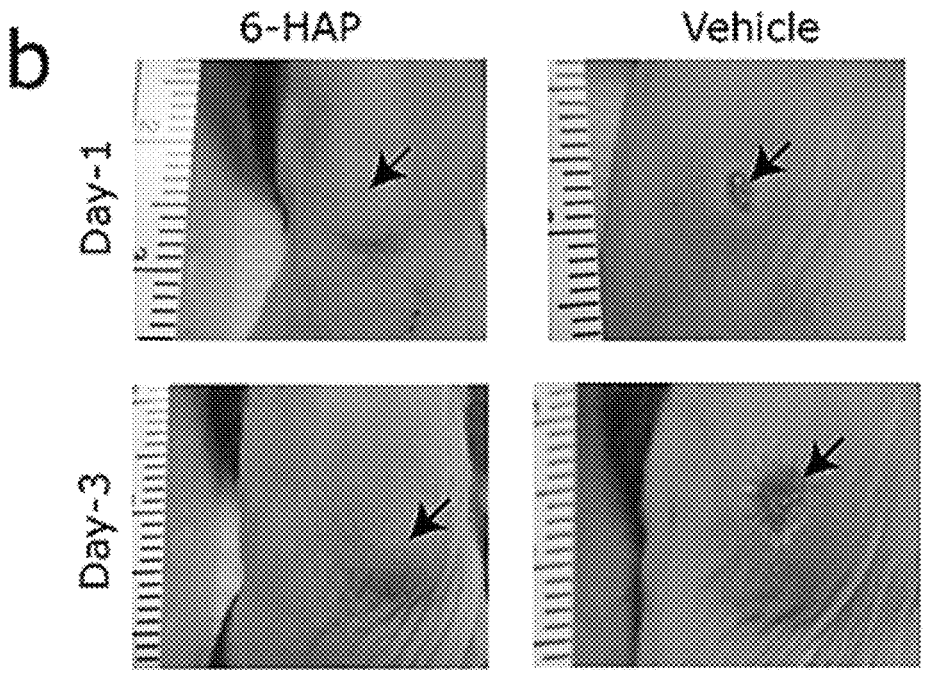
Figure 6C:
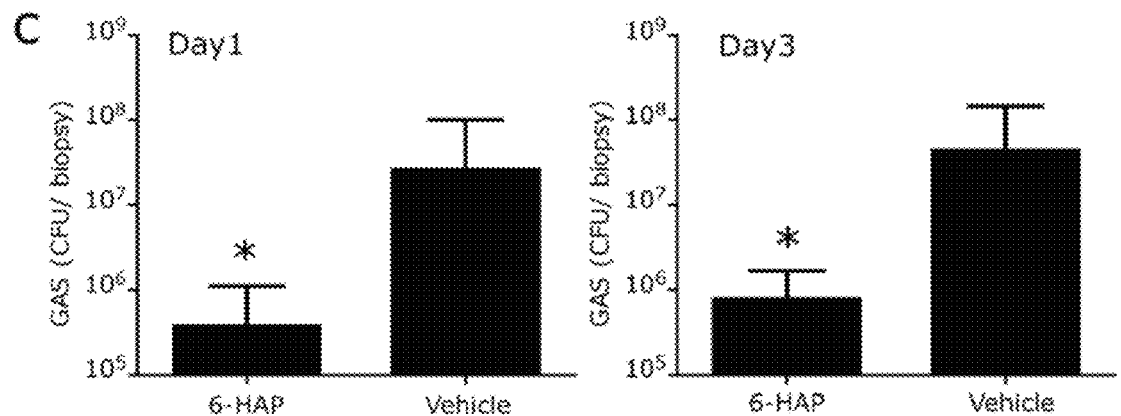

Effect of systemic administration with 6-HAP on skin infection and melanoma growth in mice. As 6-HAP exhibited both antimicrobial activity and antiproliferative activity in vitro, we next explored the systemic activities of this compound in vivo. Repeated intravenous injections of mice with 6-HAP at a dose of 20 mg/kg every 48 hrs for 2 weeks resulted in no apparent toxic effects as assessed by visual appearance, behavior or change in weight (FIG. 14). This response was consistent with prior results in seen in FIG. 4i demonstrating a lack of inhibition of the proliferation of rapidly dividing normal keratinocytes. Thus, given the apparent lack of toxicity, the effect on deep tissue infection was tested by intravenously injecting the non-toxic dose of 6-HAP (20 mg/kg) into a mouse model of GAS deep skin infection. A single injection of 6-HAP after inoculation of GAS significantly suppressed the clinical lesion size (FIG. 6a-b) and GAS survival (FIG. 6c) in mice.

Figure 6D:
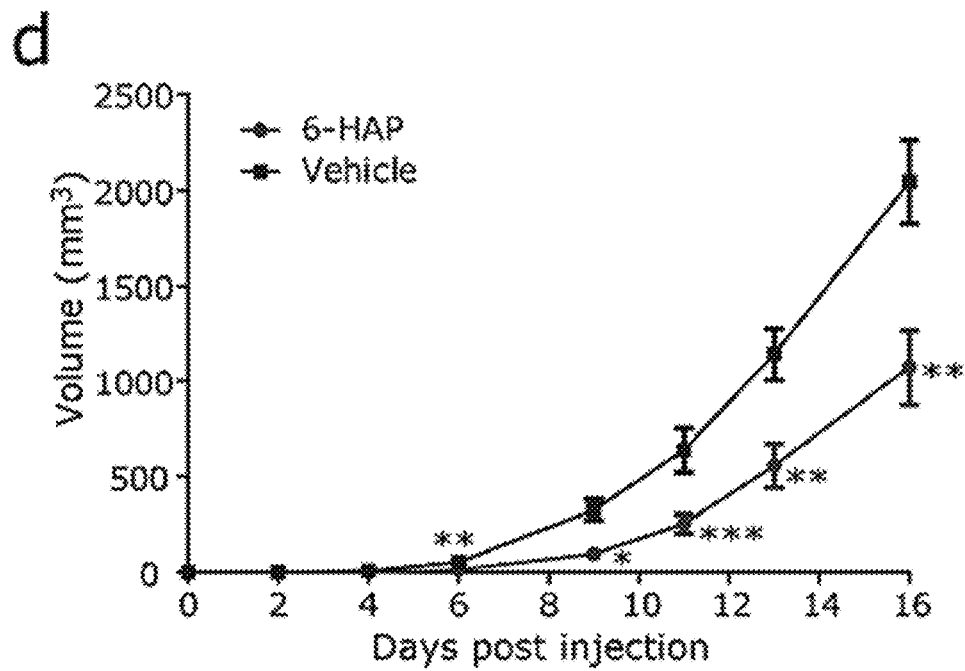
Figure 6E:
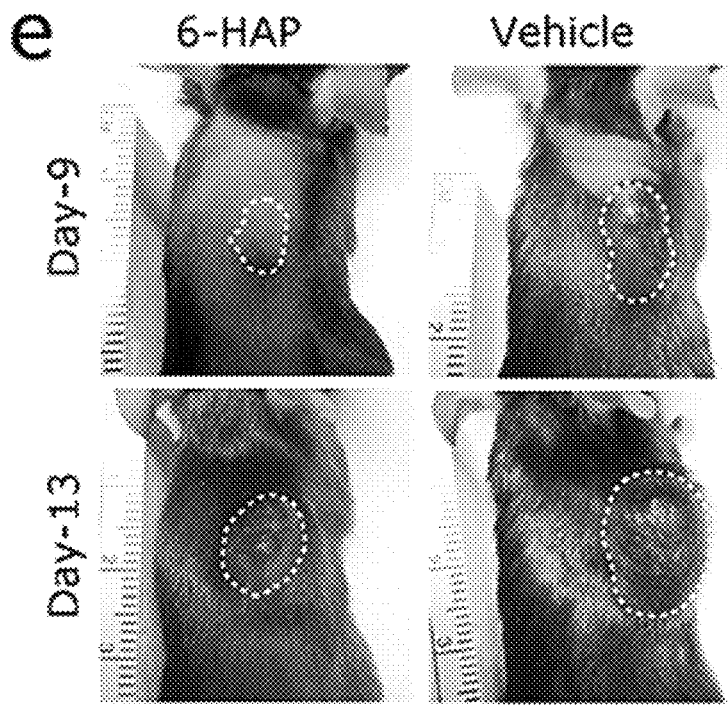

Similar to our experiments to evaluate the antibiotic action of 6-HAP, we also examined the activity of 6-HAP to inhibit tumor growth in vivo. Mice were intradermally inoculated with B16F10 melanoma, followed by intravenous injection of 6-HAP (20 mg/kg) or vehicle every 48 hrs for 2 weeks. Tumor size of this aggressively growing tumor was suppressed by >60% in mice receiving 6-HAP compared to those received injections with vehicle (FIG. 6d-e).

Figure 7A:
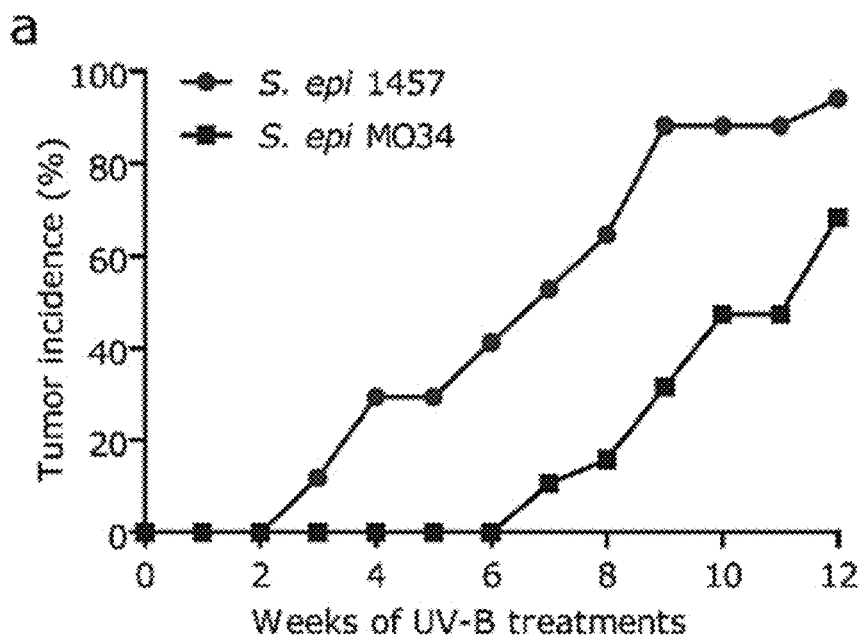
FIG. 7A-H shows *S. epidermidis* strains producing 6-N-hydroxyaminopurine suppress UV-induced skin tumor formation in SKH-1 hairless mice. (a-d) Effect of colonization by *S. epidermidis* MO34 producing 6-HAP on tumor incidence (a) and number (b) in SKH-1 hairless mice treated with DMBA, followed by UV-B irradiation at 180 mJ/cm$^2$ twice a week. *S. epidermidis* ATCC1457 was used as a control strain that does not produce 6-HAP. Tumor incidence and tumor number in each mouse were recoded every week. The data represent mean±SE of 19 mice. Representative images of UV-induced tumor formation in mouse treated with *S. epidermidis* ATCC1457 (c) or MO34 (d) at week-12 are shown. (e-f) A representative H&E staining of UV-induced skin tumor or skin obtained from SKH-1 mice colonized by *S. epidermidis* 1457 (e) or MO34 (f), respectively, treated with UV-B for 12 weeks. (g-h) Immunostaining for *S. epidermidis* and keratin-14 in the UV-induced tumor or skin of SKH-1 mice treated with *S. epidermidis* ATCC1457 (g) or MO34 (h), respectively.
Figure 7B:
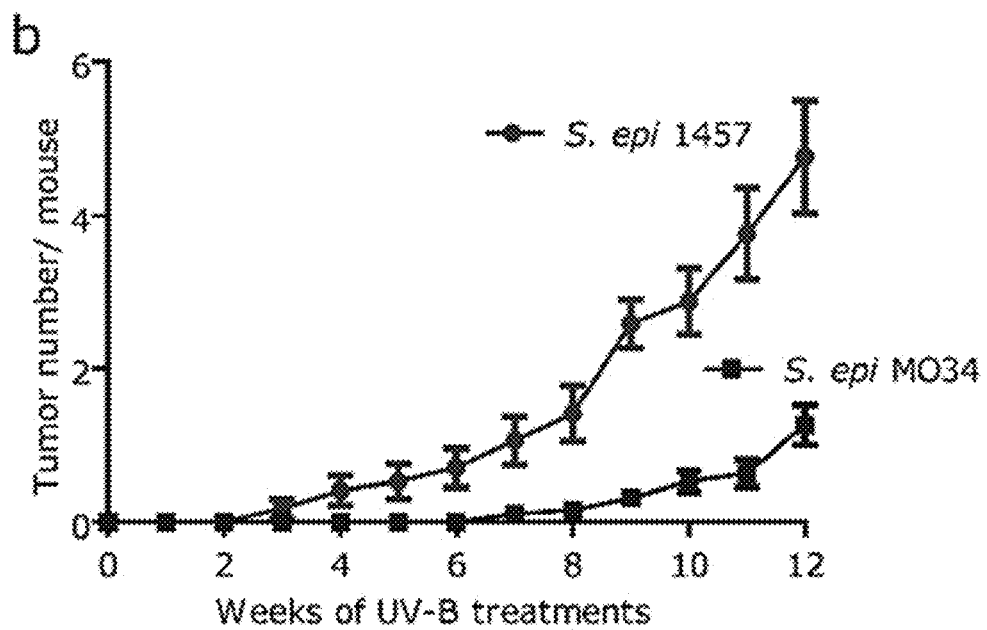
Figure 7C:
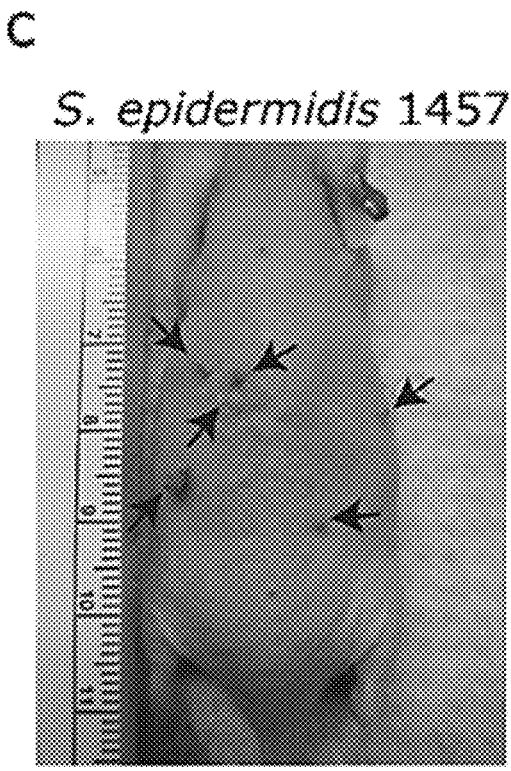
Figure 7D:
Figure 7E:
Figure 7F:
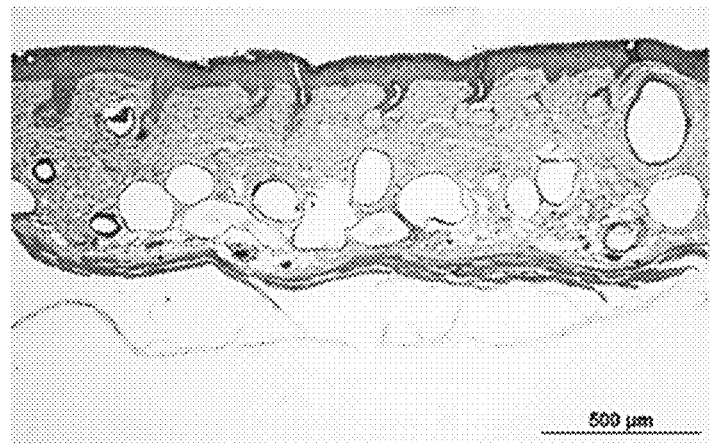
Figure 7G:
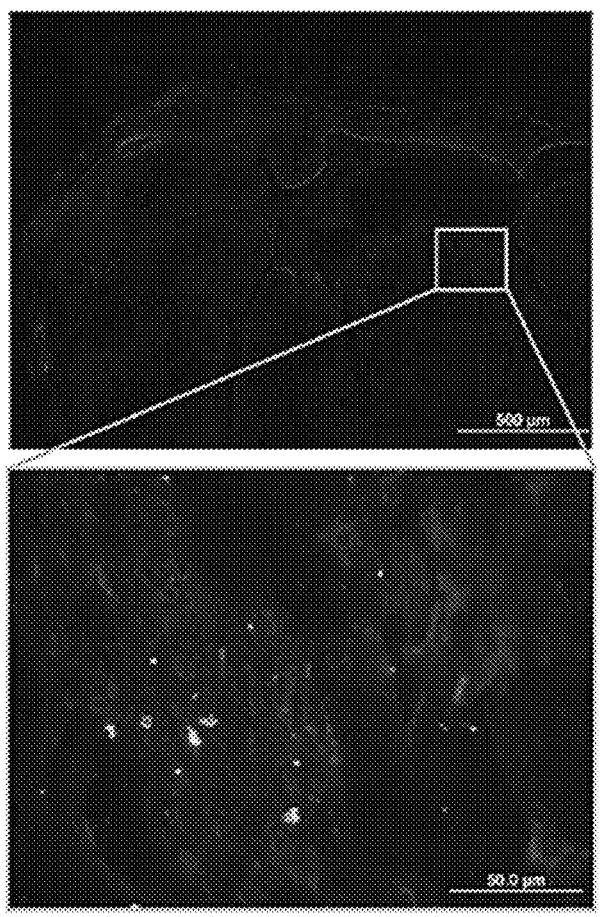
Figure 7H:
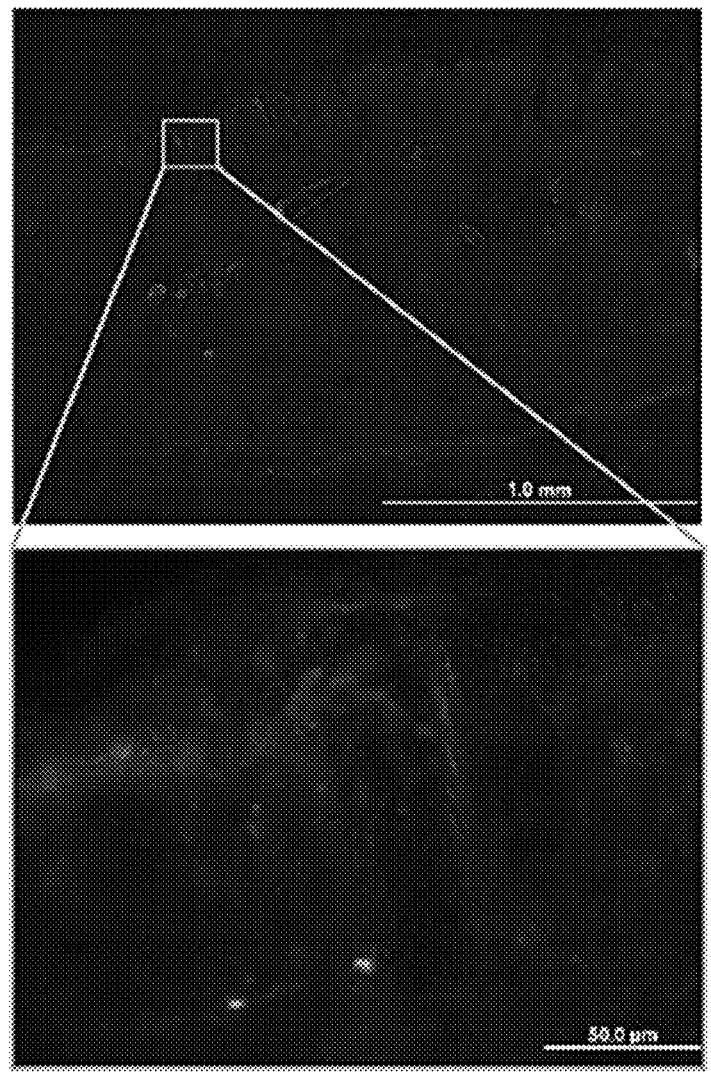
Figure 8A:
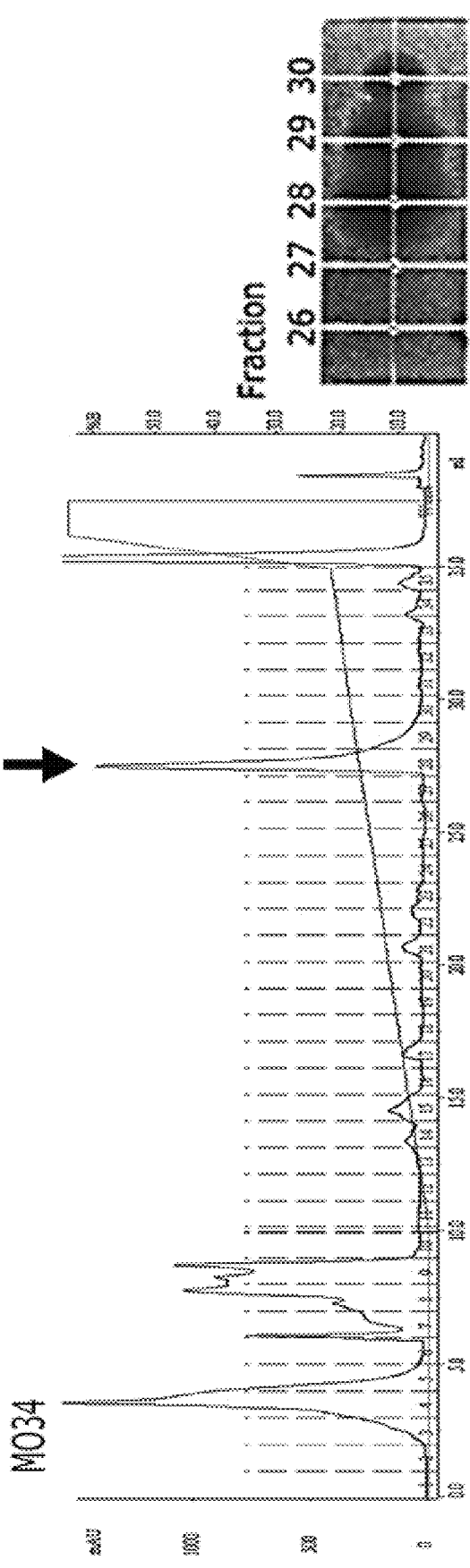
Figure 8B:
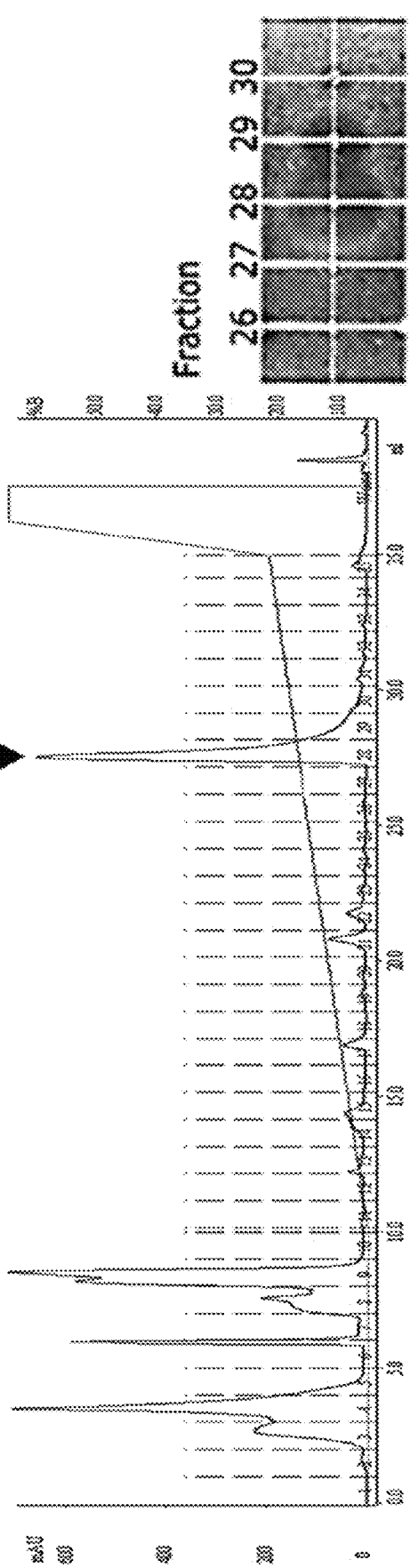

Effect of skin colonization by S. epidermidis on UV-induced skin tumor formation. Given the data that 6-HAP inhibited the proliferation of several tumor lines in vitro and in vivo, we hypothesize that colonization by strains of S. epidermidis producing 6-HAP is protective against skin tumor formation induced by UV-B irradiation. To address this hypothesis, two-stage carcinogenesis model was employed. SKH-1 hairless mice were treated with DMBA for 1 week, followed by UV-B irradiation twice a week and epicutaneous application with S. epidermidis 6 times a week. Mice inoculated with S. epidermidis ATCC1457, a non-6-HAP strain, elicited 88% tumor incidence at 9 weeks (FIG. 7a) and multiple tumor formations by 12 weeks (FIG. 7b-c). In contrast, repeated application with S. epidermidis MO34 strain producing 6-HAP significantly decreased tumor incidence and numbers (FIG. 7a-b, d). Histopathogenic examination distinguished that SKH-1 mice colonized by control strain developed squamous papillomas (FIG. 7e). The papilloma development was successfully inhibited by epicutaneous application with 6-HAP strain (FIG. 7b, d, f). These data suggest that 6-HAP produced by S. epidermidis contributes to the resistance to neoplasm formation on the skin surface. In addition, both strains penetrate tumor and dermis of skin (FIG. 7g-h), suggesting that the direct interaction between S. epidermidis and tumor cells or skin residing cells. This data is consistent with our previous observations that a part of skin microbiome can penetrate the epidermal barrier of human skin.

S. epidermidis strains producing 6-HAP in human skin. 6-HAP was detected by HPLC of culture supernatant from two distinct clinical isolates of S. epidermidis. To further explore the frequency of 6-HAP production in human commensal S. epidermidis stains, whole-genome sequencing of the MO34 strain was performed and used for analysis of existing metagenomic data sets of the human skin microbiome. Sequence analysis frequently identified S. epidermidis strains similar to the 6-HAP-producing isolate within the human skin microbiome but detected similar strains at a different frequency at distinct body sites.

TABLE 2

28 marker genes that are present in 6-HAP-producing S. epidermis strains but not in any of the other strains.

| gene ID | Hypothetical Role | Sequence |
|---------|-------------------|----------|
| peg.44# | hypothetical protein | SEQ ID NO: 1<br>atgagtgctgttttattatcagcaattagtccaacggcaagtgtaaatgaatcaataga<br>attgtacaagtcagttagcaagtcgaatatagaaattgaaaaagataataagactttag<br>atgattcgttttaa |
| peg.45# | hypothetical protein | SEQ ID NO: 3<br>atgattcgttttaaaatcctaaatatggtaactgaacagactattaatagthaccatata<br>atcttaaagaagggacttcagaaagaattggtggttggttactgtaaaaaaggattaa |
| peg.131# | YefM protein (antitoxin to YoeB) | SEQ ID NO: 5<br>atgactgttaaatcctattcatatgtacgtgaacatgcaaagacatgattaataaagtta<br>atgatgatagcgatacgataacaattacaacaaaagaccgtaatgcagttatgatgtc<br>agaagataattataatgaaataatggagacactatacttgcaacaaaatcctgccaat<br>gcaaaatatttatcagaatccattgaaaacctagaacgtggtaatataaaaactaagg<br>atattttgatataa |
| peg.139# | antirepressor [Staphylococcus epidermidis] | SEQ ID NO: 7<br>atgttagataaagaaaagcaaaaagaagctatgcctattattcaaggagagtacaaa<br>tcagatgaaccaattaattacattaaagcaaacacaatcccaaacaaagctacatcaa<br>cgacttaggatatgaaaagatgattagtaaagaggctatgacgccagaaatgttaga<br>ggttcgtcaaataattcttaatgatgtggtaaagctcacagaatcaatgaatcaatttaa<br>acttgatattaaagttagtaaagtaatttatgacaaatatggggtgagataa |
| peg.140# | antirepressor [Staphylococcus epidermidis] | SEQ ID NO: 9<br>atgattaaacaaattttcaatgataaagaaattcggtttatcgaaaaagaagatgaatat<br>tgggcagtagctggagatgtggcaaaggtattggggtactcacatacaccacacat<br>gactagattattagatgaatcagaaaaggctgtccataatgtggtcaccgttaaaggt<br>aaacaaaatgctgtgatcatattagaaataggtatttatgaagctatttggaatagtaga<br>agagatgaagctcaagaattttag |
| peg.141# | XRE family transcriptional regulator [Staphylococcus epidermidis] | SEQ ID NO: 11<br>gtggttaacaacgttaaaagaatacgaaaaaataaaaaaattaccattactgaattaa<br>gtagaaaaagtgggataagcagaacaactatatacaaattagaatctcaaaaatcaa<br>atcccagcttggaaaccattcaaaaaatatcttctggtttagatgaaaaaccagaaaa<br>aatttttaacctcattgttattcaagaattacaaaaggagccttaa |
| peg.142# | XRE family transcriptional regulator [Staphylococcus epidermidis] | SEQ ID NO: 13<br>gtgaatgactttggaaagaaattaaaagaattaagaggcgaccaatcaattagagaa<br>gcctctaggaatattggtataagtcacacttatttagatagtttagaaaaaggtattgat<br>ccaagaactggcaaagaaagaaaacctacaattgaagtaattcataaactatcaaaa<br>tattataatgttgattttttgatttaagcagattagcaggtgtgtttgtatcaattaaagat<br>acgcctaaagaagataagcggaagaaaattaacaaaatgaagaaaagatttaaaga<br>atattttaacgatacagaacttattgttaaagaaaattatcttgatattatgacaaaaaag<br>ttaagttatcatgaaattattttttggcaaaatttatataattttttatattcaagaaaaagatt<br>ctgattatctaaaaataaaagatgaagaagatacagatattttaacatttatagcttcctt<br>gtttaaaatattaactgaaaataaaaattctaatgatgacgaaatatttaaaggcatttc<br>gaatgattttaataaaattcttaaaatcatacttaaatattaagtag |

TABLE 2-continued 28 marker genes that are present in 6-HAP-producing
*S. epidermis* strains but not in any of the other strains.

| gene ID | Hypothetical Role | Sequence |
|---|---|---|
| peg.300# | C4-dicarboxylate ABC transporter [*Staphylococcus epidermidis* CIM28] | SEQ ID NO: 15<br>atgattaacactgccgtcactggtgctgaacctggaggtaactggaatccaaatatca<br>tgataagctgcgctactatagcaaagatgccacatcccagtgcaccagcagttctta<br>accctaataatatcgctagaatcatgattatgatttctatgataaacaataacatggaag<br>aatctcctaacttatgccgaacaattttcacttcaatattttatcactttaatatgtaa |
| peg.349# | uncharacterized protein | SEQ ID NO: 17<br>atgccggaagtttccggagaaatcgcttttaatttttcagcaattttagccgcagctata<br>acaagtgataaagttgatgtaagtaagaaagcagatgcaattgtagttttggtgtcaa<br>accagcgtctaatgtaa |
| peg.372# | MFS transporter [*Staphylococcus epidermidis*] | SEQ ID NO: 19<br>atgccggcaccaatcgcttggataatccgagatatcattaaaatagaaaaagtaggt<br>gaaactgctgctacaacagatcctataagaaaaattgccattgagaaaatatataaat<br>ga |
| peg.505# | hypothetical protein | SEQ ID NO: 21<br>ttgcctaagacacctgaagatgggaaaccaagtgtagataagaaaagctttgtaagt<br>gaaactatttatttttatttatgtcgattctaggagaagttttggctatgaagatgaaaa<br>agatggacaacttgtacatgatatttctccaataaaaggacaagaaaaaaatatagaa<br>aattctggttcagatgtgttttctcttatcatgtagaagacgcaatacatccatataaac<br>cagattatcttgctttatattgtttgaaatcggatcatgagaaaatagctataacagaga<br>catcttctattagtgaagcaatgaaaagattaagtacgtcaacgcttaatattcttagaa<br>aacccatgtatgaattacatccacctgcttcttttaattcaagtcatttatctagaaaagt<br>atcagtaataggaggaagtcaaaagaatcctgaattattaattcatgaaacattaatgc<br>aaggaatagaagatgaagcagaaaaagcattaagtgaattgaaagaaacgttaccg<br>gaagtttcaaatggagttcaattaaacccaggagaacttattattttagataataataaa<br>gcagcacatgctagatcagcttttaaacccagatatgacggtgaagatagatggcta<br>caaagaatgttttctattaatgacttaaaaggattagaggattacatgaaagaagacg<br>aaaatatatttgtaccccttggtggatatattaaaagacaaataa |
| peg.742# | hypothetical protein | SEQ ID NO: 23<br>atgaactttaaaacgaattttaaaggtttgtttagtatagaaaagaaatttaatgtaaattt<br>attgccatctcaactcaaattagaagataaaataaacatatagggcaacgttaatgag<br>ggttgtaggctggcttttatatacattattaattgcaagtatgactgaagttaaaaataat<br>aatattattatatacatatcatgtattttgatagtagtcttattaatatttgatataagttcaat<br>ctttcttatttctgatgatatgagaaagaaaaattatagatatttgtttatcaaaagagac<br>gaagaatatatcgtttagataaacattttttacgatattttctgataaacaagttttacaatat<br>actgtaaatgaaaaagatatgaaaattgaaaaaaataatggcgatccaaaaattgatg<br>agaaagaaaaaatagttggaaaaaagattgttactgaaaagataaatagtgataaag<br>tcaatacatttatccaaactgatagcgaggctacatatagtagcaaatatattactttag<br>tacctattgttcaaaacattatattgataataagtataatattaacagcttgttacataaac<br>tttggattgttatattatgtgcttatcatatattattgttaaatggaatatttacactacgattat<br>catctaatgtaaatgaaactttagaaaataacaatataaagcaagttaaaaataaagtg<br>aaaaatcatttaatgaagacgaaaatgataatgttggagataaaaaggatagctatg<br>aacaccgtgataagaatatcaatattatcgttgttaatgaactaaaaaagtaa |
| peg.743# | terminase small subunit [*Staphylococcus epidermidis*] | SEQ ID NO:25<br>gtggctacaccagtgtttattgatagtgttggggaagaagatgaaaagaatgagaga<br>gatttagaaaagttaagtaaactatatcctaatgcagagtttcacattgatgatattagg<br>tag |
| peg.1065# | membrane protein [*Staphylococcus epidermidis*] | SEQ ID NO: 27<br>atggctgttggattaccgcctgcaactgctttaggtacaaataaattagcgagttctttc<br>ggatctcttacagctactatctcctttattagagcaaaaaaagtaaatattaaattgatg<br>cctaaaatatttcccattgatacttgcttctattattggagcttatgttgcaactgtaattcc<br>agcgcgatattttaaacctaggcgattataatgcttttttatagtattgatttatacactcttt<br>aaaaaggattggaacggtaatacactaataaacgaaacttctaaattaaaattatttatt<br>gttttttccctactaatatttaattggcttctatgatgggattaggtggaggaacaggta<br>gtttctttatatttgttttattaattttaggattagacttttttaaaatctgcaggaaatgctaa<br>agtttttaaattttggaagtaatatggtgccctgcttttatttatattattaaataaagtaga<br>ttatttattaggtttcagtatggctttgtctatgattgttggaagctatattggtagttcattc<br>gcagtaaaaaaggtgtttcatatgtaaaattattatttataattgttactttactttttgttaa<br>taaaaaacttatatgattatatatttcagtaa |
| peg.1086# | hypothetical protein | SEQ ID NO: 29<br>atgaaattactagatgacaataattttgacttaaaactacctattaactataaaatcaata<br>ctgataattatagatcacttactcaagataaattagatgcattaagttcatctgatgctaa<br>ttttgatggtattttgggattag |

TABLE 2-continued 28 marker genes that are present in 6-HAP-producing
*S. epidermis* strains but not in any of the other strains.

| gene ID | Hypothetical Role | Sequence |
|---|---|---|
| peg.1366# | LysR family transcriptional regulator [*Staphylococcus epidermidis*] | SEQ ID NO: 31<br>atgaatcttttaatcagagaattggaaaatcattcaagagaagttggactcatagcata<br>taataaagaaatattgcaaaaagtatggagtattttaagtgaatacatagtgtaa |
| peg.1369# | ABC transporter permease [*Staphylococcus epidermidis*] | SEQ ID NO: 33<br>ttgagagatccaagccaaacattattgattaaaaagttaaaaggtatatatttcaaggc<br>ttttctaacttcatcaccatattctggaattaatgaactaaattagttgctataggtacg<br>attaatataagaaaaaccccaattgaaaatactaaagaagaacttttttactaataaagt<br>aattagaaatagaaatagaccataa |
| peg.1452# | hypothetical protein | SEQ ID NO: 35<br>atgaaaaagatgtggttaccaattataactacaatcatagtagctataattatagtatta<br>atcattttaaaaaagacaaatcatttatattttaacaacttggatacatataaagtttataa<br>agtggaagatagaaaagacatttctggtaagggtatcgatacctgaacatgttaaag<br>tgtataaaattaataaaaatataggagaatatattagaccacaaattaaagattttagaa<br>aagtgaaaaaggtactccccttatttattatgatactaatagtagcaacaggcctaat<br>ctagtggataatattaataacgttaaagaagatttaaatcgtgattatcaaaacgtagct<br>aaacacaatagcagtagttatcaaaagcaaatatctaatgattaccaaaggttatttaa<br>agctcaacaaaaattaaatcagcatgataatctgtctagtaaagatatatatgcagcttt<br>taatggtgaagtgaaaattagtaattcaattagcggtaaaaatggtgacgaaatttaa<br>aattagtttctacaaagtcagttattaagatgagagcttcacaatatatagttaataagat<br>aaaaaaaggaagtaacgttaactttaaattagatagtgacagtgaaaatgtaaaaggt<br>aaggtccagtctattgataacttacctataaatatgaaaaagaacgttactataaaaa<br>ctatgaacctaaatatatgattacaattctgatttaaatcatggtgtgagagcaggattt<br>actgggaaagtaacgattcctataatatgattgaaattcctcaaaatagtatcattaat<br>aaaaattatgattttatagttaataaggataattatgtacaaaaacgtagagttaaaatag<br>taaagattaaaaataaactcattgctaagaaaggattaaaattaggtgatcgagtcatt<br>gaaaaacctaaaagatctttacaagaaggacaacaaattaatattaaataa |
| peg.1474# | MULTISPECIE<br>S: pathogenicity island protein [*Staphylococcus*] | SEQ ID NO: 37<br>gtgcaagaaactcattacgaatttaatatagatgatgaattaagaaaactaggtttatta<br>gttggaatatccgaagaaatgtactactgctcaattagtcgaatatcaacattgtatctt<br>gaaaactttggaactaaatgggtagcatggcgtgaaacttatgattttaagaatgataa<br>aagagtatcgcacagaataatagcaaatggcagttttgaattagtagctgcaagaact<br>aaaaactatttaaactacattaaaagaaagcagggaataaaatga |
| peg.1475# | DNA primase [*Staphylococcus saccharolyticus*] | SEQ ID NO: 39<br>atgaaaatgtacaatgcagcaaagaatctccttagtaaagatgtgcaagttgtacccctt<br>aaacgataataaaaagccaacagtatcatttaagaatataactattgatgatgatttat<br>agataacaattattagcatatgcaaagacaaatgtattaggtgtcctaactcgtggttt<br>atggtgtatcgacattgatattaatcatgtaaatggtgaaagtggcttttgatagtttgaa<br>agacattccttactatgctgagtttgtttctaatgcacaaaatacgctagtgcagacaa<br>cagcaagtgggggaaagcatgtaatatttaaaaaacgtgatggtgttgaatacgctc<br>agaaaataggatatttaccatcagtagatattaaagcacatgataataactattagtatt<br>agctggaagtaaaacagctaaagggctatacactagtaataagaaaccagtaatca<br>cttatgatggtgaatttgaagatcgcattttttcaaaacgtggaaattatctacaacaga<br>ctatgaaaagttctcagtaaaaagcgtgttgcctaatcacaattttaatcatttacaac<br>atactggcaaaggtggactaggtaaagaggcatacaatcgtgtaattaatggtgaaa<br>gcatagaacgtaataatgatgtatataaagctattagttacgctttacaatgtaacgtgg<br>atatagagcctctaaaagtaattattggtgatgttaaagcaaatggtgatgaatttactt<br>agaagagtgggaggcttcatataatagtgcaagaaactcattacgaatttaa |
| peg.1476# | phage resistance protein [*Staphylococcus saccharolyticus*] | SEQ ID NO: 41<br>atggacgaagtttctttatataaaaaacattatcaattccattctaaattagataatgttga<br>tacacctaatttatctcgtataaaagaaattagtaaaagaatttactttgctgcaattaca<br>acagaaaaacaaattttaataataaaggaagtgtttatcaccaaacaaaagatgaatt<br>tgcaggtgattacattaataaccttactttagattataccataaaacctagagaaatagg<br>tgcagtctatggaactatctctgttaaaacaacagtagagaacggtgaggagaataa<br>agaggcacattttaagcctagtaaaacaaatagctatgcaaagttcattattgatctaat<br>tactgaaaagtcatctactcaaaagagttggatagctttatcaaattaaatagcaatc<br>aatatgaaattatagataatactaattttcattagagtatccggtagacaataagtatca<br>tattaatgattttcttgatgtaatgctagaagtctacaaagagtatttcattaatgattatca<br>atataatatttatccttacgctttcgcaggtaatgactggatatataattgcagaaatta<br>gaatttgtagataaaaaaattactagtaacgattactatatcatcaaatgatgtagat<br>aagaaaaatataaacactcaattagcacaaaaattattgacttagtaagtgacaatga<br>acgcagtaagaataatttaatgttggtacacgcttatactatgtatcgaaaaatgaaac<br>ttattcaagcagaaaaatggttcttaatcaaagactttgggcgatctggtaaaggtttat<br>ttatggaaacttttgaaaaacttctaaatgtaaacaaagtcaattttgatagcttattatca<br>tctggctttgaggctgcaaatgaatggcttaacttttatggtgcagatattgctcatgca<br>aatgaaacaggcgaaattaataaaggtatgatgagaatattacgcaaaatagctact<br>ggtgagaatatttcagggcgtggcatacaacgaaataacgttaagtttaaaaataatg |

TABLE 2-continued 28 marker genes that are present in 6-HAP-producing
*S. epidermis* strains but not in any of the other strains.

| gene ID | Hypothetical Role | Sequence |
|---|---|---|
| | | cagtattaattttagatactaatgaaagtgttgatactggtgaaattacagcaaatagaa<br>cacgtacagttaaaatcgcatttaaggatagaccaaagaatgaaactgatgaagaac<br>gttatcaagtatttaaaccattttgggactttgttaagcctaacgggaaaaactcagtca<br>atgcgtcagtatcatttttaatattaagtcttgagtatcttaaacaaataggcagagaatt<br>taagttcaataacgtaacacttaaaaactattacaccgaagatgaattgacggacact<br>caaattcttatgctcaaagtcttagctaaacaagattttatttttttcaggtgatgagatact<br>acaaaaaactattgaagaagattataaaaatctgaaatataaaaaagcaaaagaaga<br>tatgaaaaaaataggagtggctattaaccaacaggaatggatagagggacaaaaca<br>ctaaagttcataaagtgaaaaatcaagaattatttaatatggctttagctttgattgaaac<br>ttag |
| peg.1542# | hyperosmolarity resistance protein Emb [*Staphylococcus epidermidis*] | SEQ ID NO: 43<br>ttgcttgatgaagttgttattctatattttcatttaatggttttatatttactgtaaacgaaac<br>aatactttcattcccactttatctgtggctttaacttttacaattttatttgtgctattagtta<br>cattaggagcctga |
| peg.1635# | hypothetical protein | SEQ ID NO: 45<br>atgaataaattaaataacaaagattataaaaatattgaaggcaaattgaattacgatca<br>tatcgtaaatggcaaaaagcacattaaaaaaatgagcaaactattacaaaaacgtcg<br>taacaaagatatttcaattattaaaaaaatgtacccttatttaaataataatgaaattttag<br>aaatcactaatgattatcaagaatacaaaaatcttgttcaagctactgaaacttttacag<br>actttcctagcatttacgaaggttctaatattagtaaattcttaactgaagatgatattgc<br>agatttaaaaatggctgttgaagaaatgctagcttttgttgaaagattggaggagtag |
| peg.1638# | hypothetical protein | SEQ ID NO: 47<br>atgctaaactttgagttaaagaaacacttaaaagataaagatatgactattagtgaatta<br>agcgaaaaaactggaatatcaagaaattctttaggattattaataaatggaaaaagta<br>gaggagttcaatttgaaacacttgaaaaaatttctagagttatgaatgtagatatcaaa<br>aatttattttcaatgacttttgactttatagaaatatctgcaaaaaatgaaaaattacgtag<br>ttctgaagtaggagttgattacaatgcgtcttatgattttaaacaattagtctgtaatatg<br>aatatagatggaacagaatatgaattttctgttcaatatgaaatagattttacagttaaac<br>atattaaaagatcatagttctgaagttaaaattactattgatttaagaaagtttaactacct<br>aaatttattttttacccatcaattctgacgtagataatgaaatagcatatttaactcatgttta<br>ttttatagacactatactcaaaatcaataaagatgaaattttagaattaatgggtaaagg<br>tataaaaatatcttcaaatcaaatttcttatgtaataataaaagacgcttttcacattatttc<br>atctggtattttatatatgaataattcaagattacacaaaagagttttatgttaataaac<br>tcaaaactagtaatactataaattacatcgaagactccaataaaatacttttttacaagca<br>ggcataaaaatgttacataa |
| peg.1640# | hypothetical protein | SEQ ID NO: 49<br>ttgtcgatttaattagttttcttagtttaatttttatcaactttcgcttttt-<br>tatatgcgaacaaa<br>agacataagttgaatatgttagatcatttagatgataaatcagaatggagaaaaaaact<br>atttgaaattgcaggttcttcaaaaattggaatgggaaatttatatcaatttagagctgc<br>attaagattcacatacaaaaatgaagatgaatattatgaatataattattttgagtgcatg<br>aacataattattataaaatattgtgaaaaattaataagtcaaaatcgaatagaagatcac<br>aaacacaacgaaaacgaaaaggatcaatcttatttaaaaaatttatgaaatggattcaa<br>ttagattattttgtatttacatgttagcagatcattgggaaaaaaaacaaaacaaaattt<br>taaatttaacaatccagtaaaagaagtagaattatgtatagacaccttacaaaaatttct<br>caatattaatgataaaaactattgttataaatgccataaaagtaaattaaatagagataa<br>ttttttactgtttgtatcaccaaagtataagtttgataaattctatgacatcctaa |
| peg.1975# | ABC transporter ATP-binding protein [*Staphylococcus epidermidis*] | SEQ ID NO: 51<br>atgggctgtacgactgctgatatatagcctgttttaatcctaatctatatattttttttaagat<br>ttgtatgcgcattatctaactctaaacgctcagtattagatactttaactaaacgcatttc<br>ggtaagcactctacctaataatccactgaagttcgcaatttcagattgcgtattggtag<br>atattattgcatcacacgtcccagaggaacgatgattaaaatataaatacaggaatagta<br>ataaatgttaataaagtaatttccaatccatgataaatagcatgactaatgaacctact<br>aacgttaaaacagaaggcaataaattaggtagcttttgtgaaataaattcattaatcact<br>tttgtatcatctgttagacgactcattaattggccactttcattttttatcaaagaacggcat<br>ttttaattga |
| peg.2217# | hypothetical protein | SEQ ID NO: 53<br>atgattctatggaagaaatatgggagctatgaaatgcaaattgcatttaaagatttcaat<br>gaagataagcaaactattaatgagtatactcattttttgttcagaaagaactacattga |
| peg.2226# | hypothetical protein | SEQ ID NO: 55<br>atggatgattataactctaataatgatacgaatgattggcatgaaatcattgaacagct<br>gaagaacgataacgagatactcaaatctaacaatcaagaacttcagcaacatattcat<br>cagctggaagacgagatagacccaatgagcaagaaaatgatgtttttcatcattat<br>tacaacattttgatagtacagcatttatgaacttcaatacatatcgtgatgatcgcccatt<br>aaaaaatgcgattaaacgattgaaagaacaataa |

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating or preventing skin damage due to UV radiation comprising contacting the skin with an effective amount of a composition comprising a compound of Formula I(a):

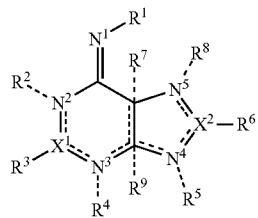

Formula I(a)

or a pharmaceutically acceptable salt thereof, wherein, $N^1$-$N^5$ are nitrogen atoms;

$X^1$-$X^2$ are carbon atoms;

the R groups attached by a dashed line are present, or are not present if the R group is connected to an atom that is bound to another atom by a double covalent bond;

the bond indicated by both a straight line and a dashed line indicate that the bond may be a single covalent bond or a double covalent bond;

the fused heterocyclic ring system comprises three double bonds with $N^2$ or $N^3$ forming a double bond and with $X^1$, and with $N^4$ or $N^5$ forming a double bond with $X^2$;

$R^1$ is a hydroxyl; and $R^2$, $R^3$, $R^4$, $R^5$, $R^6$, $R^7$, $R^8$, and $R^9$ are independently a H, D, optionally substituted ($C_1$-$C_3$)-alkyl.

2. The method of claim 1, wherein the method treats or prevents skin damage leading to a cancer selected from the group consisting of melanoma, squamous cell carcinoma, actinic keratosis, keratoacanthoma, and basal cell carcinoma.

3. The method of claim 1, wherein the contacting is through topical administration.

4. The method of claim 1, wherein the composition further comprises one or more sunscreen agents.

5. The method of claim 4, wherein one or more sunscreen agents comprises aminobenzoic acid, avobenzone, cinoxate, dioxybenzone, ecamsule, ensulizole, homosalate, meradimate, octocrylene, octinoxate, octisalate, oxybenzone, padimate O, sulisobenzone, titanium dioxide, trolamine salicylate, and zinc oxide.

6. The method of claim 1, wherein the composition is formulated for topical administration.

7. The method of claim 1, wherein the composition is formulated as a spray, lotion, shake lotion, cream, ointment, gel, foam, powder, solid, paste or tincture.

8. The method of claim 1, wherein the composition comprises a commensal probiotic bacteria that produces the compound of Formula I(a)

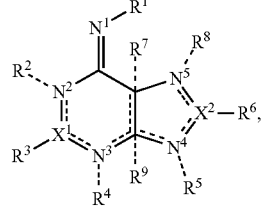

a compound of Formula I(b)

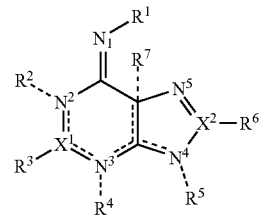

or a compound of Formula II

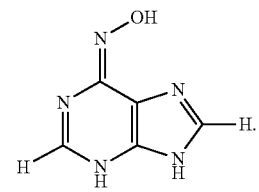

9. The method of claim 8, wherein the commensal probiotic bacteria expresses one or more of the sequences set forth in SEQ ID Nos: 1, 3, 5, 7, 9, 11, 13, 15, 17, 19, 21, 23, 25, 27, 29, 31, 33, 35, 37, 39, 41, 43, 45, 47, 49, 51, 53, and/or 55.

10. The method of claim 8, wherein the commensal probiotic bacteria comprises S. epidermidis strain MO34 and/or MO38.

11. The method of claim 1, wherein the composition improves healing and reduces morbidity associated with skin damage.

12. The method of claim 1, wherein the method treats or prevents a neoplasm caused by UV-induced skin damage.

13. The method of claim 1, wherein the composition further comprises one or more topical antibiotics.

14. The method of claim 13, wherein the one or more topical antibiotics comprises sulfacetamide sodium, bacitracin, polymyxin b, erythromycin, silver sulfadiazine, neomycin, retapamulin, and mupirocin.

15. The method of claim 1, wherein the composition comprises one or more gelling agents selected from the group comprising crosslinked acrylic acid polymers, hydrophilic polymers, cellulosic polymers, gums, or any combination thereof.

* * * * *